(12) United States Patent
Tang et al.

(10) Patent No.: US 11,871,662 B2
(45) Date of Patent: Jan. 9, 2024

(54) CHIRAL AGGREGATION-INDUCED EMISSION LUMINOGENS WITH DELAYED FLUORESCENCE FOR CIRCULARLY POLARIZED ORGANIC LIGHT-EMITTING DIODES

(71) Applicant: The Hong Kong University of Science and Technology, Hong Kong (CN)

(72) Inventors: Benzhong Tang, Hong Kong (CN); Fengyan Song, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 829 days.

(21) Appl. No.: 15/733,399

(22) PCT Filed: Feb. 14, 2019

(86) PCT No.: PCT/CN2019/075038
§ 371 (c)(1),
(2) Date: Jul. 21, 2020

(87) PCT Pub. No.: WO2019/165890
PCT Pub. Date: Sep. 6, 2019

(65) Prior Publication Data
US 2021/0119143 A1    Apr. 22, 2021

Related U.S. Application Data

(60) Provisional application No. 62/710,806, filed on Feb. 28, 2018.

(51) Int. Cl.
*H10K 85/60* (2023.01)
*C07D 209/86* (2006.01)
*C07D 219/16* (2006.01)
*C09K 11/02* (2006.01)
*C09K 11/06* (2006.01)
(Continued)

(52) U.S. Cl.
CPC ....... *H10K 85/6572* (2023.02); *C07D 209/86* (2013.01); *C07D 219/16* (2013.01); *C09K 11/02* (2013.01); *C09K 11/06* (2013.01); *H10K 85/626* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 2101/20* (2023.02)

(58) Field of Classification Search
CPC .................................................. H10K 2101/20
See application file for complete search history.

(56) References Cited

U.S. PATENT DOCUMENTS

2018/0323394 A1 * 11/2018 Haldi ................. H10K 85/6572

FOREIGN PATENT DOCUMENTS

CN        107629785 A  *  1/2018

OTHER PUBLICATIONS

Feuillastre, Sophie et al, Design and Synthesis of New Circularly Polarized Thermally Activated Delayed Fluorescence Emitters, J. Am. Chem. Soc., vol. 138, 3990-3993, Mar. 11, 2016.

(Continued)

*Primary Examiner* — Sean M DeGuire
(74) *Attorney, Agent, or Firm* — S&F/WEHRW

(57) ABSTRACT

Provided herein are chiral compounds that exhibit circularly polarized photoluminescence and electroluminescence and electroluminescent devices and circularly polarized fluorescent probes comprising the same.

18 Claims, 55 Drawing Sheets

(51) Int. Cl.
  *H10K 50/11*   (2023.01)
  *H10K 50/15*   (2023.01)
  *H10K 50/16*   (2023.01)
  *H10K 50/17*   (2023.01)
  *H10K 101/20*  (2023.01)

(56) References Cited

OTHER PUBLICATIONS

Song, Fengyan et al, Highly Efficient Circularly Polarized Electroluminescence from Aggregation-Induced Emission Luminogens with Amplified Chirality and Delayed Fluorescence, Adv. Funct. Mater., vol. 28, 1800051(1-12), Feb. 28, 2018.

* cited by examiner

Table 1.

| | Solution | | | Neat Film | | | | Doped Film | | | |
|---|---|---|---|---|---|---|---|---|---|---|---|
| | $\lambda_{abs}$ [nm] | $\lambda_{em}$ [nm] | $\Phi_{PL}$ [%] | $\lambda_{em}$ [nm] | $\Phi_{PL}$ [%] | $\tau_{prompt}$ [ns] | $\tau_{delayed}$ [μs] | $k_{RISC}$ [μs$^{-1}$] | $\lambda_{em}$ [nm] | $\Phi_{PL}$ [%] | $\tau_{prompt}$ [ns] | $\tau_{delayed}$ [μs] | $k_{RISC}$ [μs$^{-1}$] |
| S-BN-CF | 400 | 495 | 24.7 | 520 | 38.7 | 22.33 | 1.67 | 0.62 | 493 | 32.0 | 162.3 | 24.33 | 3.87 |
| S-BN-CCB | 420 | 530 | 27.2 | 538 | 19.6 | 12.55 | 1.43 | 1.07 | 534 | 37.9 | 21.27 | 2.51 | 0.75 |
| S-BN-DCB | 440 | 531 | 30 | 553 | 22.1 | 11.27 | 1.33 | 0.56 | 540 | 44.8 | 16.91 | 1.77 | 1.14 |
| S-BN-AF | 450 | 585 | 1.5 | 580 | 5.3 | 12.62 | 0.46 | 2.38 | 571 | 12.5 | 31.96 | 1.07 | 1.68 |

FIG. 3

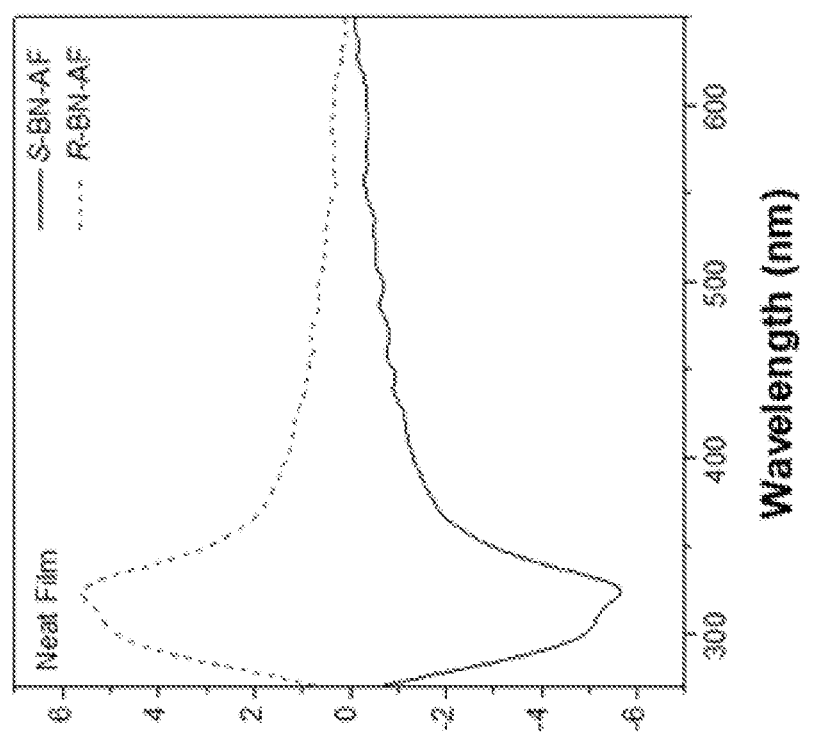
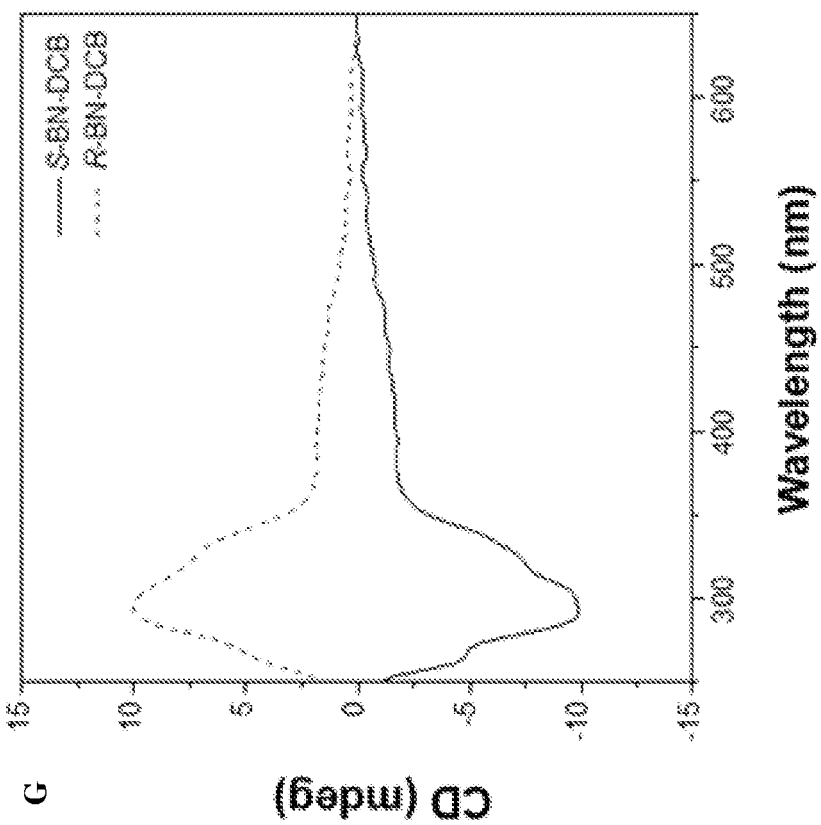
FIG. 5 (Continued)

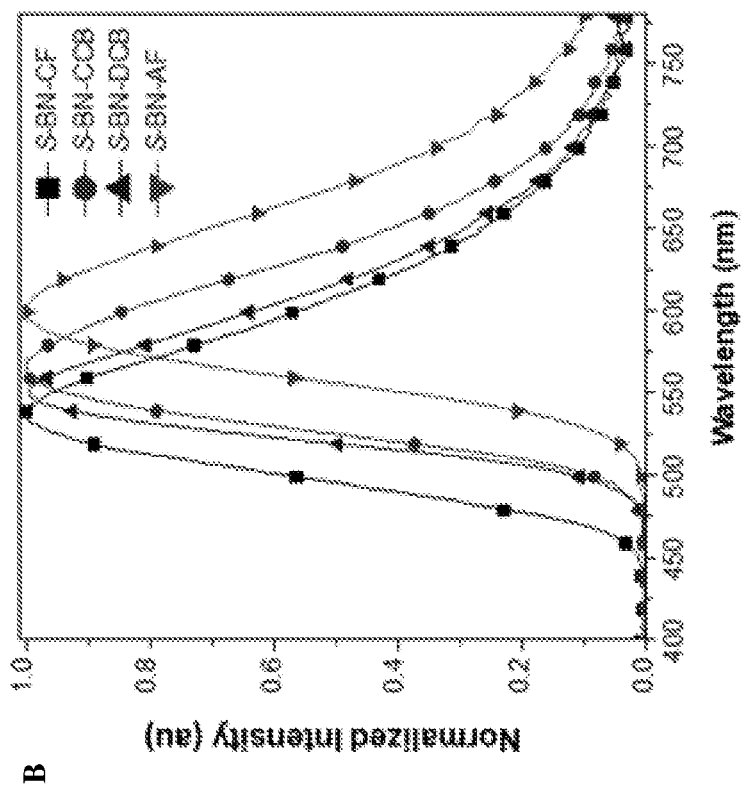
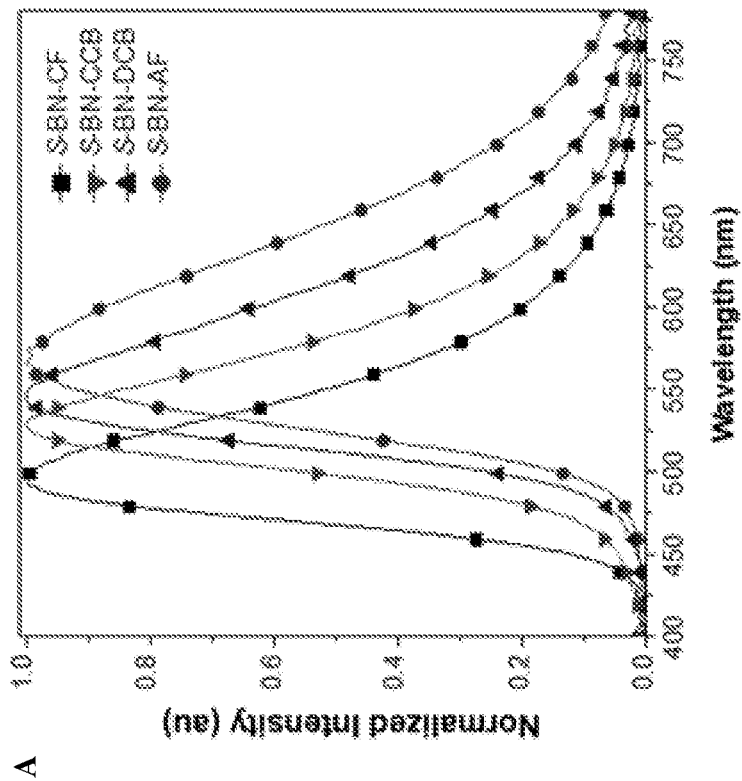
FIG. 7

Table 2.

| Device | $V_{on}$ [V] | Maximum Values | | | | Values at 1000 cd m$^{-2}$ | | | | | |
|---|---|---|---|---|---|---|---|---|---|---|---|
| | | $\eta_c$ [cd A$^{-1}$] | $\eta_p$ [lm W$^{-1}$] | $\eta_{ext}$ [%] | $L$ [cd m$^{-2}$] | $V$ [V] | $\eta_c$ [cd A$^{-1}$] | $\eta_p$ [lm W$^{-1}$] | $\eta_{ext}$ [%] | RO [%] | $\lambda_{EL}$ [nm] |
| A | 3.6 | 24.6 | 19.6 | 9.3 | 2948 | 5.8 | 11.5 | 6.2 | 4.4 | 53.3 | 496 |
| B | 3.6 | 20.9 | 18.2 | 6.3 | 4199 | 6.6 | 12.1 | 5.8 | 3.9 | 42.0 | 527 |
| C | 3.4 | 10.5 | 9.1 | 3.5 | 5056 | 5.6 | 8.1 | 4.6 | 2.7 | 22.3 | 547 |
| D | 4.0 | 4.2 | 2.9 | 1.7 | 3032 | 7.2 | 3.8 | 1.7 | 1.5 | 8.2 | 571 |
| E | 3.8 | 10.3 | 6.7 | 3.5 | 2570 | 8.8 | 9.1 | 3.2 | 3.1 | 11.7 | 537 |
| F | 3.8 | 6.3 | 4.4 | 2.3 | 6633 | 7.2 | 5.7 | 2.5 | 2.1 | 9.6 | 563 |
| G | 4.8 | 8.7 | 4.8 | 2.9 | 5729 | 7.0 | 8.0 | 3.6 | 2.7 | 8.0 | 550 |
| H | 3.8 | 1.1 | 0.7 | 0.6 | 1473 | 10.2 | 1.1 | 0.3 | 0.5 | 3.7 | 597 |

FIG. 8

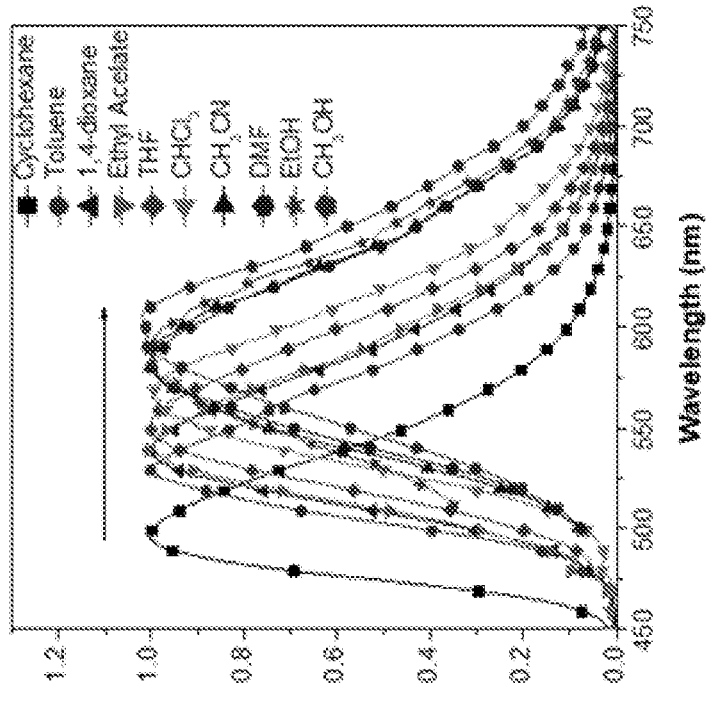
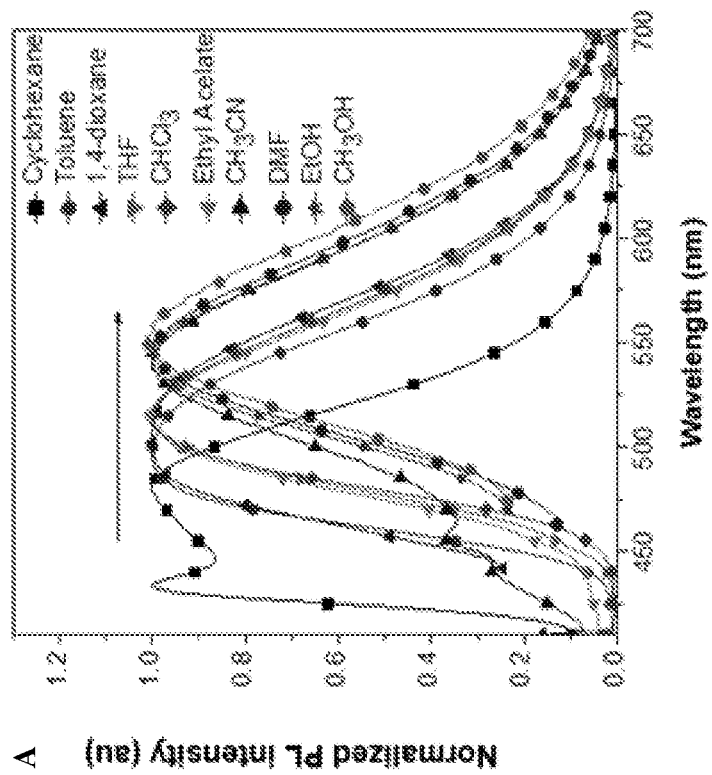
FIG. 15

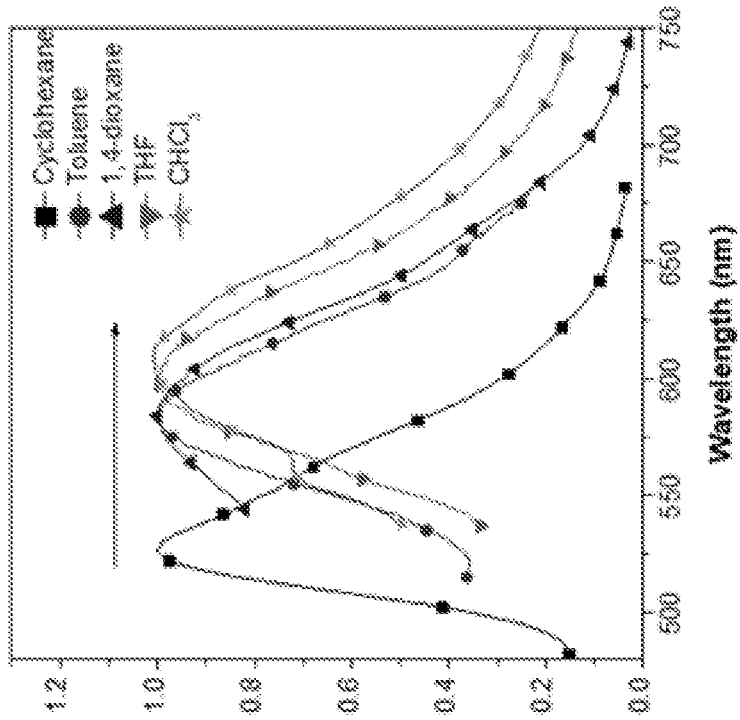
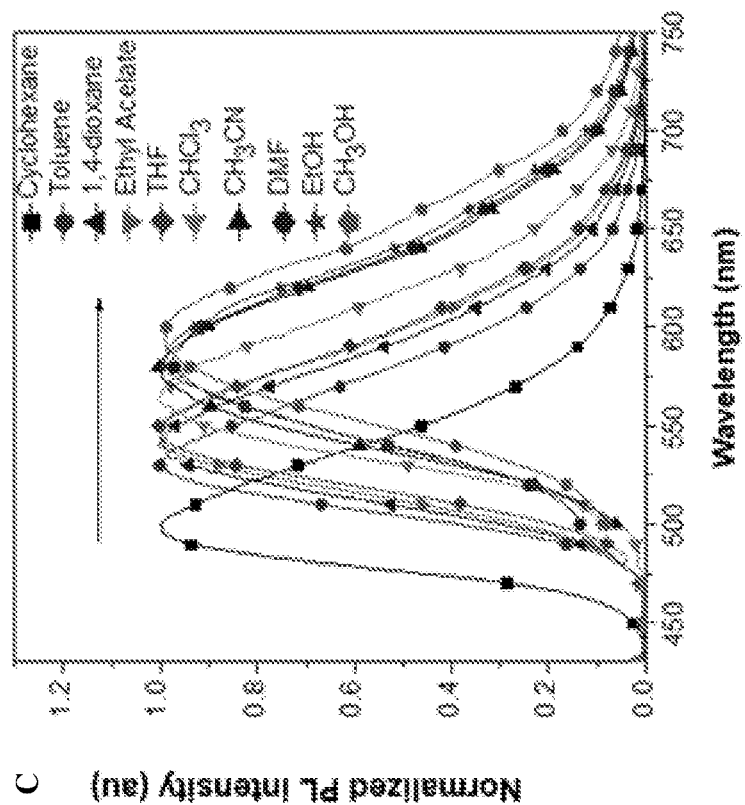
FIG. 15 (Continued)

Table 3

| Compound | State | $\langle\tau\rangle$ [ns] | $\tau 1$ [ns] | $\tau 2$ [ns] | A1 | A2 | $R_{prompt}$ (%) | $R_{delayed}$ (%) |
|---|---|---|---|---|---|---|---|---|
| S-BN-CF | Toluene | 17.76 | - | - | - | - | - | - |
| | Neat film | 73.36 | 22.33 | 1673.86 | 27186 | 11.57 | 96.91 | 3.09 |
| | Doped film | 24080 | 162.3 | 24336.5 | 8927 | 5562 | 1.06 | 98.94 |
| S-BN-CCB | Toluene | 18.07 | - | - | - | - | - | - |
| | Neat film | 229.66 | 12.55 | 1432.52 | 17271 | 27.33 | 84.71 | 15.29 |
| | Doped Film | 1175.2 | 21.27 | 2505.07 | 3199.8 | 23.58 | 53.54 | 46.46 |
| S-BN-DCB | Toluene | 14.92 | - | - | - | - | - | - |
| | Neat film | 254.62 | 11.27 | 1330.27 | 27700 | 153.09 | 81.55 | 18.45 |
| | Doped film | 904.60 | 16.91 | 1773.33 | 4376.36 | 42.67 | 49.46 | 50.54 |
| S-BN-AF | Toluene | 8.55 | - | - | - | - | - | - |
| | Neat film | 63.18 | 12.62 | 463.64 | 9291.3 | 31.93 | 88.79 | 11.21 |
| | Doped film | 496.4 | 31.96 | 1075.10 | 4652.4 | 111.0 | 55.48 | 44.52 |

FIG. 20

Table 4

|  | S-BN-CF | | S-BN-CCB | | S-BN-DCB | | S-BN-AF | |
|---|---|---|---|---|---|---|---|---|
|  | Neat film | 10%w in mCP | Neat film | 10%w in mCP | Neat film | 10%w in mCP | Neat film | 10%w in mCP |
| $\Phi_{PL}$ [%] | 38.7 | 32.0 | 19.6 | 37.9 | 22.1 | 44.8 | 5.3 | 12.5 |
| $\tau_{prompt}$ [ns] | 22.33 | 162.3 | 12.55 | 21.27 | 11.27 | 16.91 | 12.62 | 31.96 |
| $\tau_{delayed}$ [ns] | 1673.86 | 24336.5 | 1432.52 | 2505.07 | 1330.27 | 1773.33 | 463.64 | 1075.10 |
| $R_{delayed}$ [%] | 3.09 | 98.94 | 15.29 | 46.46 | 18.45 | 50.54 | 11.21 | 44.52 |
| $\Phi_{prompt}$ [%] | 37.5 | 0.3392 | 17.40 | 20.29 | 18.02 | 22.15 | 4.71 | 6.935 |
| $\Phi_{delayed}$ [%] | 1.20 | 31.66 | 3.00 | 17.61 | 2.48 | 22.64 | 0.59 | 5.565 |
| $\Phi_{ISC}$ [%] | 3.10 | 98.93 | 11.22 | 46.46 | 18.48 | 50.56 | 11.32 | 44.52 |
| $\Phi_{RISC}$ [%] | 38.7 | 32 | 26.72 | 37.9 | 13.42 | 44.78 | 5.21 | 12.5 |
| $k_F$ [×10$^6$ s$^{-1}$] | 16.79 | 0.021 | 13.86 | 9.54 | 16.07 | 13.10 | 3.73 | 2.17 |
| $k_{IC}$ [×10$^6$ s$^{-1}$] | 26.59 | 0.044 | 56.87 | 15.63 | 56.64 | 16.14 | 66.65 | 15.18 |
| $k_{ISC}$ [×10$^6$ s$^{-1}$] | 1.39 | 6.09 | 8.94 | 21.84 | 16.48 | 29.89 | 8.99 | 13.92 |
| $k_{RISC}$ [×10$^6$ s$^{-1}$] | 0.62 | 3.87 | 1.07 | 0.75 | 0.56 | 1.14 | 2.38 | 1.68 |

FIG. 21

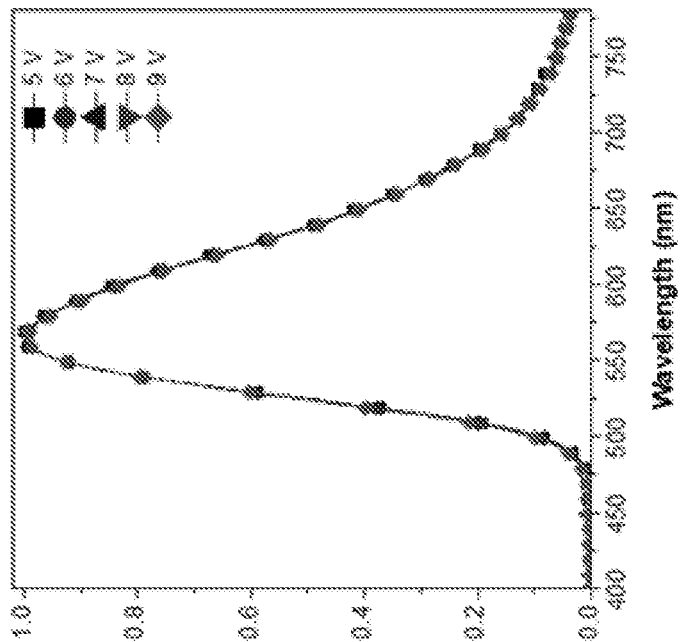
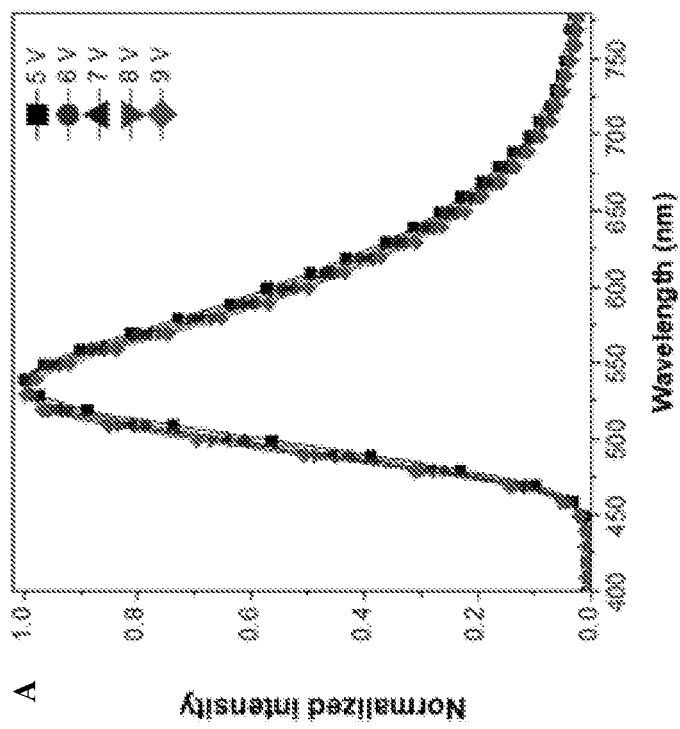
FIG. 27

A
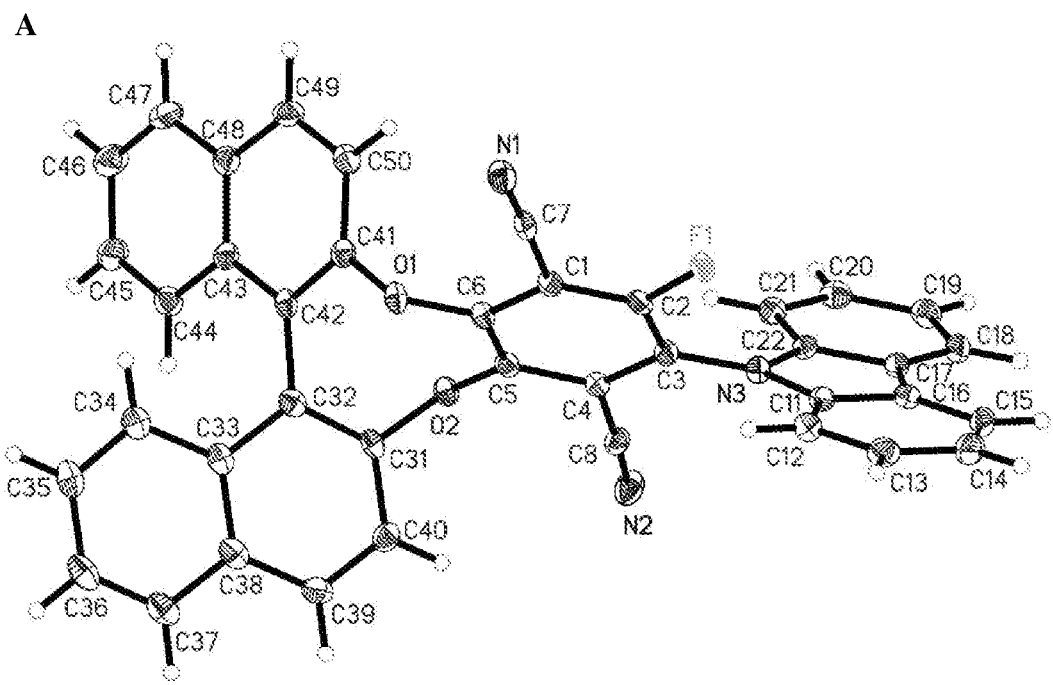
B
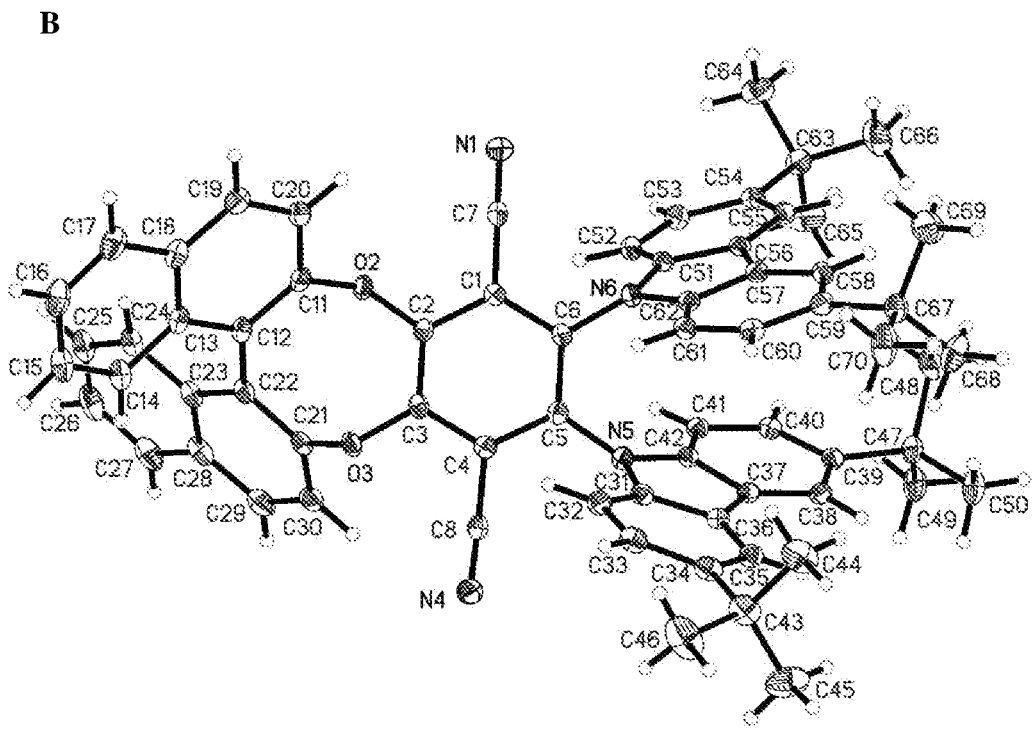
FIG. 30

C

Table 5

| Materials | Structure of emitting layer | $\lambda_{em}$ nm | $\|g_{EL}\|$ | L cd $m^2$ | $\eta_c$ cd/A | $\eta_{ext}$ % | RO | Published year and Ref |
|---|---|---|---|---|---|---|---|---|
| PPV | Pure polymer layer | 600 | $10^{-3}$ | - | - | - | - | 1997/6 |
| PF | Pure polymer layer | 425 | 0.05-0.25 | - | - | - | - | 2000/7 |
| Oligomers | Pure polymer layer | 425-450 | 0.35 | - | 0.94 | - | - | 2003/8 |
| PFPT | Pure polymer layer | 540 | 0.80 | 80 | - | - | - | 2017/9 |
| PF | PF with chiral semiconducting dopant | 540 | 0.20 | 3000 | 3.67 | - | - | 2013/1a |
| Chiral Europium Complex | Dispersed in PVK and OXD7 | 595 | 0.79-1.0 | 3.0 | - | 0.0042 | - | 2015,2017/ 10,11 |
| platinahelicene | Dispersed in PVK and OXD7 | 625 | 0.22-0.38 | 230 | 0.52 | - | - | 2016/1b |
| F8BT | F8BT with chiral R5011 | 540 | 1.13 | 4000 | 4.46 | - | - | 2017/12 |
| Chiral Iridium Complexes | Dispersed in PVK and OXD7 | 527-556 | $10^{-3}$ | 4473 | 7.5 | - | - | 2017/13 |
| Chiral Iridium Complexes | Dispersed in mCP | 540-580 | 0.0026 | - | - | - | - | 2015/14 |
| Exemplary Compounds | Pure AIEgens | 537-597 | 0.05-0.09 | 1473 - 6633 | 1.1-10.3 | 0.6-3.5 | 3.7-11.7 | This work |
| | Dispered in mCP | 496-571 | 0.016-0.027 | 2948 - 5056 | 2.9-19.6 | 1.7-9.3 | 8.2-53.8 | |

FIG. 31

CHIRAL AGGREGATION-INDUCED EMISSION LUMINOGENS WITH DELAYED FLUORESCENCE FOR CIRCULARLY POLARIZED ORGANIC LIGHT-EMITTING DIODES

CROSS-REFERENCE TO RELATED APPLICATIONS

This application claims the benefit of priority of U.S. Provisional Application No. 62/710,806, filed on Feb. 28, 2018, the contents of which being hereby incorporated by reference in their entirety for all purposes.

FIELD OF THE INVENTION

The present disclosure generally relates to chiral compounds that exhibit circularly polarized luminescence and electroluminescence useful for the construction of circularly polarized (CP) electroluminescent devices and materials, such as circularly polarized organic light-emitting diodes (CPOLED) and circularly polarized fluorescent probes.

BACKGROUND OF THE INVENTION

Circularly polarized luminescence has recently brought fresh insights to the role of chiral structure and local electronic environment in the problem of light-mater interactions with chiral materials. More importantly, these luminogenic materials with circularly polarized luminescence have also received increasing interest, owing in part to their potential application in optical data storage, optical recognition sensor, quantum computing, optical communication for spintronics and three-dimensional displays. They are especially promising for fabricating CPOLEDs. Currently, OLED based flat panel displays need a polarizer and a quarter-wave plate to reduce reflectance from the surroundings for high image contrast. If CPOLEDs are well developed, efficient electroluminescence from the molecules can be extracted without absorption loss to the polarizer, leading to energy savings in the OLED display. In addition, high contrast 3D images could also be achieved by the development of improved CPOLEDs. Therefore, the development of CPOLED materials and technology is particularly important.

In 1997, Meijer and coworkers, for the first time, observed the circularly polarized electroluminescence (CPEL) phenomenon from a chiral conjugated polymer and since then great efforts have been devoted for the development of CP luminescent devices. Several pioneering and important works conducted and promoted by several researchers in the realm of CPEL and its signal enhancements characterized by hugely boosted $g_{EL}$ values. Herein, $g_{EL}=2(I_L-I_R)/(I_L+I_R)$, where $I_L$ and $I_R$ are the emission intensities of left and right circularly polarized luminescence, respectively. In particularly, Fuchter and co-workers developed a new strategy to fabricate CPOLEDs by doping the light-emitting polymer with chiral molecule. A $g_{EL}$ value of 0.2 was obtained by doping an achiral polymer with chiral helicene molecule. The mechanism of obtained strong circularly polarized luminescence (CPL) signals in these alignment luminescent layers could be attributed to the formation of large cholesteric domains. In sequence recent cases, a series of high $g_{EL}$ values of CPOLEDs were reported by Nuzzo, Kim, Bari, etc Although high $g_{EL}$ values based CPOLED devices associated with theoretical consideration of strong circular polarization had been well elaborated by these excellent works, the pursuing of CPOLEDs with high external quantum efficiency (EQE) and small efficiency roll-off remains challenging. Fuchter and co-workers use a platinahelicene complex to construct a CP-PHOLED for high luminescence efficiency that achieves both a display level brightness ($L_{max}$=230 cd/m$^2$, $CE_{max}$=0.52 cd/A) and high $g_{EL}$ value (−0.38). In an alternative approach, some chiral iridium complexes were found to possess high EQE but very low $g_{EL}$ values of up to only $10^{-3}$ order by Huang, W. et al. and Zheng, Y-X. et al. Among the scattered efforts, CPOLEDs with both relative high $g_{EL}$ factors and high EQE are rare so far. Our previous work has confirmed that the incorporation of chiral attachments into the peripheries of typical aggregation-induced emission (AIE) structures can efficiently induce the CPPL signals amplification in aggregated state. Moreover, AIEgens with delayed fluorescence property were proved to be a feasible strategy to generate robust luminescent materials that could improve EL efficiency and suppress efficiency roll-off. Therefore, chiral AIEgens with delayed fluorescence may lead to materials promising as emitting layers for efficient CPOLEDs.

SUMMARY

Provided herein are chiral AIE luminogenic compounds with delayed fluorescence. AIE, twisted intramolecular charge transfer (TICT) and thermally activated delayed fluorescence (TADF) properties were fully investigated for these compounds. The photophysical properties (absorption and photoluminescence spectra) can be facilely tuned by changing the electron donating or/and withdrawing properties of the donor or/and acceptor units. These compounds can exhibit maximal luminescence peaks from green to orange spectral region (490-600 nm), and high brightness in the solid state. More interestingly, the compounds can exhibit excellent CPEL performance. Preliminary experiments indicate that these compounds with delayed fluorescence can be developed in to high efficiency CPOLED.

In a first aspect, provided herein is a compound of Formula I:

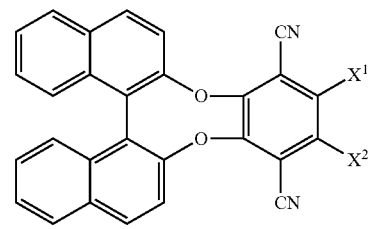

wherein each of $X^1$ and $X^2$ is independently selected from the group consisting of:

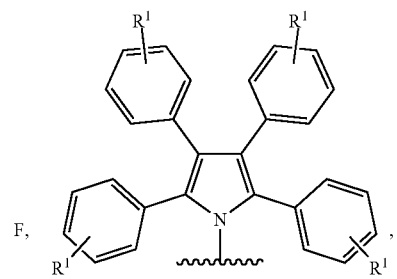

-continued

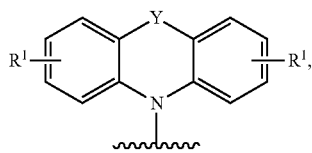

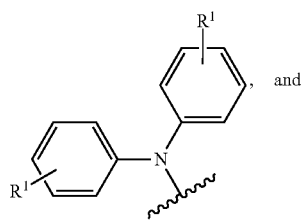

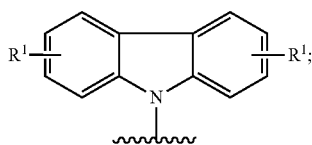

R[1] for each instance is independently selected from the group consisting of halide, H, alkyl, alkene, alkyne, heteroalkyl, cycloalkyl, heterocycloalkyl, aryl, heteroaryl, carboxyl, —NR$_2$, sulfonic acid, —SR, and —OR;

Y is —N(R)—, O, S, Se, Te, or —C(R)$_2$—;

wherein at least one R[1] optionally further comprises a terminal functional group selected from the group consisting of N$_3$, NCS, SH, NH$_2$, COOH, alkyne, N-hydroxysuccinimide ester, maleimide, hydrazide, nitrone group, —CHO, OH, halide, and charged ionic group; and R for each instance is independently selected from the group consisting of H, alkyl, cycloalkyl, aryl, and heteroaryl, with the proviso that if X[1] is N-carbazole, then X[2] is not N-carbazole and if X[1] is F, then X[2] is not F.

In a first embodiment of the first aspect, provided herein is the compound of the first aspect, wherein R[1] for each instance is independently selected from the group consisting of H and alkyl.

In a second embodiment of the first aspect, provided herein is the compound of the first aspect, wherein each of X[1] and X[2] is independently selected from the group consisting of:

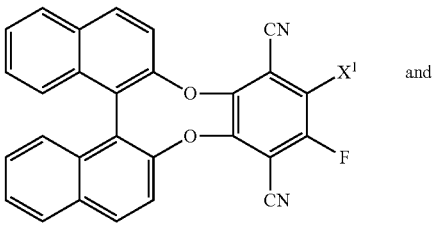

wherein Y is —N(R)—, O, or —C(R)$_2$— and R is independently H or alkyl.

In a third embodiment of the first aspect, provided herein is the compound of the first aspect, wherein the compound of Formula I is selected from the group consisting of:

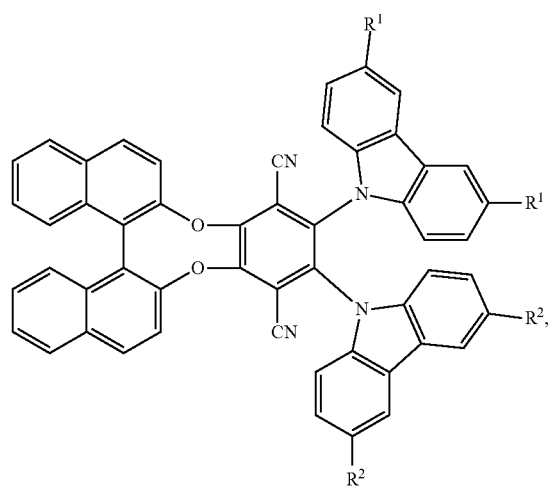

wherein X[1] is

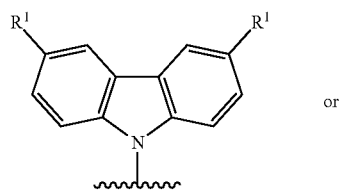

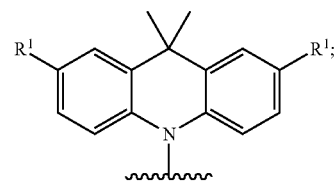

R[1] for each instance is H or alkyl; and R[2] for each instance is H or alkyl.

In a fourth embodiment of the first aspect, provided herein is the compound of the first aspect, wherein the compound of Formula I is represented by:

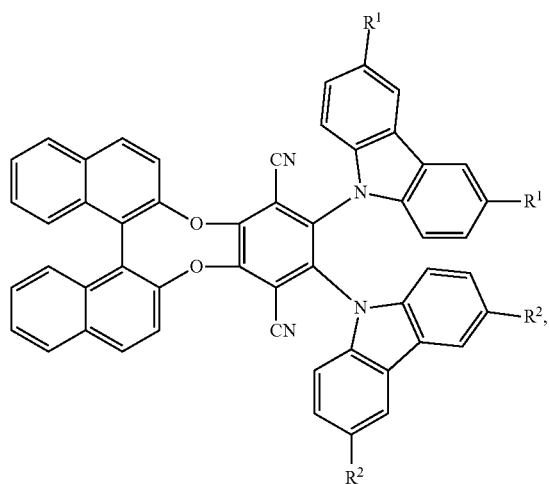

wherein $R^1$ is H or alkyl and $R^2$ is alkyl.

In a fifth embodiment of the first aspect, provided herein is the compound of the first aspect, wherein the compound of Formula I is represented by:

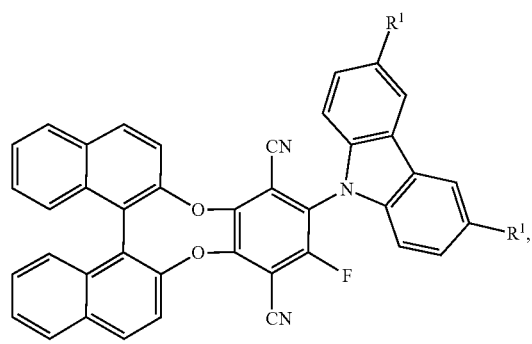

wherein $R^1$ is H or alkyl with the proviso that if $R^1$ is H, the compound is isolated, pure, or present in a film.

In a sixth embodiment of the first aspect, provided herein is the compound of the first aspect, wherein the compound of Formula I is represented by:

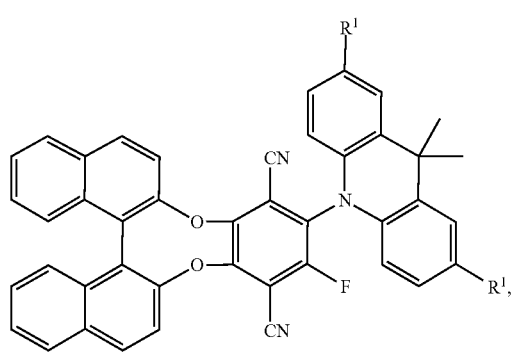

wherein $R^1$ is H or alkyl.

In a seventh embodiment of the first aspect, provided herein is the compound of the first aspect, wherein the compound of Formula I is selected from the group consisting of:

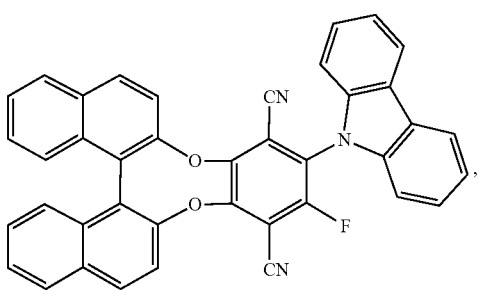

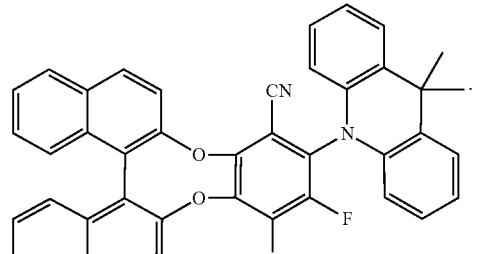

In an eighth embodiment of the first aspect, provided herein is the compound of the first aspect, wherein the compound is present in a thin film.

In a ninth embodiment of the first aspect, provided herein is the compound of the first aspect, wherein the compound exhibits a photoluminescence dissymmetry factor in the solid state between 0.02 to 0.05 calculated from the maximum emission wavelength.

In a second aspect, provided herein is an electroluminescent device comprising the compound of the first aspect.

In a first embodiment of the second aspect, provided herein is the electroluminescent device of the second aspect, wherein the electroluminescent device comprises:

an anode;

a hole-injection layer;

a hole-transport layer;

an electron-transport layer;

an electron-injection layer;

a light-emitting layer comprising the compound of Formula I; and a cathode layer, wherein at least one of the anode layer and the cathode layer being substantially transparent to electroluminescent light.

In a second embodiment of the second aspect, provided herein is the electroluminescent device of the first embodiment of the second aspect, wherein the light-emitting layer further comprises a host matrix and the compound of Formula I is used as a dopant material.

In a third embodiment of the second aspect, provided herein is the electroluminescent device of the second aspect, wherein the compound of Formula I is selected from the group consisting of:

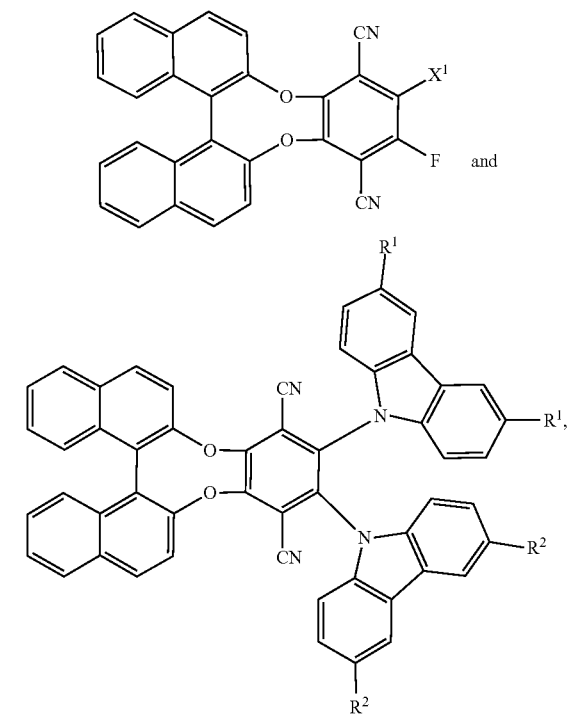

wherein $X^1$ is

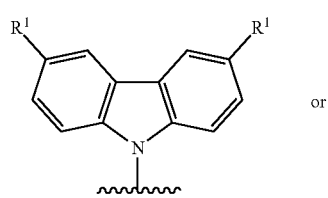

or

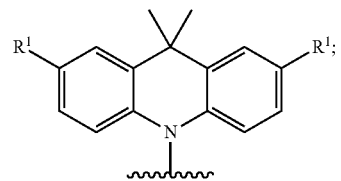

$R^1$ for each instance is H or alkyl; and $R^2$ for each instance is H or alkyl.

In a fourth embodiment of the second aspect, provided herein is the electroluminescent device of the second aspect, wherein the compound of Formula I is selected from the group consisting of:

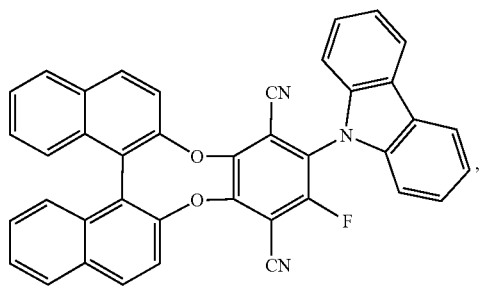

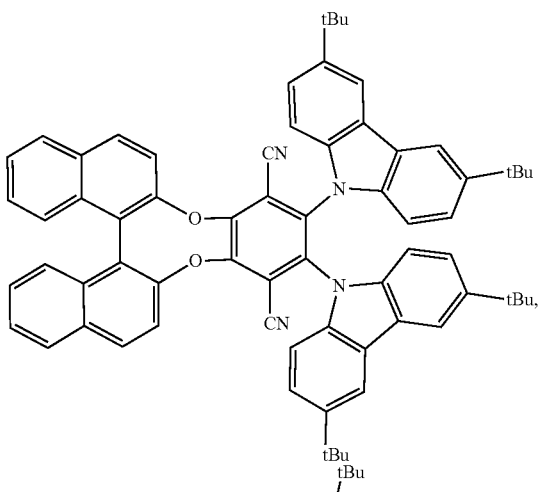

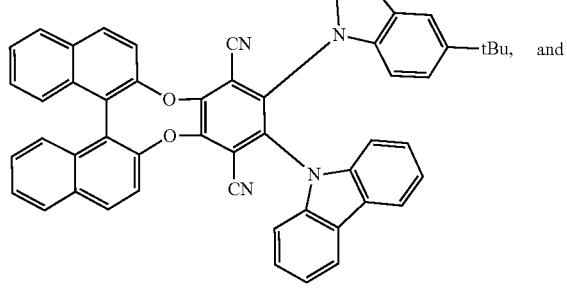

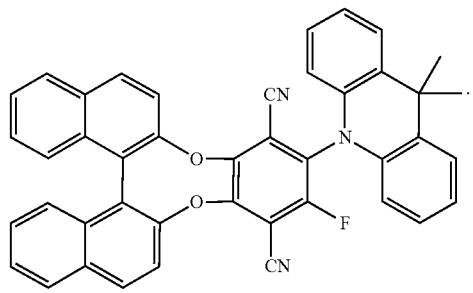

In a fifth embodiment of the second aspect, provided herein is the electroluminescent device of the first embodiment of the second aspect, wherein the electron-injection layer comprises lithium-8-hydroxyquinolinolate (Liq), the electron-transport layer comprises 1,3-bis[3,5-di(pyridin-3-yl)phenyl]benzene (BmPyPhB), the hole-injection layer comprises 1,4,5,8,9,11-hexaazatriphenylenehexacarbonitrile (HATCN), the hole-transport layer comprises (TCTA), and the light-emitting layer further comprises N,N'-dicarbazolyl-3,5-benzene (mCP).

In a sixth embodiment of the second aspect, provided herein is the electroluminescent device of the fifth embodiment of the second aspect, wherein the compound of Formula I is selected from the group consisting of:

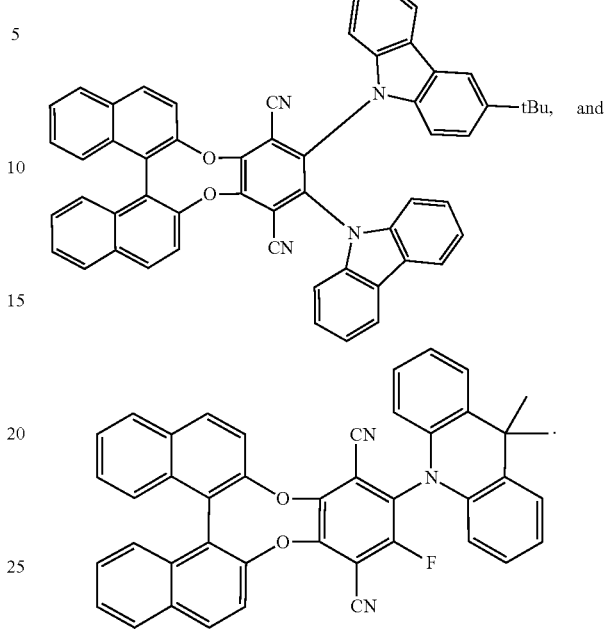

In a seventh embodiment of the second aspect, provided herein is the electroluminescent device of the first embodiment of the second aspect, wherein the compound exhibits an electroluminescence dissymmetry factor between 0.05 to 0.090 calculated from the maximum emission wavelength.

In an eighth embodiment of the second aspect, provided herein is the electroluminescent device of the first embodiment of the second aspect, wherein the electroluminescent device has a maximum power efficiency between 18 to 20 lm·W$^{-1}$.

In a tenth embodiment of the second aspect, provided herein is the electroluminescent device of the first embodiment of the second aspect, wherein the electroluminescent device has a turn on voltage of 3.4 to 3.8 volts.

The compounds provided herein can exhibit external quantum efficiencies as high as 9.3% and 3.5% with the relative high electroluminescence dissymmetry factor ($g_{EL}$)+0.026/−0.021 and +0.06/−0.06 for doped film and neat film, respectively (FIG. 7). Moreover, compared with doped CPOLED the nondoped CPOLED surprisingly provide higher $g_{EL}$ values and much smaller current efficiency roll-offs [Table 2 (FIG. 8), FIGS. 7E and 7F] that are believed to result from AIE properties of the compounds. The nondoped CPOLED provide peak EL efficiencies of 10.3 cd A$^{-1}$, and 6.7 lm W$^{-1}$ and 3.51% for BN-CF, with small current efficiency roll-off of 11.7% at 1000 cd m$^{-2}$ and relative high $|g_{EL}|$ value of 0.06. The multicolor electroluminescence from 493 nm to 571 nm based CPOLEDs for doped film and from 537 nm to 597 nm for neat films based emitting layers were also achieved by altering donor unites (FIGS. 7A and 7B).

BRIEF DESCRIPTION OF DRAWINGS

The above and other objects and features of the present disclosure will become apparent from the following description of the present invention, when taken in conjunction with the accompanying drawings, in which:

FIG. 3 depicts Table 1 which shows photophysical properties of S-BN-CF, S-BN-CCB, S-BN-DCB and S-BN-AF. Abbreviation: Soln, measured in toluene solution at room temperature; Neat film, deposited on a quartz substrate; Doped film, in mCP matric (10 wt %) deposited on a quartz substrate; $\Phi_{PL}$, determined using an integral sphere; PL lifetime of prompt ($\tau_{prompt}$) and delayed ($\tau_{delayed}$) decay components evaluated at 300K under $N_2$ atmosphere; $k_{RISC}$, the rate of reverse intersystem crossing process from the triplet to singlet state.

FIG. 8 depicts Table 2, which shows EL performance of the CP-OLEDs based on S-BN-CF, S-BN-CCB, S-BN-DCB and S-BN-AF. Abbreviation: Von=turn-on voltage at 1 cd m-2; ηc=current efficiency; ηp=power efficiency; ηext=external quantum efficiency; RO=current efficiency roll-off from maximum values to that at 1000 cd m-2. Device configurations: Device A: ITO/HATCN (10 nm)/ TAPC: HATCN (5: 2, 60 nm)/TCTA (20 nm)/mCP: 10% S-BN-CF (20 nm)/BmPyPB (10 nm)/BmPyPB: 8% Liq (40 nm)/Liq (1.5 nm)/Al; Device B: ITO/HATCN (20 nm)/ TAPC: HATCN (5: 2, 60 nm)/TCTA (20 nm)/mCBP: 10% S-BN-CCB (20 nm)/BmPyPB (10 nm)/BmPyPB: 8% Liq (40 nm)/Liq (2 nm)/Al; Device C: ITO/HATCN (10 nm)/ TAPC: HATCN (5: 2, 60 nm)/TCTA (20 nm)/mCP: 10% S-BN-DCB (20 nm)/BmPyPB (10 nm)/BmPyPB: 8% Liq (40 nm)/Liq (1.5 nm)/Al; Device D: ITO/HATCN (10 nm)/ TAPC: HATCN (5: 2, 60 nm)/TCTA (20 nm)/mCP: 10% S-BN-AF (20 nm)/BmPyPB (10 nm)/BmPyPB: 8% Liq (40 nm)/Liq (1.5 nm)/Al; Device E: ITO/HATCN (10 nm)/ TAPC (60 nm)/mCP (10 nm)/S-BN-CF (20 nm)/BmPyPB (50 nm)/Liq (2.5 nm)/Al; Device F: ITO/HATCN (5 nm)/ TAPC (50 nm)/TCTA (5 nm)/S-BN-CCB (20 nm)/Bphen (50 nm)/Liq (2 nm)/Al; Device G: ITO/HATCN (20 nm)/ TAPC (60 nm)/TCTA (20 nm)/S-BN-DCB (20 nm)/ BmPyPB (40 nm)/Liq (2.5 nm)/Al; Device H: ITO/HATCN (5 nm)/TAPC (50 nm)/TCTA (5 nm)/S-BN-AF (20 nm)/ Bphen (50 nm)/Liq (2 nm)/Al.

FIG. 15 depicts normalized emission spectra of S-BN-CF (A), S-BN-CCB (B), S-BN-DCB (C) and S-BN-AF (D) in different solvents (concentration: 1×$10^{-5}$ M).

and S-BN-AF F) in THF/H$_2$O mixtures with different amounts of water (f$_w$=0%-99%). Insert: Fluorescence photographs of S-BN-CF (D), S-BN-DCB (E) and S-BN-AF (F) in THF/H$_2$O mixtures (up picture; f$_w$=0%, 60%, 99%), solid powder under 365 nm UV irradiation at room temperature (lower picture). Conditions: the concentrations of S-BN-CCB, S-BN-DCB and S-BN-AF are 10 μmol L$^{-1}$. The excitation wavelengths of S-BN-CCB, S-BN-DCB and S-BN-AF are 420, 440, 450 nm.

Figure 18:
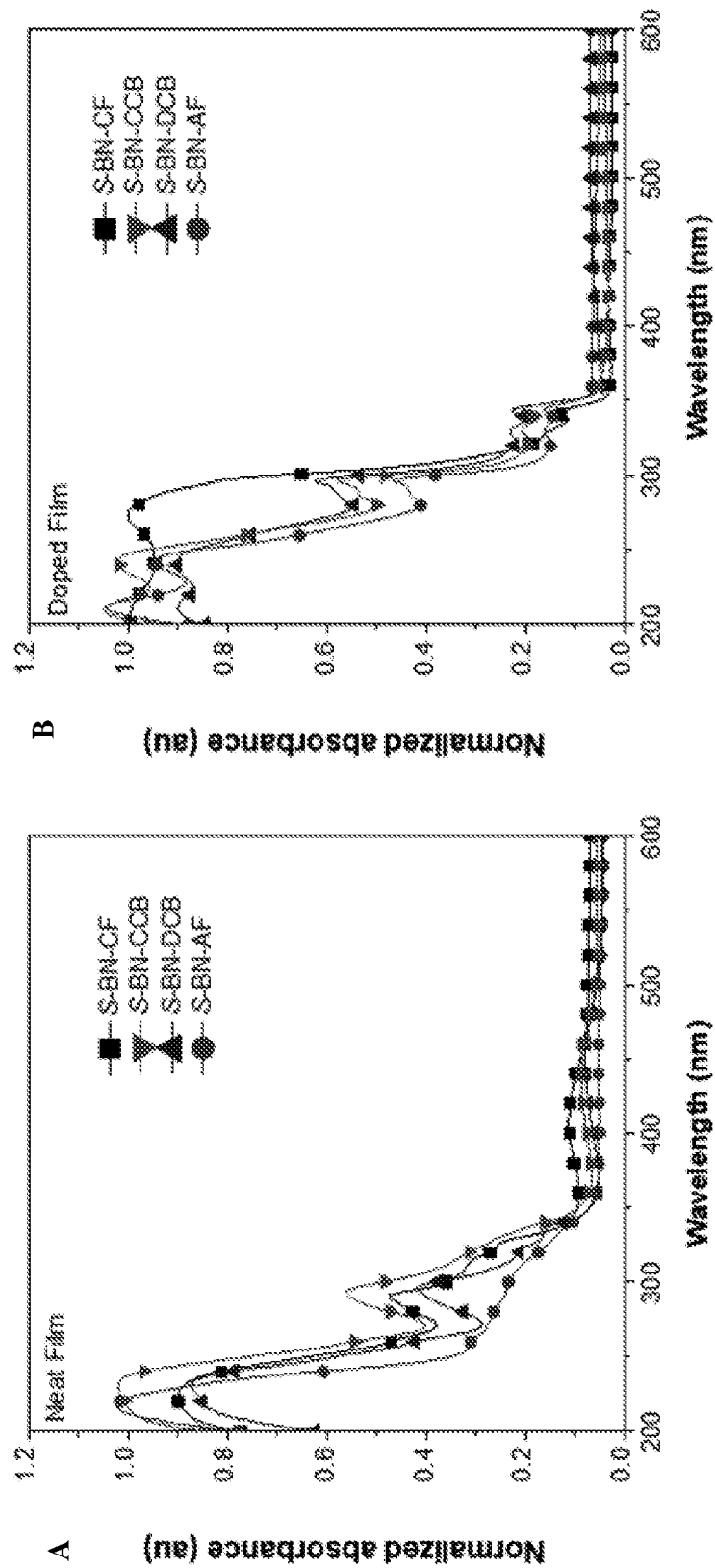

FIG. 18 depicts UV-Vis absorption of S-BN-CF, S-BN-CCB, S-BN-DCB and S-BN-AF in neat film (A) and doped film (B) at room temperature.

Figure 19:
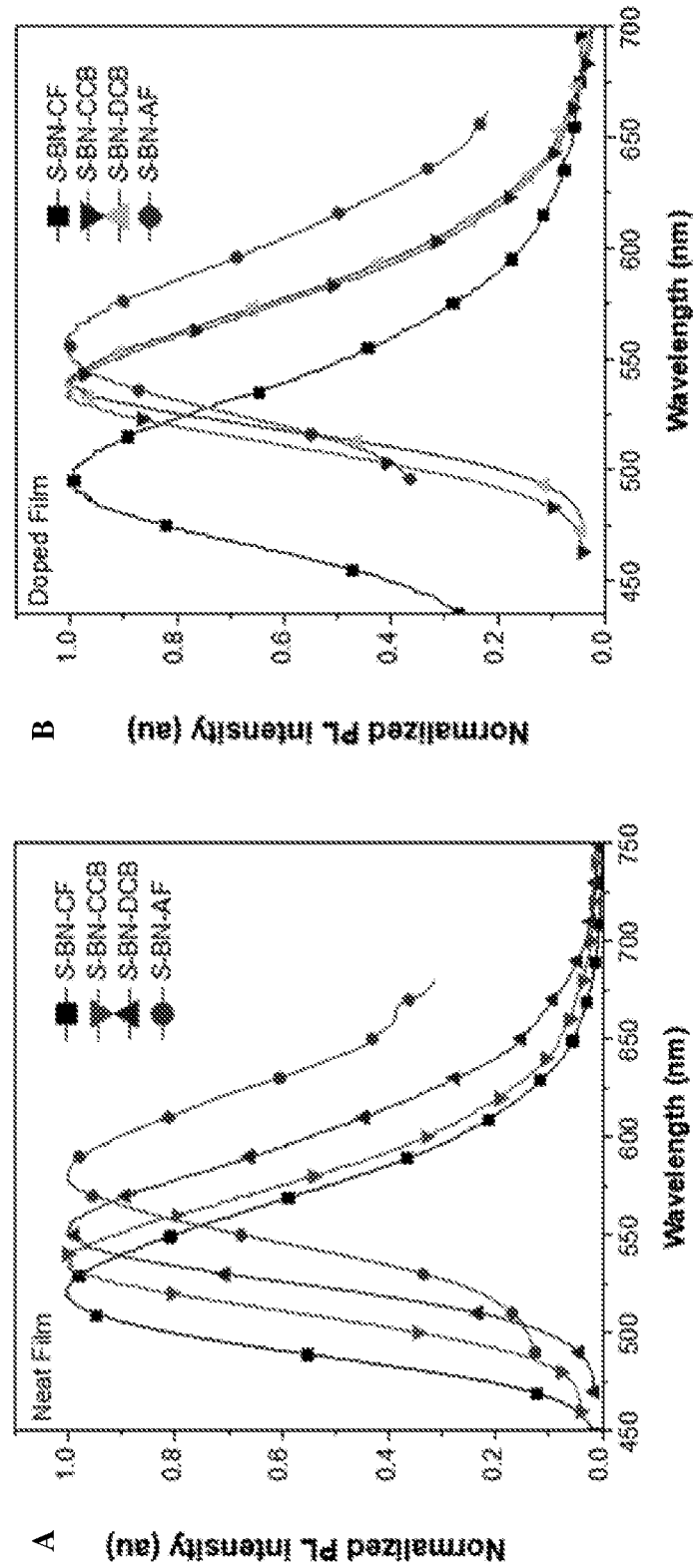

FIG. 19 depicts photoluminescence (PL) spectra of S-BN-CF, S-BN-CCB, S-BN-DCB and S-BN-AF in neat film (A) and doped film (B) at room temperature.

FIG. 20 depicts Table 3, which shows transient PL decay data of toluene solutions (1×10$^{-4}$ mol/L), neat films and doped films in mCP (10% w) of S-BN-CF, S-BN-CCB, S-BN-DCB and S-BN-AF at 300 K at ambient conditions. The transient PL decay data were fitted by multiple-exponential function and the mean fluorescence lifetimes (<τ>) were calculated by <τ>=τ$_i$A$_i$τ$_i^2$/ΣA$_i$τ$_i$, where A$_i$ is the pre-exponential for lifetime τ$_i$. R$_{prompt}$ and R$_{delayed}$ are individual component ratio for prompt and delayed fluorescence. R$_{prompt}$=τ$_i$A$_1$/ΣA$_i$τ$_i$, R$_{delayed}$=1-R$_{prompt}$.

FIG. 21 depicts Table 4 which shows photophysical data of neat films and doped films in mCP (10% w) of S-BN-CF, S-BN-CCB, S-BN-DCB and S-BN-AF a) Abbreviations: Φ$_{PL}$=absolute photoluminescence quantum yield; τ$_{prompt}$ and τ$_{delayed}$=lifetimes calculated from the prompt and delayed fluorescence decay, respectively; R$_{delayed}$=the ratio of delayed components; Φ$_{prompt}$ and Φ$_{delayed}$=fluorescent and delayed components, respectively, determined from the total Φ$_{PL}$ and the proportion of the integrated area of each of the components in the transient spectra to the total integrated area; Φ$_{ISC}$=the intersystem crossing quantum yield; k$_F$=fluorescence decay rate; k$_{IC}$=internal conversion decay rate from S$_1$ to S$_0$; k$_{ISC}$=intersystem crossing decay rate from S$_1$ to T$_1$; k$_{RISC}$=the rate constant of reverse intersystem crossing process.

Figure 22:
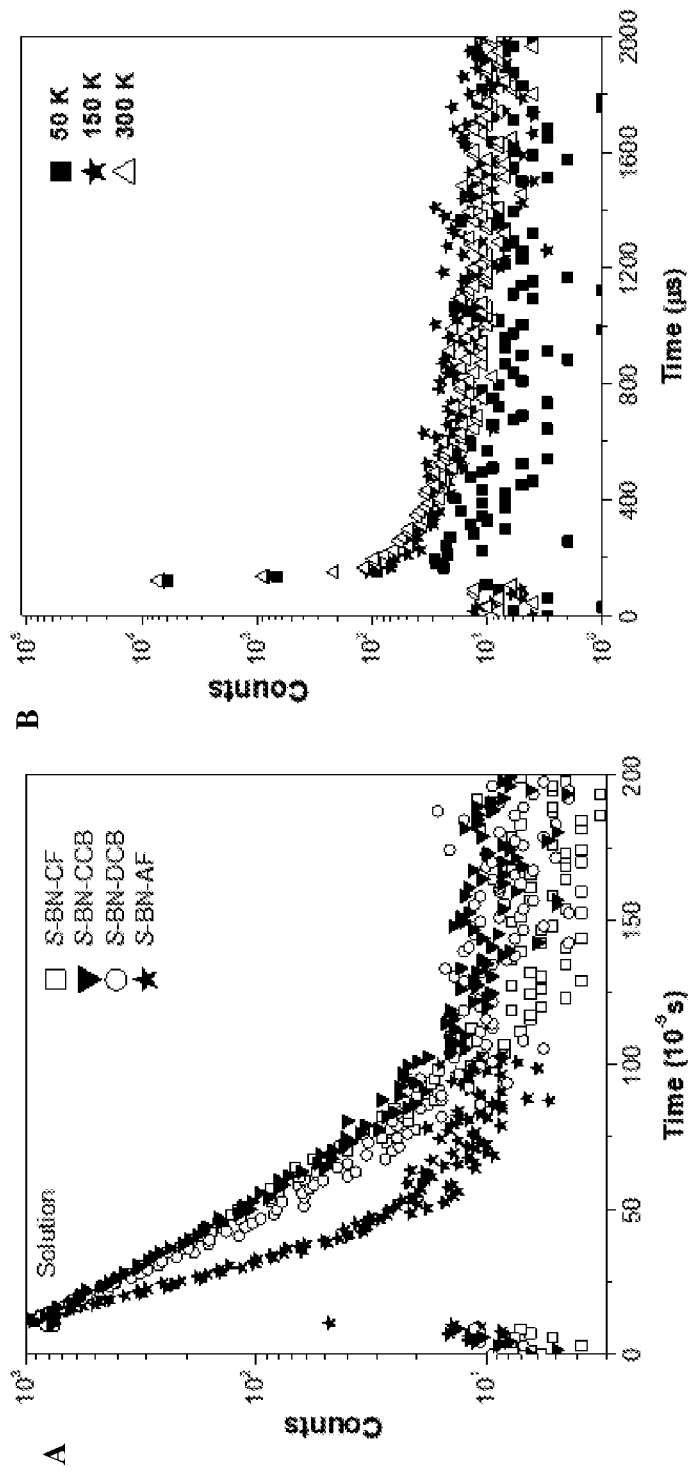

FIG. 22 depicts (A) Transient decay spectra of S-BN-CF, S-BN-CCB, S-BN-DCB and S-BN-AF in toluene solution (A, 1×10$^{-4}$ mol/L). (B) The temperature dependent transient PL decay spectra of S-BL-CF in doped film (10 wt % in mCP) from 50K to 300K.

Figure 5:
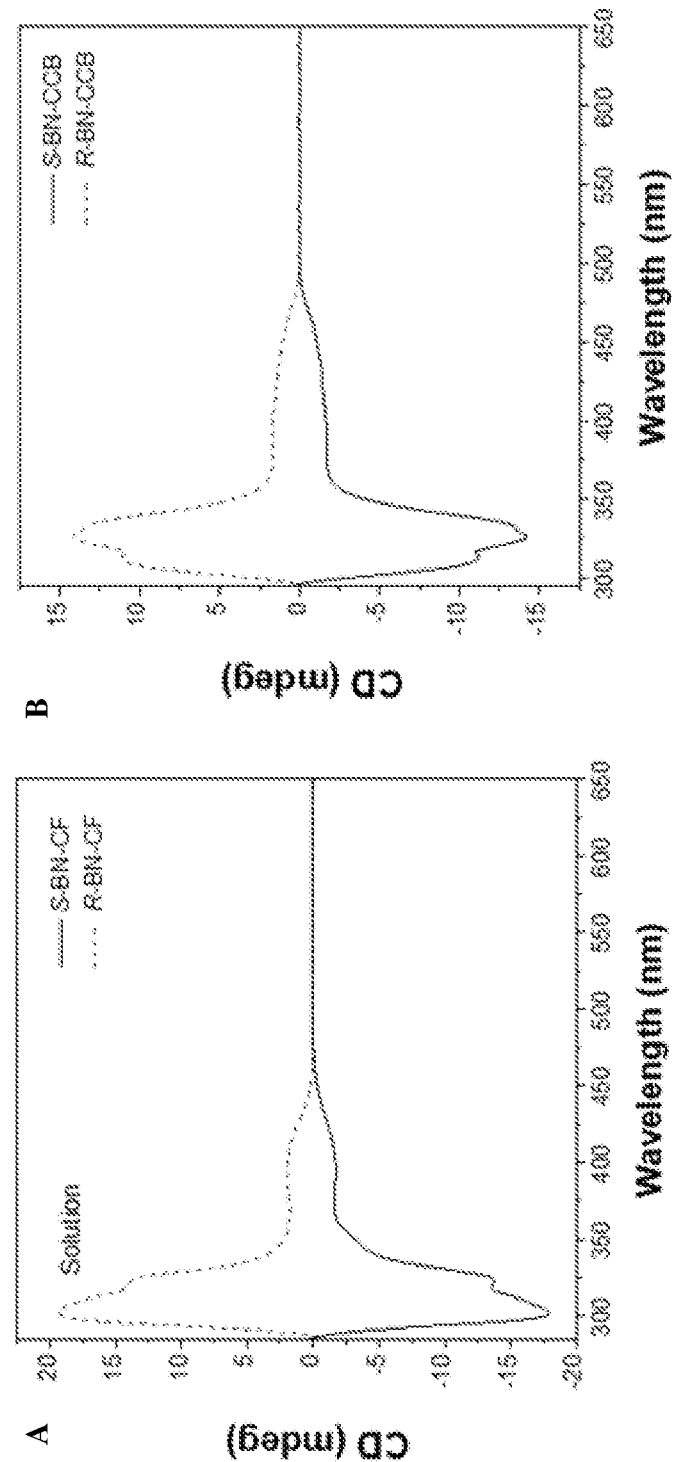
FIG. 5 depicts CD spectra of (A) R/S-BN-CF, (B) R/S-BN-CCB, (C) R/S-BN-DCB and (D) R/S-BN-AF in toluene (5.0×$10^{-5}$ mol/L) and (E) R/S-BN-CF, (F) R/S-BN-CCB, (G) R/S-BN-DCB and (H) R/S-BN-AF in neat film.
Figure 5:
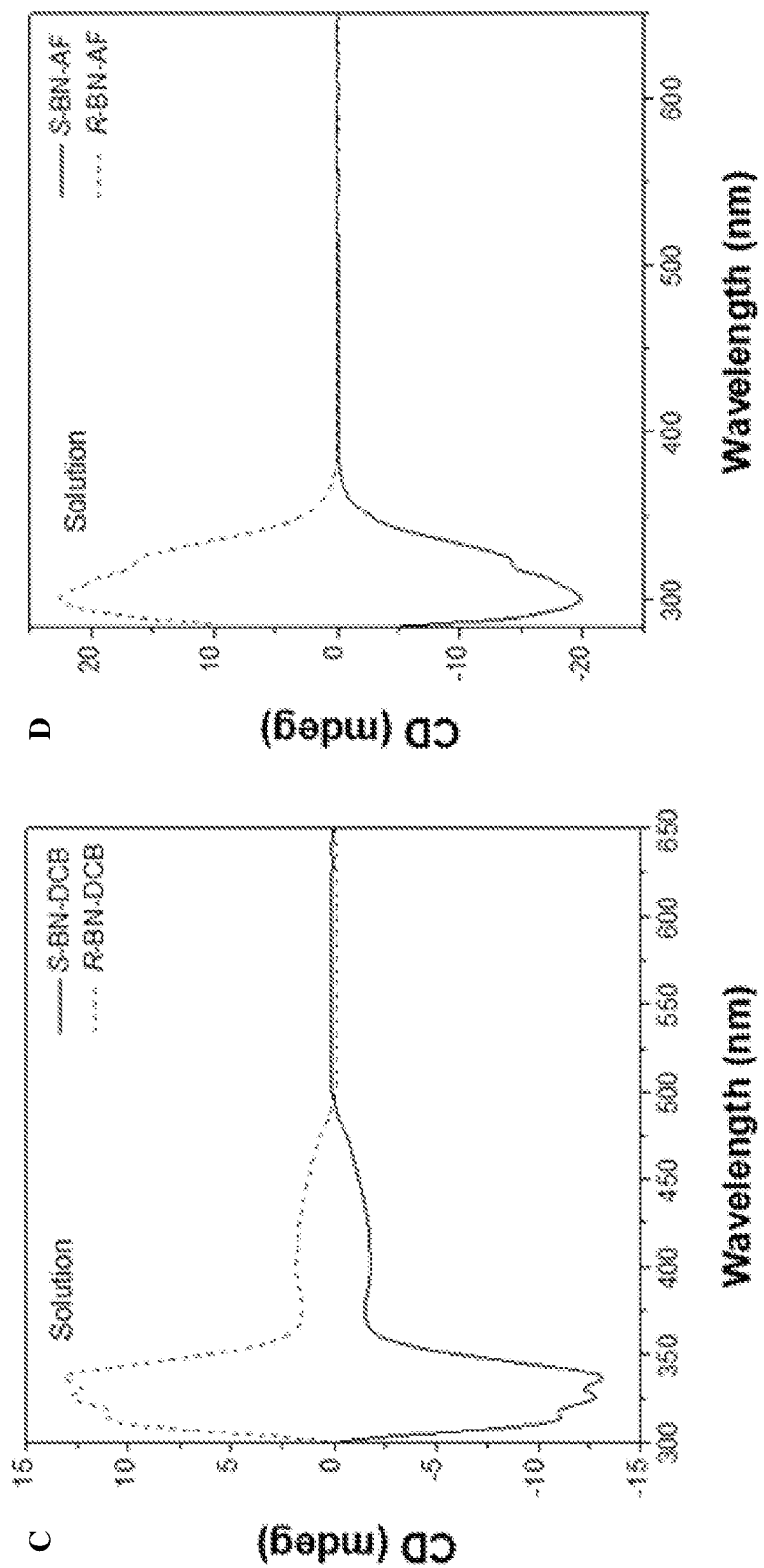
Figure 5:
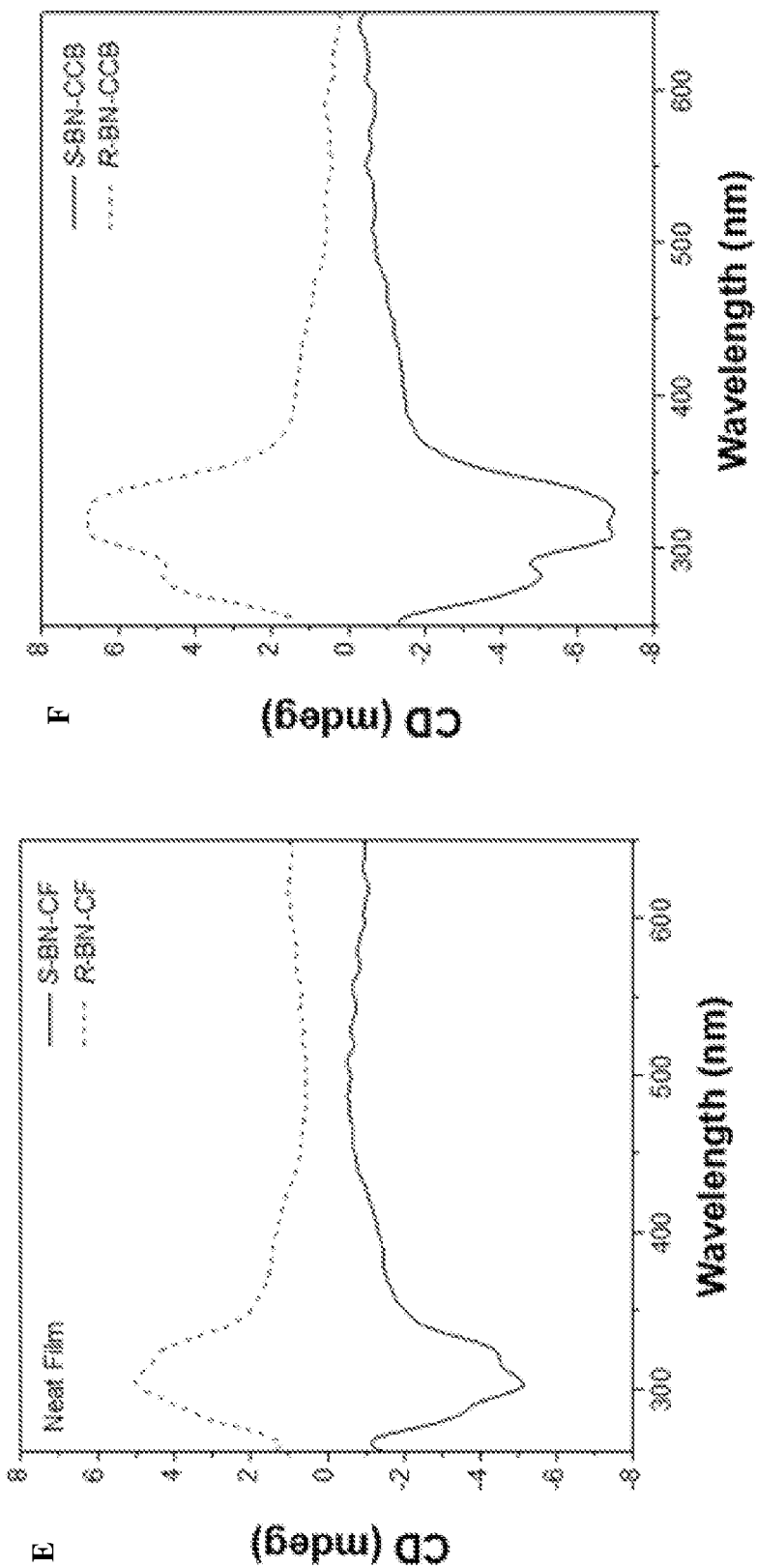
Figure 23:
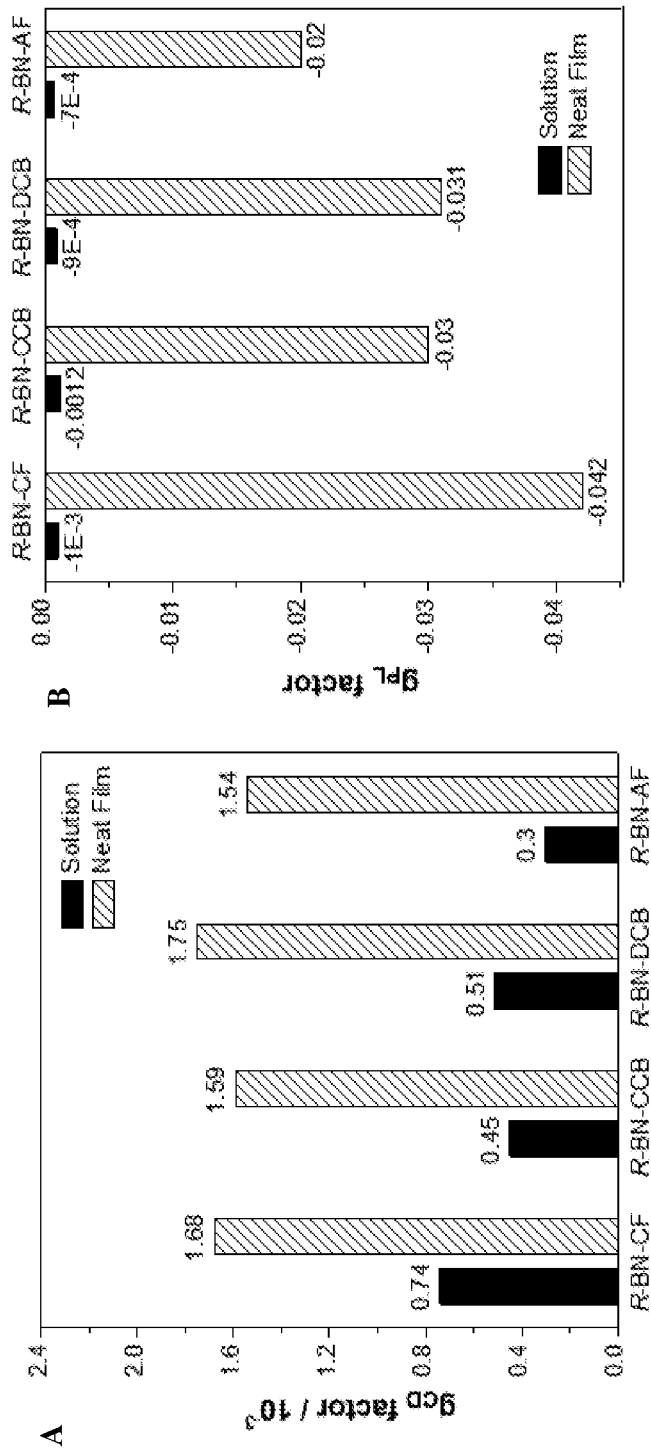

FIG. 23 depicts g$_{CD}$ of R-BN (A) and S-BN (B) in solution of toluene and in neat film. The g$_{CD}$ values were calculated from FIGS. 5A and 5B at the adsorption wavelength of 405, 436, 440 and 450 nm for R/S-BN-CF, R/S-BN-CCB, R/S-BN-DCB and R/S-BN-AF.

Figure 24:
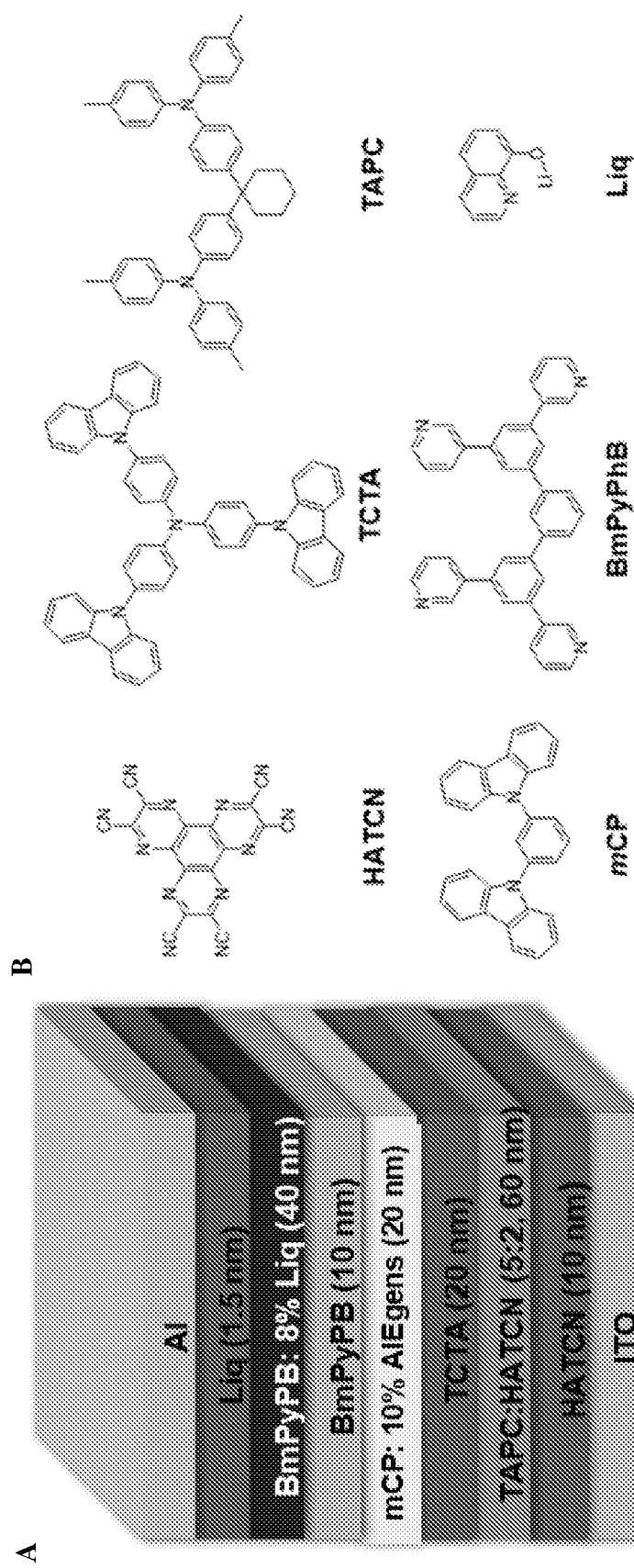

FIG. 24 depicts (A) an exemplary electroluminescent device configuration of comprising a compound described herein. (B) Chemical structures of adopted materials.

Figure 25:
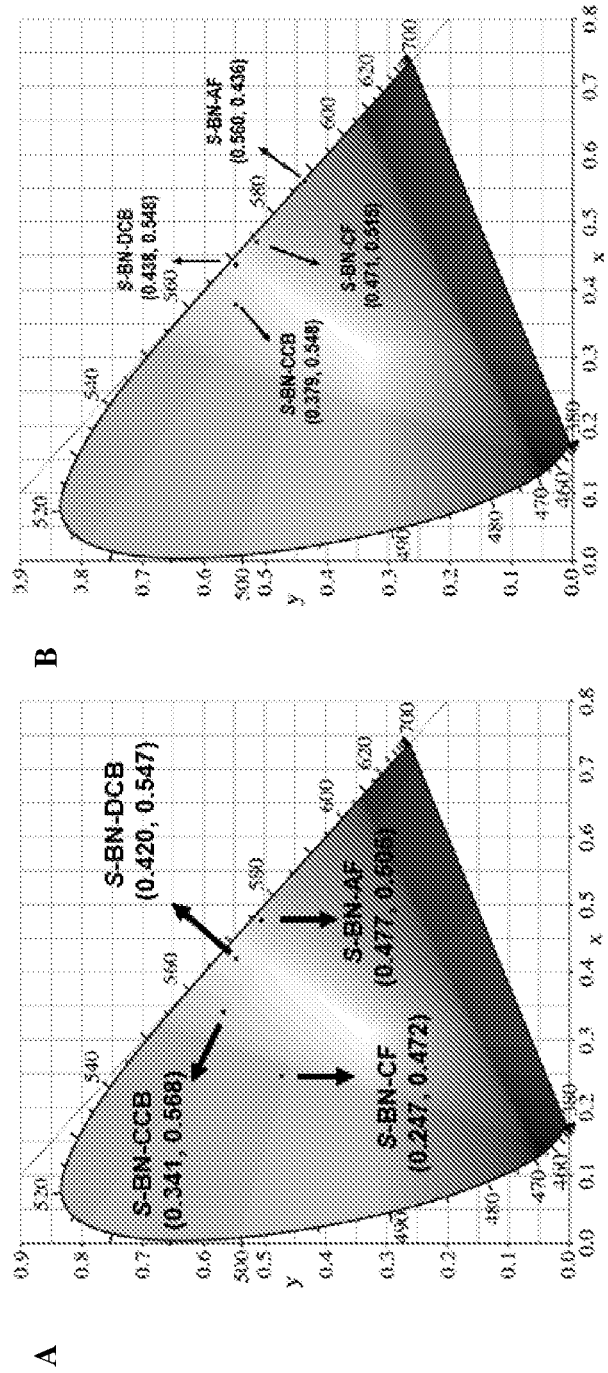

FIG. 25 depicts EL color coordinates on the CIE 1931 chromaticity diagram for doped film (A) and neat film (B).

Figure 26:
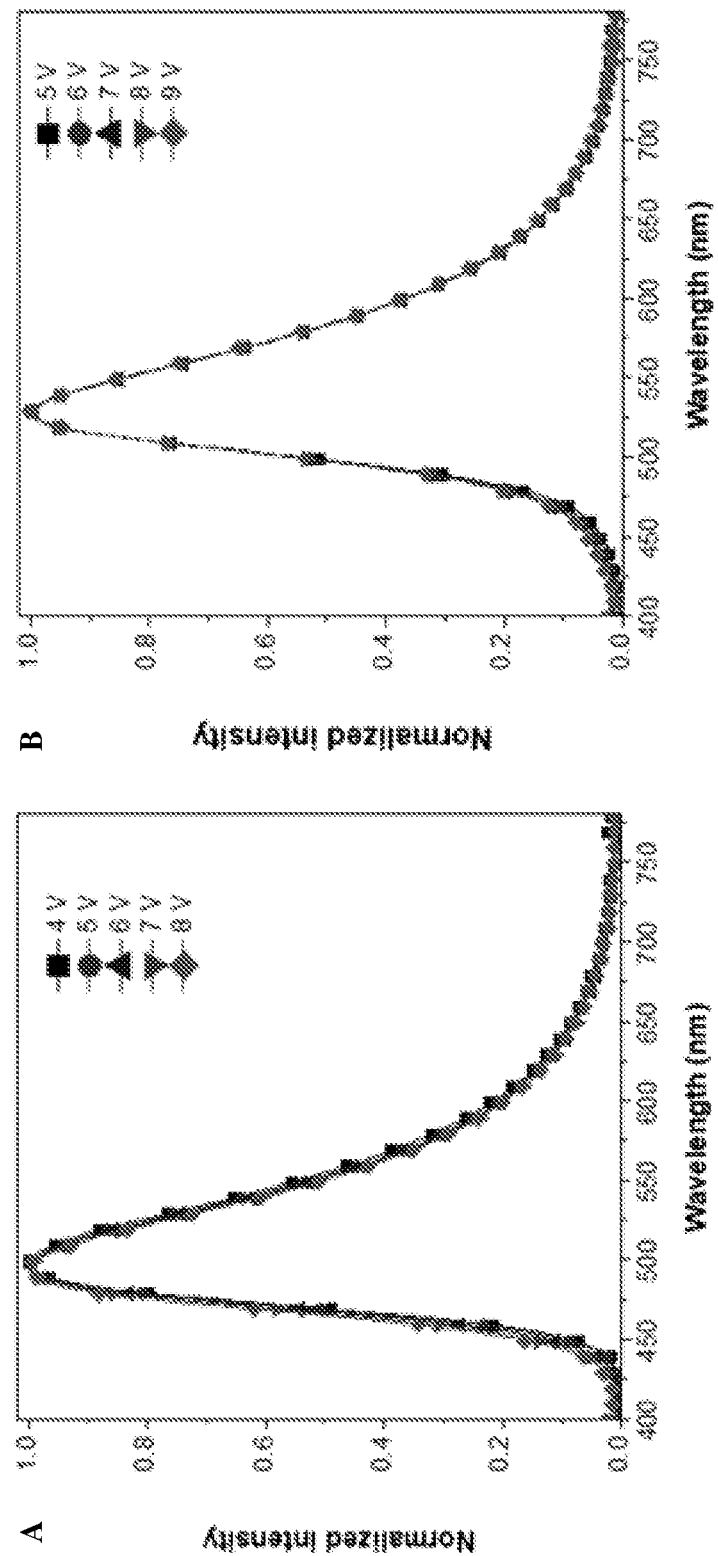
Figure 26:
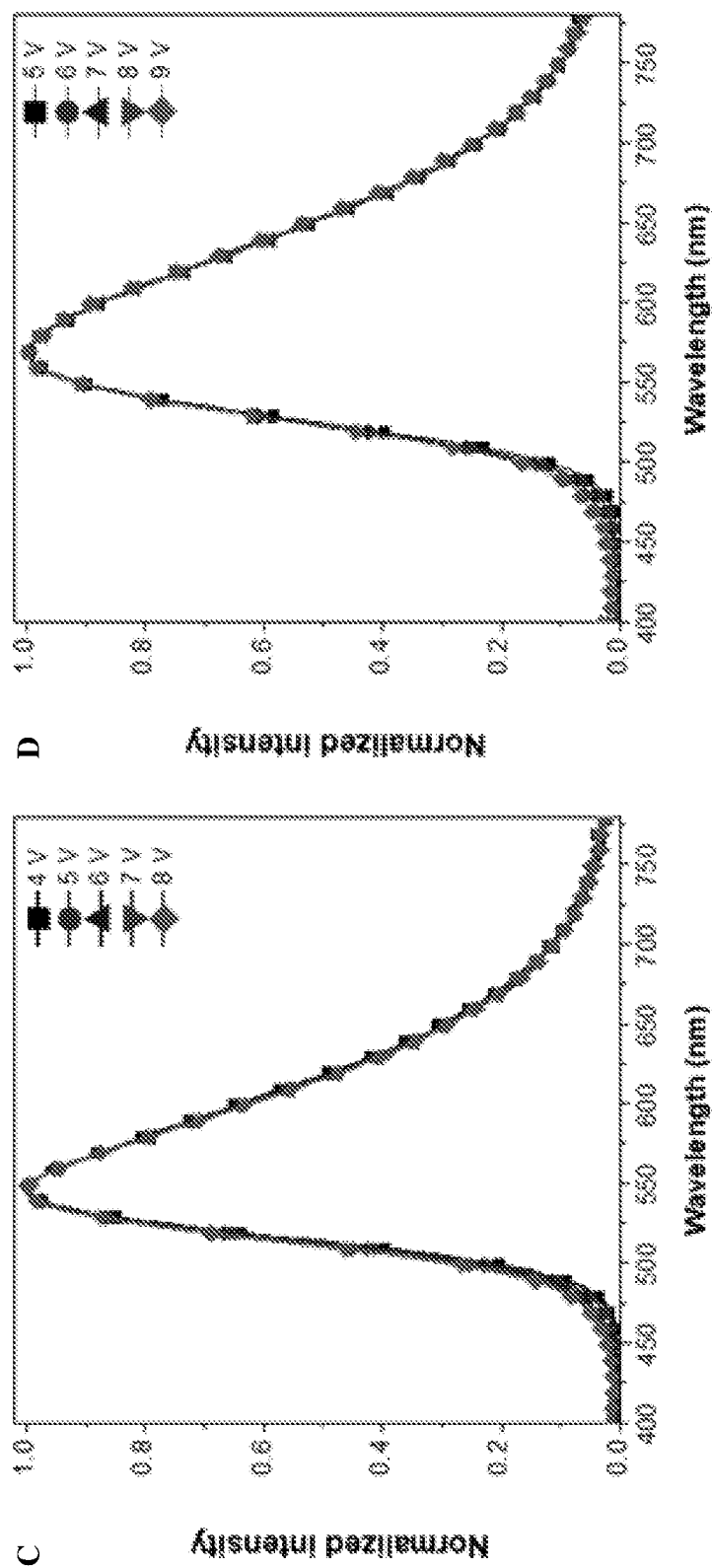

FIG. 26 depicts EL spectra of doped film for S-BN-CF (A), S-BN-CCB (B), S-BN-DCB (C) and S-BN-AF (D) taken at various voltage from 4 V to 9 V.

Figure 27:
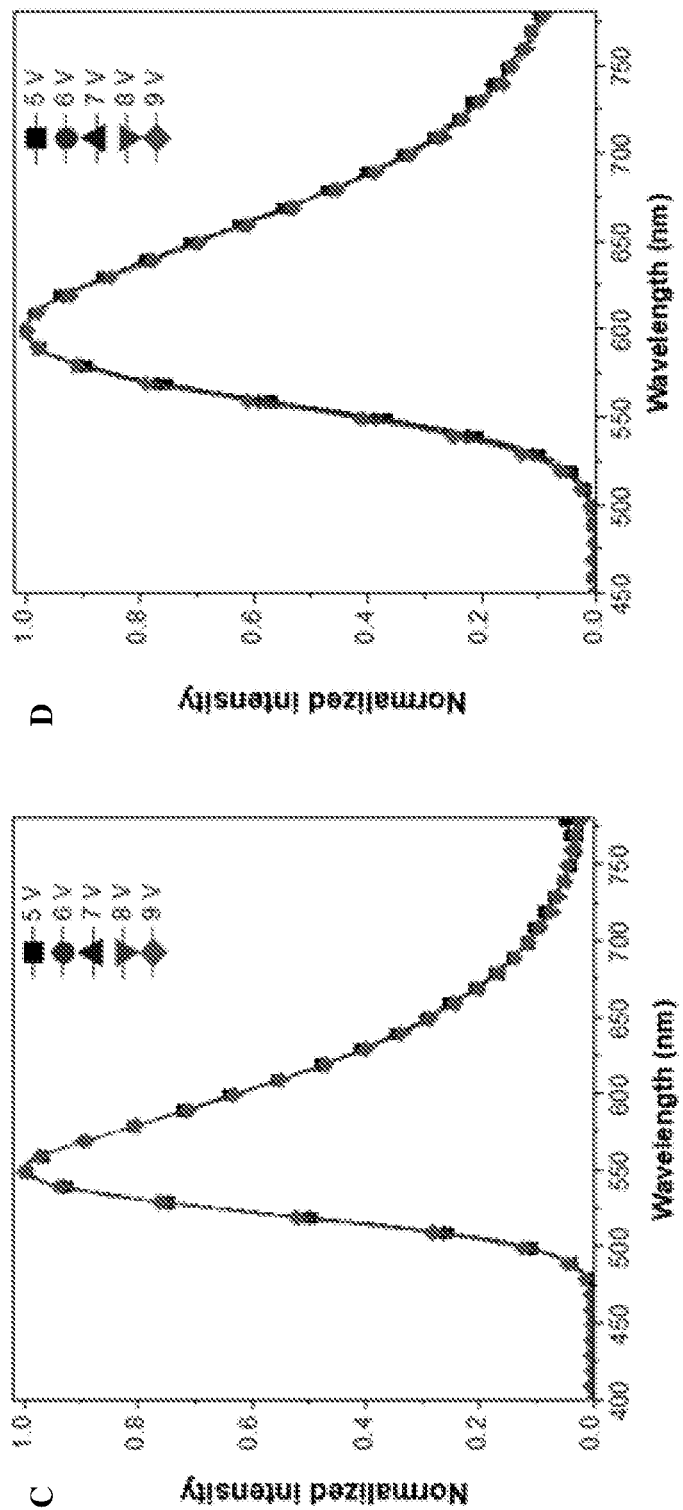

FIG. 27 depicts EL spectra of non-doped film for S-BN-CF (A), S-BN-CCB (B), S-BN-DCB (C) and S-BN-AF (D) taken at various voltage from 5 V to 9 V.

Figure 28:
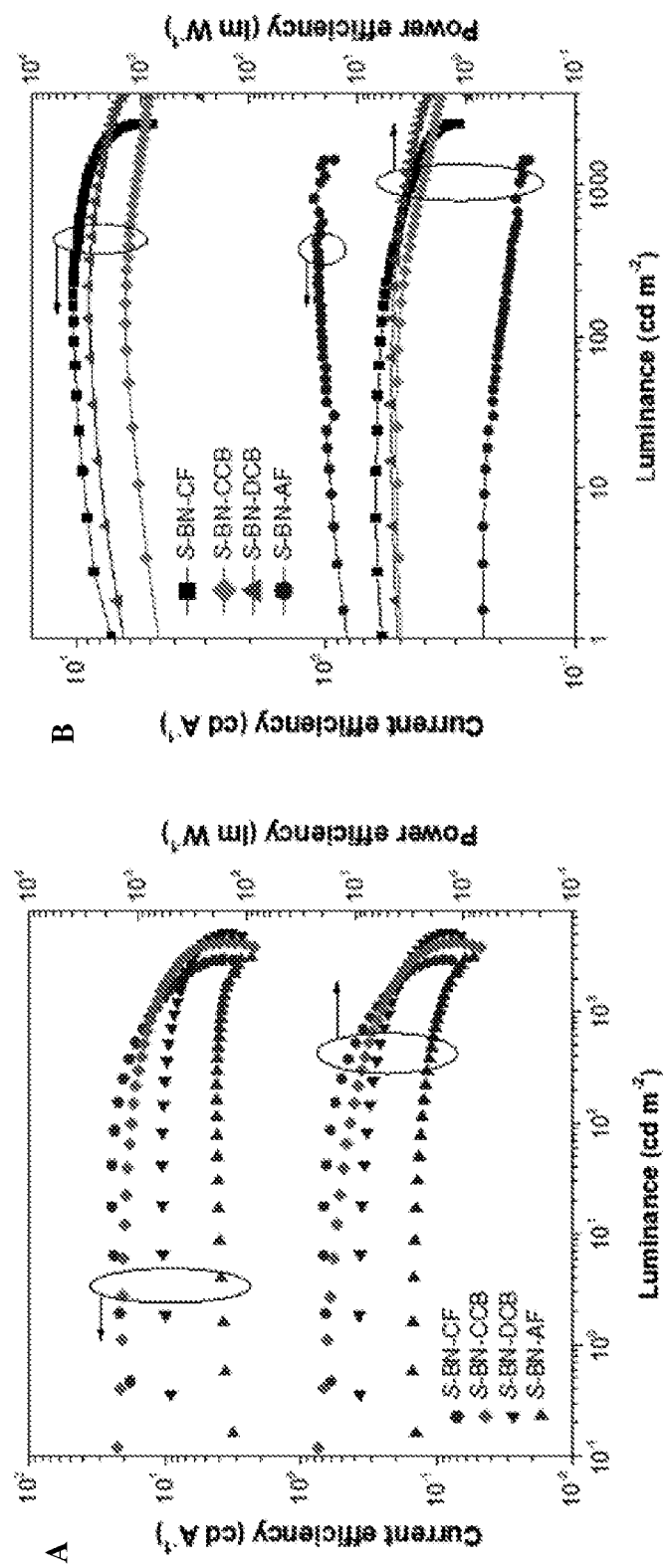

FIG. 28 depicts current efficiency-luminance-power efficiency characteristics of (A) the doped devices and (B) neat devices.

Figure 29:
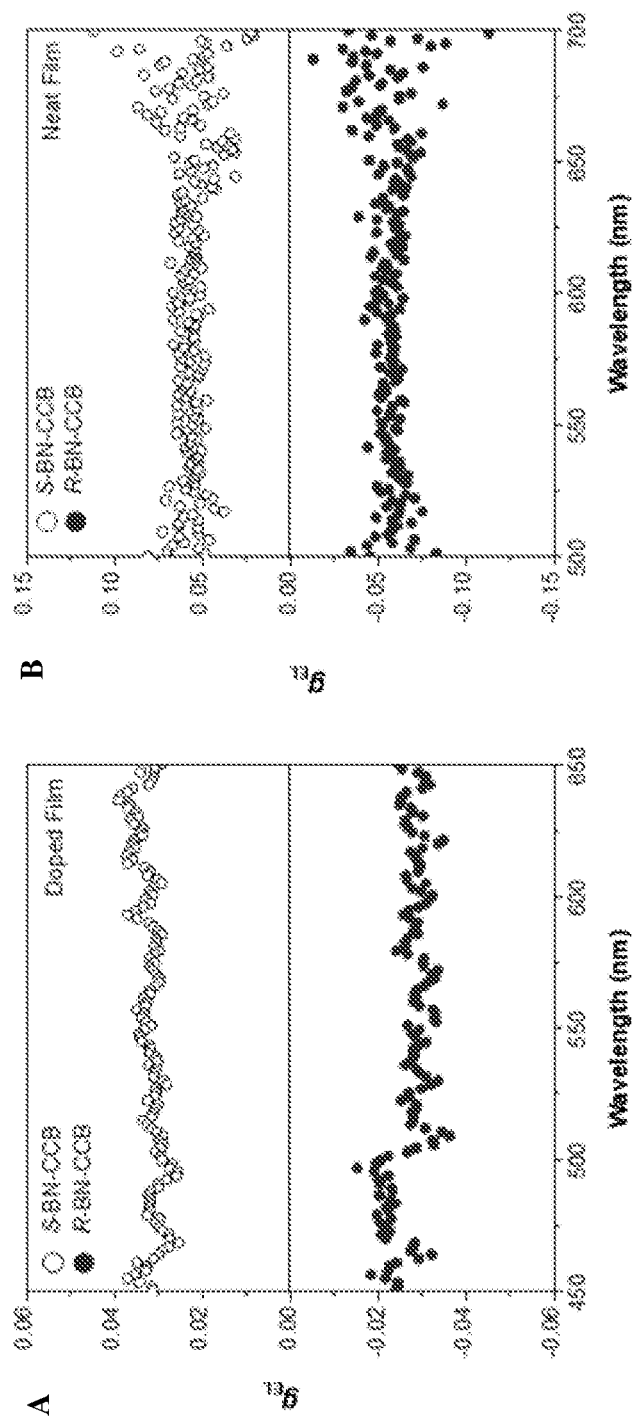
Figure 29:
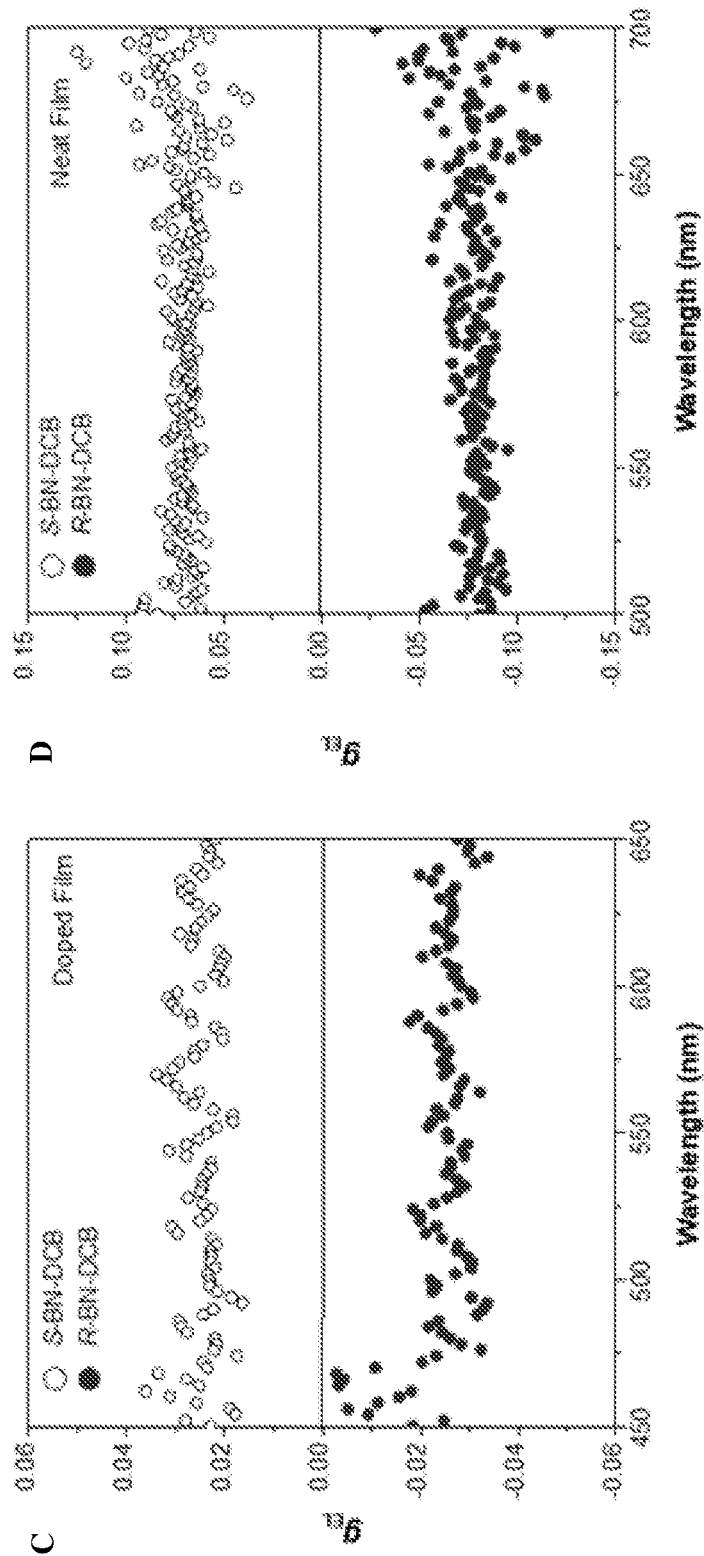
Figure 29:
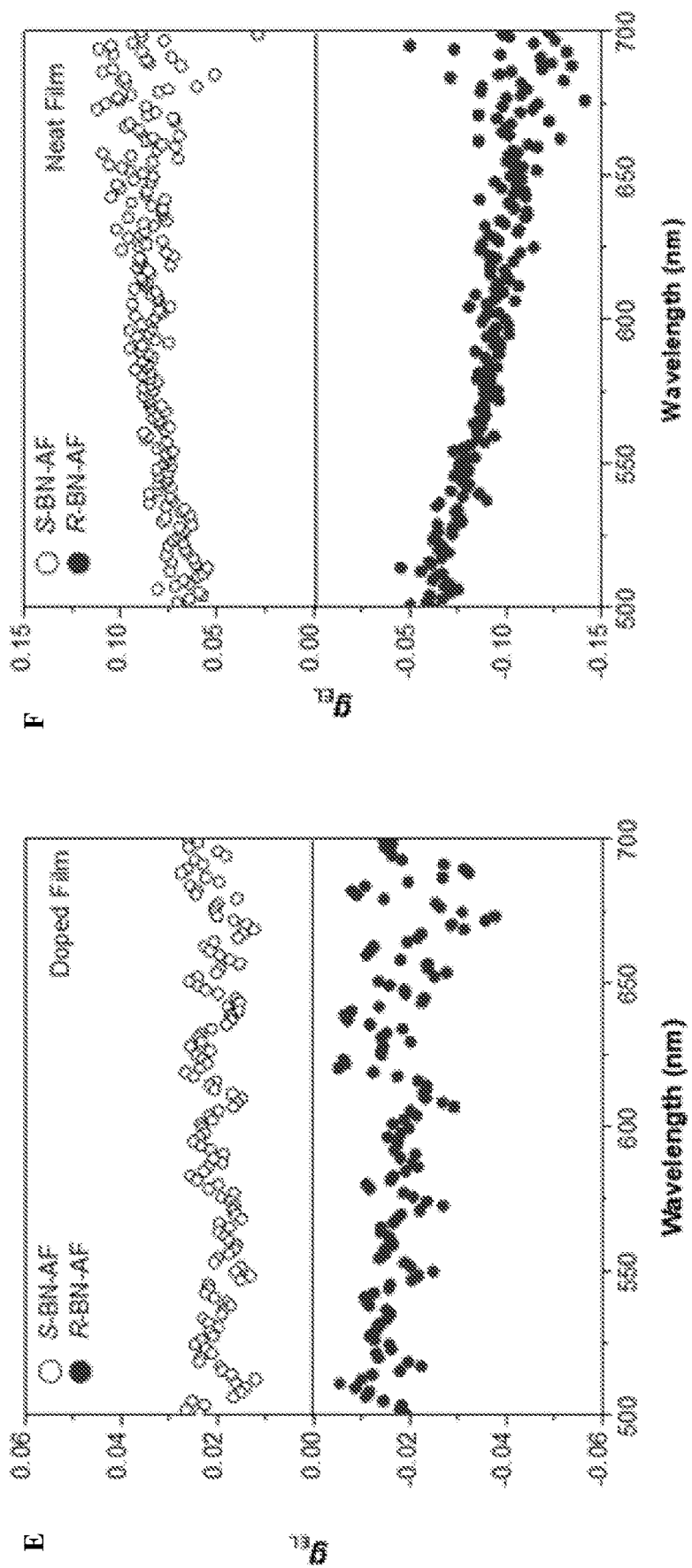

FIG. 29 depicts g$_{EL}$ of R/S-BN-CCB (A), R/S-BN-DCB (C) and R/S-BN-AF (E) as a function of emission wavelength in doped film. g$_{EL}$ of R/S-BN-CCB (B), R/S-BN-DCB (D) and R/S-BN-AF (F) as a function of emission wavelength in neat film.

Figure 30:
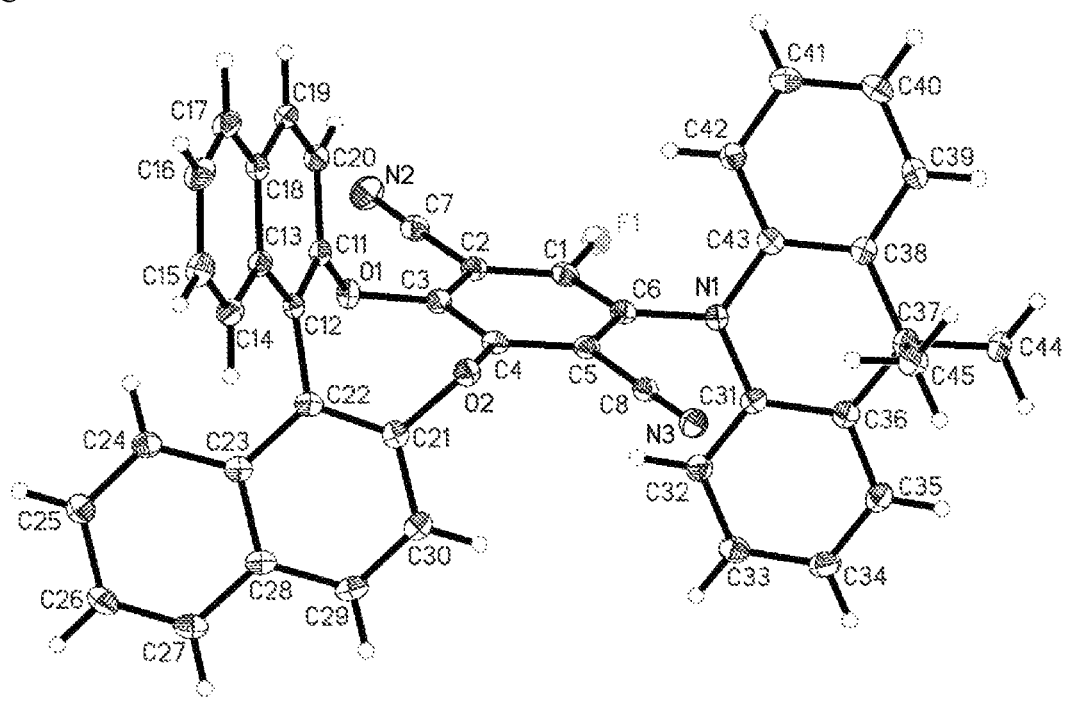

FIG. 30 depicts an ORTEP drawing of single-crystal X-ray structures of R-BN-CF (A), S-BN-DCB (B), and S-BN-AF (C). Solvents in (A) and (B) are omitted for clarity. Thermal ellipsoids are scaled to the 50% probability level.

FIG. 31 depicts Table 5, which shows comparison of the CPOLED devices performances of this work and all of reported CPOLEDs reported so far.

Figure 32:
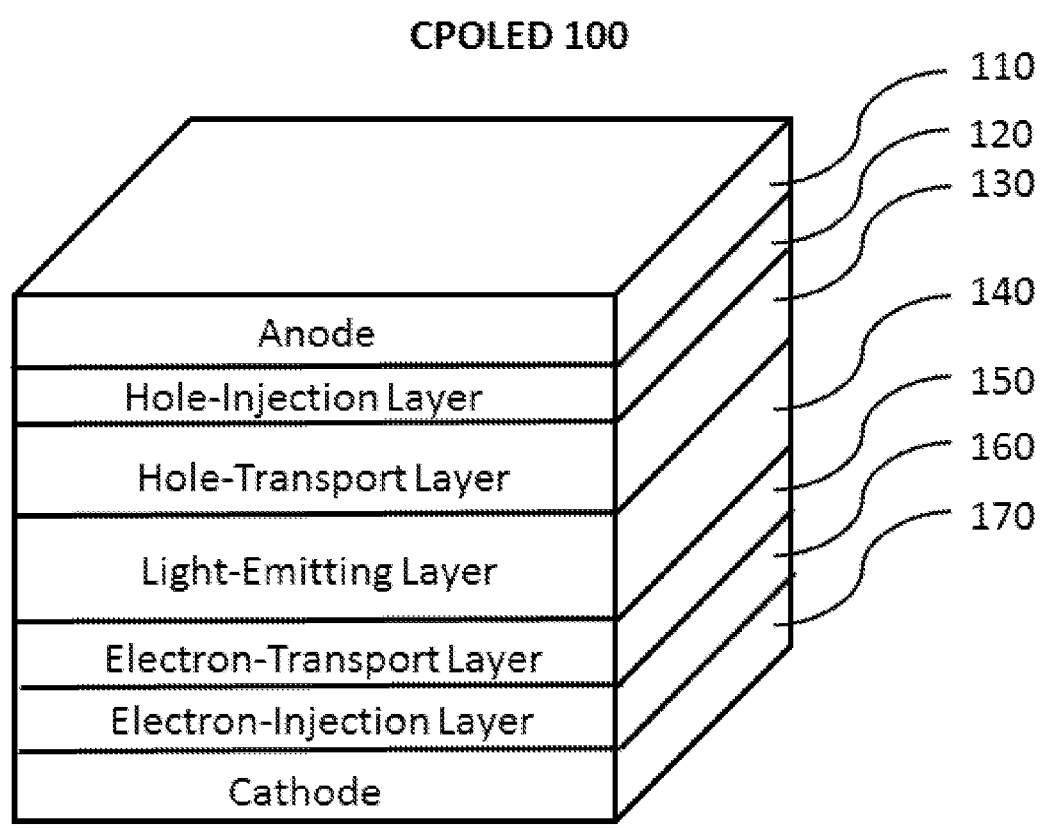

FIG. 32 depicts an exemplary CPOLED according to certain embodiments described herein. The figures are not necessarily drawn to scale.

DETAILED DESCRIPTION

Definitions

The definitions of terms used herein are meant to incorporate the present state-of-the-art definitions recognized for each term in the chemical and semiconductor fields. Where appropriate, exemplification is provided. The definitions apply to the terms as they are used throughout this specification, unless otherwise limited in specific instances, either individually or as part of a larger group.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C$_1$-C$_{30}$ for straight chain, C$_3$-C$_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" and "sulfone" is art-recognized and refers to —SO$_2$-. "Halide" designates the corresponding anion of the halogens.

The representation "⁓" as used herein in connection to chemical a group or moiety is intended to represent the covalent bond that the aforementioned chemical group or moiety is covalently bonded to another chemical group or moiety.

The phrase "aggregation-induced emission" or "AIE" as used herein refers to the enhancement of light-emission by a fluorescent compound upon aggregation in the amorphous or crystalline (solid) states of the fluorescent compound, whereas the fluorescent compound exhibits weak or substantially no emission in dilute solutions.

The term "$\lambda_{ex}$" as used herein refers to the excitation wavelength.

The term "$\lambda_{em}$" as used herein refers to the emission wavelength.

As used herein, "isolated" means that the compounds described herein are separated from other components of a synthetic organic chemical reaction mixture. The compounds described herein can be purified via conventional techniques. As used herein, "purified" means that when isolated, the isolate contains at least 95%, at least 98%, or more of a compound described herein by weight of the isolate.

"Enantiomers" are a pair of stereoisomers that are non-superimposable mirror images of each other. A mixture of a pair of enantiomers in equal proportions can be known as a "racemic" mixture. The term "(+/−)" is used to designate a racemic mixture where appropriate. The absolute stereochemistry can be specified according to the Cahn-Ingold-Prelog R-S system. When a compound is an enantiomer, the stereochemistry at each chiral carbon and/or axis of chirality can be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein can contain one or more asymmetric centers and/or axis of chirality and can thus give rise to enantiomers, diastereomers, and other stereoisomeric forms that can be defined, in terms of absolute stereochemistry at each asymmetric atom or axis of chirality, as (R)- or (S)-. The present compounds and methods are meant to include all such possible isomers, including substantially enantiopure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer. ee=(90−10)/100=80%.

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, about 99%, or greater of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40%, about 50%, about 75%, about 90%, about 95%, about 99%, or greater of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure", "substantially enantiopure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers), such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R) isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

The compounds described herein can exhibit a number of beneficial properties, such as CPEL, CPL, AIE, TICT and TADF, which makes them useful materials for the development of improved electroluminescent devices and fluorescent probes. In certain embodiments, the compound has the Formula I:

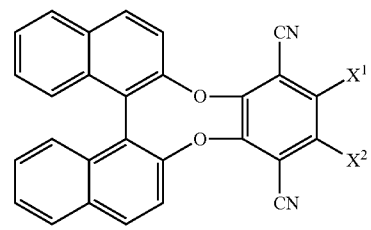

I wherein each of $X^1$ and $X^2$ is independently selected from the group consisting of:

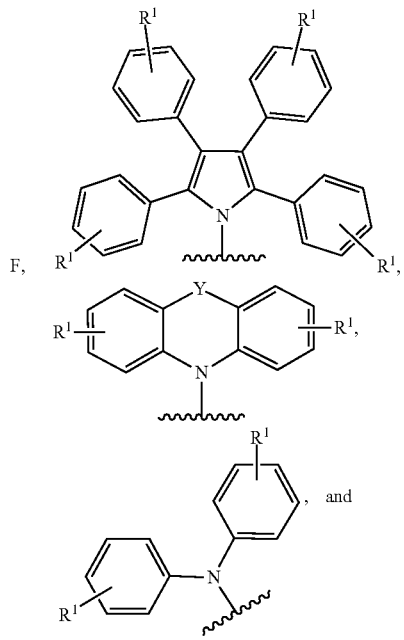

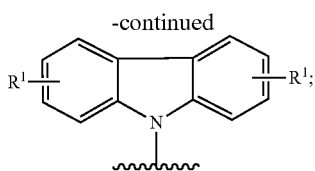

$R^1$ for each instance is independently selected from the group consisting of halide, H, alkyl, alkene, alkyne, heteroalkyl, cycloalkyl, heterocycloalkyl, aryl, heteroaryl, carboxyl, —$NR_2$, sulfonic acid, —SR, and —OR;

Y is —N(R)—, O, S, Se, Te, or —$C(R)_2$—;

wherein at least one $R^1$ optionally further comprises a terminal functional group selected from the group consisting of $N_3$, NCS, SH, $NH_2$, COOH, alkyne, N-hydroxysuccinimide ester, maleimide, hydrazide, nitrone group, —CHO, OH, halide, and charged ionic group; and R for each instance is independently selected from the group consisting of H, alkyl, cycloalkyl, aryl, and heteroaryl, with the proviso that if $X^1$ is N-carbazole, then $X^2$ is not N-carbazole and if $X^1$ is F, then $X^2$ is not F.

In certain embodiments, the compound of Formula I specifically excludes compounds of Formula I, wherein $X^1$ is N-carbazole and $X^2$ is N-carbazole; and/or $X^1$ is F and $X^2$ is F, as shown below.

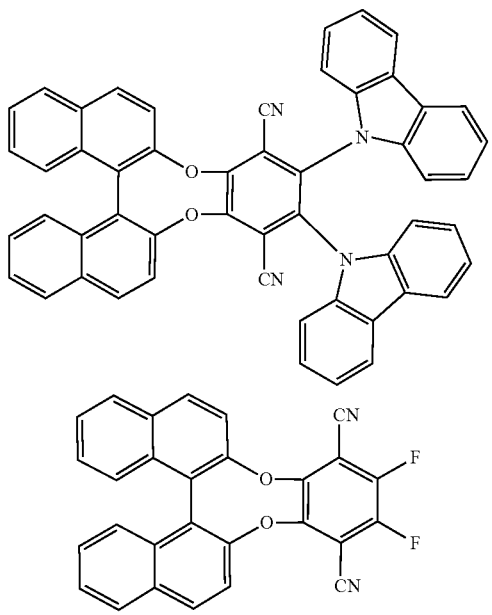

In certain embodiments of the compound of Formula I, wherein $X^1$ is N-carbazole and $X^2$ is F, the compound is present in isolated and/or pure form and/or exists as a thin film.

The compound of Formula I comprises a binaphthol moiety, which has an axis of chirality and consequently can exist as two non-superimposable mirror images. In certain embodiments, the compound of Formula I is substantially enantiopure and has an enantiomeric excess of the R enantiomer or the S enantiomer. In certain embodiments, the enantiomeric excess of the compound of Formula I is at least 30%, 40%, 50%, 60%, 70%, 80%, 85%, 90%, 93%, 95%, 97%, 98%, 99%, 99.5%, 99.9%, or greater.

In certain embodiments, the compound of Formula I is present in the solid state, e.g., in a thin film. In certain embodiments, the compound of Formula I is present is the dopant in a host matrix.

Y can be —N(R)—, O, S, Se, Te, or —$C(R)_2$—, wherein R is H, alkyl, or cycloalkyl. In certain embodiments, Y is N(R)—, O, S, or —$C(R)_2$—, wherein R is H, $C_1$-$C_{10}$ alkyl, or $C_3$-$C_7$ cycloalkyl. In certain embodiments, Y is —$C(R)_2$—, wherein R is H, $C_1$-$C_{10}$ alkyl, $C_1$-$C_8$ alkyl, $C_1$-$C_6$ alkyl, $C_3$-$C_6$ cycloalkyl, or $C_5$-$C_6$ cycloalkyl. In certain embodiments, Y is —$C(R)_2$—, wherein R is H or $C_1$-$C_6$ alkyl.

With reference to $X^1$ and $X^2$, the covalent bond between $R^1$ and the aryl to which it is attached is intended to indicate that $R^1$ can be covalently bonded to any position on the aryl ring, valency permitting. For example, $R^1$ can be covalently bound to any of positions 1-8 of the following exemplary N-carbazole:

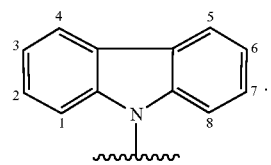

$R^1$ for each instance can independently be fluoride, chloride, bromide, H, $C_1$-$C_{10}$ alkyl, $C_2$-$C_{10}$ alkene, $C_2$-$C_{10}$ alkyne, heteroalkyl, $C_3$-$C_7$ cycloalkyl, heterocycloalkyl, optionally substituted aryl, heteroaryl, carboxyl, —$NR_2$, sulfonic acid, —SR, or —OR. In certain embodiments, $R^1$ for each instance is independently fluoride, H, $C_1$-$C_{10}$ alkyl, $C_1$-$C_8$ alkyl, $C_1$-$C_6$ alkyl, $C_3$-$C_7$ cycloalkyl, $C_5$-$C_6$ cycloalkyl, heterocycloalkyl, optionally substituted aryl, heteroaryl, carboxyl, —$NR_2$, sulfonic acid, —SR, or —OR. In certain embodiments, $R^1$ for each instance is independently H, $C_1$-$C_{10}$ alkyl, $C_1$-$C_8$ alkyl, $C_1$-$C_6$ alkyl, $C_3$-$C_6$ cycloalkyl, or $C_5$-$C_6$ cycloalkyl. In certain embodiments, $R^1$ for each instance is independently F, Cl, H, or $C_1$-$C_6$ alkyl.

$R^1$ can optionally further comprise reactive functionality capable forming a covalent bond with complimentary functionality present in an active agent thereby forming an active agent CPL conjugate. The active agent can be a small molecule, polypeptide, protein, antibody, or antibody fragment that is capable of selectively binding to a specific peptide, protein, carbohydrate, lipid, feature(s) found on cell membrane, organelle, organ, tissues and/or other antigen and can allow the active agent CPL conjugate selectively bind, detect, analyze, and/or image analytes, antigens, cells, organs, tissues, or other species of interest. In such instances, $R^1$ can further comprise a terminal functional group selected from the group consisting of $N_3$, NCS, SH, $NH_2$, COOH, alkyne, N-hydroxysuccinimide ester, maleimide, hydrazide, nitrone group, —CHO, OH, halide, and charged ionic group. In certain embodiments, $R^1$ is —$(CH_2)_n$Q, wherein n is an integer between 0-8 and Q is the terminal functional group. In certain embodiments, Q is $N_3$, $NH_2$, COOH, alkyne, N-hydroxysuccinimide ester, or maleimide. The selection of the appropriate terminal functional group, the complimentary reactive functionality present in an active agent and conditions for their reaction are well within the skill of a person of ordinary skill in the art.

In certain embodiments, R for each instance is independently selected from the group consisting of H, $C_1$-$C_{10}$ alkyl, and $C_3$-$C_7$ cycloalkyl. In certain embodiments, R for each instance is independently selected from the group consisting of H, $C_1$-$C_{10}$ alkyl, $C_1$-$C_8$ alkyl, $C_1$-$C_6$ alkyl, $C_3$-$C_7$ cycloalkyl, $C_3$-$C_6$ cycloalkyl, $C_4$-$C_6$ cycloalkyl, and $C_5$-$C_6$ cycloalkyl.

In certain embodiments, each of $X^1$ and $X^2$ is independently selected from the group consisting of:

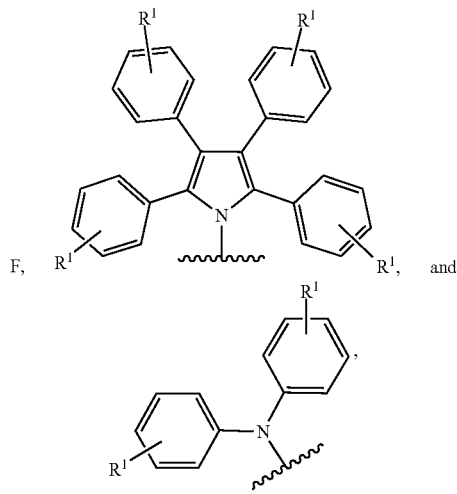

wherein $R^1$ for each instance is independently H, $C_1$-$C_{10}$ alkyl, $C_1$-$C_8$ alkyl, $C_1$-$C_6$ alkyl, $C_3$-$C_6$ cycloalkyl, or $C_5$-$C_6$ cycloalkyl.

In certain embodiments, each of $X^1$ and $X^2$ is independently selected from the group consisting of:

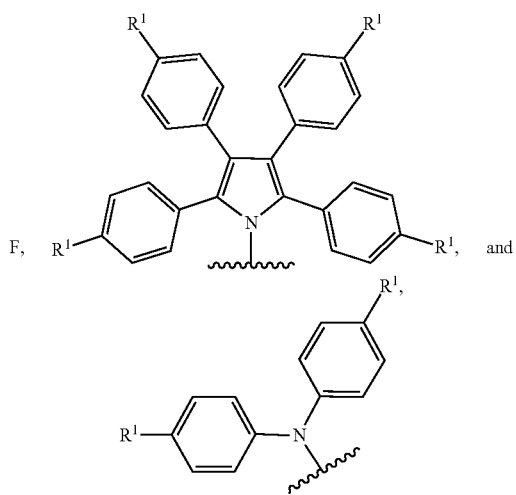

$R^1$ for each instance is independently H, $C_1$-$C_{10}$ alkyl, $C_1$-$C_8$ alkyl, $C_1$-$C_6$ alkyl, $C_3$-$C_6$ cycloalkyl, or $C_5$-$C_6$ cycloalkyl.

In certain embodiments, each of $X^1$ and $X^2$ is independently selected from the group consisting of:

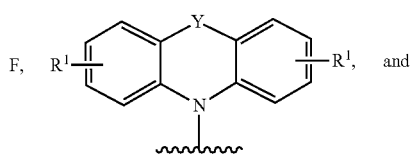

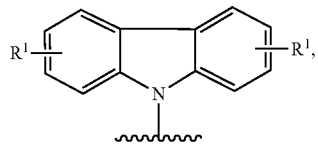

wherein Y is —N(R)—, O, or —C(R)$_2$—; R is independently H or alkyl; and $R^1$ for each instance is independently H, $C_1$-$C_{10}$ alkyl, $C_1$-$C_8$ alkyl, $C_1$-$C_6$ alkyl, $C_3$-$C_6$ cycloalkyl, or $C_5$-$C_6$ cycloalkyl.

In certain embodiments, each of $X^1$ and $X^2$ is independently selected from the group consisting of:

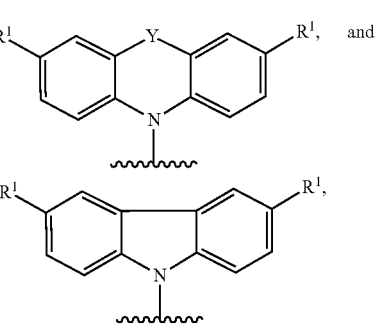

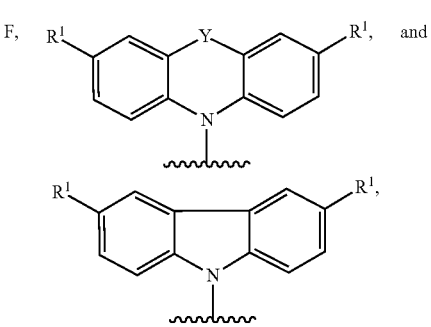

wherein Y is —N(R)—, O, or —C(R)$_2$— and R is independently H or $C^1$-$C^6$ alkyl.

In certain embodiments, the compound of Formula I is represented by:

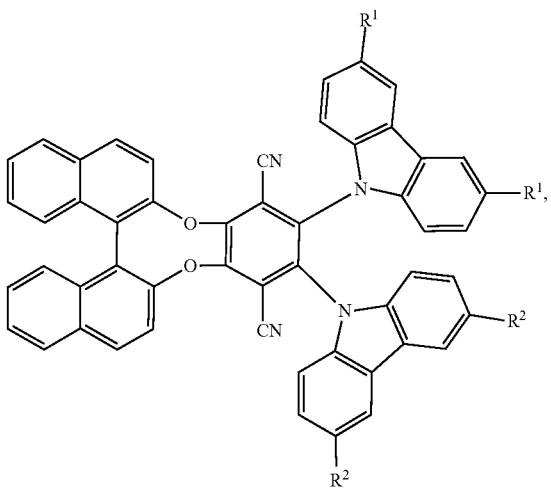

wherein $R^1$ is H or alkyl and $R^2$ is alkyl; or $R^1$ is $C_1$-$C_{10}$ alkyl, $C_1$-$C_8$ alkyl, or $C_1$-$C_6$ alkyl, and $R^2$ is $C_1$-$C_{10}$ alkyl, $C_1$-$C_8$ alkyl, or $C_1$-$C_6$ alkyl; or $R^1$ is H and $R^2$ is $C_1$-$C_{10}$ alkyl, $C_1$-$C_8$ alkyl, or $C_1$-$C_6$ alkyl, and $R^2$ is $C_1$-$C_{10}$ alkyl, $C_1$-$C_8$ alkyl, or $C_1$-$C_6$ alkyl.

In certain embodiments, the compound of Formula I is represented by:

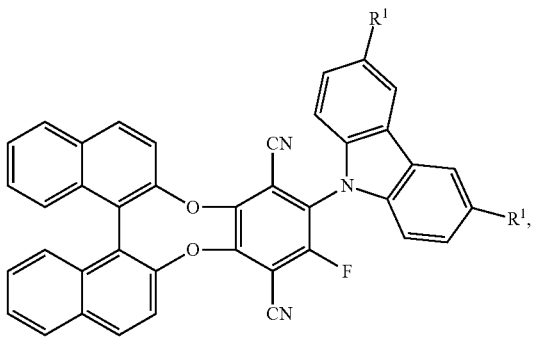

wherein $R^1$ is H or alkyl with the proviso that if $R^1$ is H, the compound is isolated, pure, or present in a film; or $R^1$ is $C_1$-$C_{10}$ alkyl, $C_1$-$C_8$ alkyl, or $C_1$-$C_6$ alkyl.

In certain embodiments, the compound of Formula I is represented by:

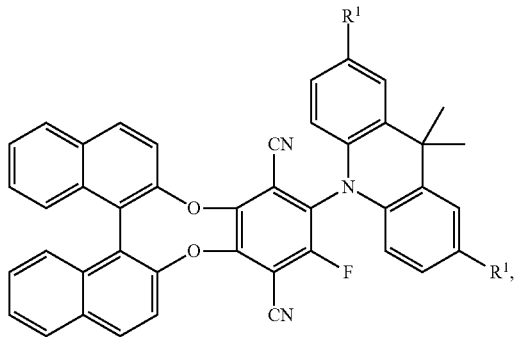

wherein $R^1$ is H or alkyl; or $R^1$ is $C_1$-$C_{10}$ alkyl, $C_1$-$C_8$ alkyl, or $C_1$-$C_6$ alkyl.

The EL properties of the compound of Formula I can be particularly useful in the fabrication of luminescent devices, such as variously configured CPOLED. CPOLEDs that can be fabricated using the compounds of Formula I include from very simple structures having a single anode and cathode (e.g., monolayer CPOLEDs) to more complex devices, such as 2-layer or multilayer heterostructure configurations.

In certain embodiments, the CPOLED comprises an anode, a cathode, and a light emissive layer disposed between the anode and the cathode. In certain embodiments the CPOLED further comprises a hole-transport layer.

In certain embodiments, the CPOLED has the structure shown in FIG. 32. CPOLED 100 contains an anode 110, a hole-injection layer 120, a hole-transport layer 130, a light-emitting layer 140, an electron-transport layer 150, an electron-injection layer 160 and a cathode 170. The light-emitting layer 140 can comprises the compound of Formula I as a thin film or as dopant dispersed in a host matrix. In some other embodiments, there are optional layers on either side of the light-emitting layer 140.

In certain embodiments, the electron-injection layer 160 can be subdivided into two or more sublayers (not shown). In one illustrative example of the CPOLED, the electron-injection layer 170 is further divided into two sublayers, a first electron-injection layer adjacent to the electron-transport layer 150 and a second electron-injection layer located between the first electron-injection layer and the cathode.

In certain embodiments, the hole-injection layer 120 can be subdivided into two or more sublayers (not shown). In one illustrative example of the CPOLED device, the hole-injection layer 120 is further divided into two sublayers, a first hole-injection layer adjacent to the hole-transport layer 130 and a second hole-injection layer located between the first hole-injection layer and the anode.

In certain embodiments, there is a hole-blocking layer between the light-emitting layer 140 and the electron-transport layer 150 (not shown).

The CPOLED can be configured such that the EL emission of the anode or alternatively through the cathode. When the EL emission occurs through the anode, the anode 110 should be transparent or substantially transparent to the emitted wavelengths. Commonly used transparent anode materials include, but are not limited to, indium-tin oxide (ITO), indium-zinc oxide (IZO) tin oxide, aluminum- or indium-doped zinc oxide, magnesium-indium oxide, nickel-tungsten oxide, gallium nitride, zinc selenide, zinc sulfide. When the EL emission occurs through the cathode 170, the optical properties of the anode 110 are immaterial and any conductive material, transparent, opaque or reflective can be used. Example conductors for this application include, but are not limited to, gold, iridium, molybdenum, palladium, and platinum.

The anode 110 can be deposited using any suitable way such as evaporation, sputtering, chemical vapor deposition, or electrochemical processes. Anodes can be patterned using, e.g., conventional photolithographic processes.

The hole-injection material can serve to facilitate injection of holes into the hole-transport layer 130. The hole-injection layer 120 can be formed of any hole-injection material including those that are commonly used. Non-limiting examples of hole-injection materials are N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl-N,N'-diphenylbenzidine) (NPB), 4,4',4"-tris(N,N-diphenylamino)triphenylamine (TDATA), 4,4',4"-tris-(N-(naphthylen-2-yl)-N-phenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), tetracyanoquinonedimethane (TCNQ), 2,3,5,6-tetrafluoro-tetracyano-1,4-benzoquinonedimethane (F4-TCNQ) and additional hole-injection materials, such as dipyrazino[2,3-f:2',3'-h]quinoxalinehexacarbonitrile (HATCN) are described in U.S. Publication 2004/0113547 A1 and U.S. Pat. No. 6,720,573.

The hole-injection material can be deposited using any suitable conventional method known in the art including, but not limited to, vacuum deposition, spin coating, printing, print screening, spraying, painting, doctor-blading, slot-die coating, and dip coating.

The hole-transport layer 130 can be formed of any hole-transport material including those that are commonly used. Non-limiting examples of suitable known hole-transport materials are carbazole derivatives, such as N-phenylcarbazole or polyvinylcarbazole, N,N'-bis(3-methylphenyl-N,N'-diphenyl-[1,1-biphenyl]-4,4'-diamine (TPD), 4,4',4"-tris(N-carbazolyl)triphenylamine (TCTA), (4,4'-(cyclohexane-1,1-diyl)bis(N,N-di-p-tolylaniline)) (TAPC), and N,N'-di(1-naphthyl-N,N'-diphenylbenzidine) (NPB).

The hole-transport material can be deposited using any suitable conventional method known in the art including, but not limited to, vacuum deposition, spin coating, printing, print screening, spraying, painting, doctor-blading, slot-die coating, and dip coating.

The light-emitting layer 140 can comprise a substantially pure thin film comprising a compound of Formula 1 or a host matrix doped with a compound of Formula I. In instance in which the light-emitting layer comprises a host matrix, the host matrix can be any host matrix material known in the art. Non-limiting examples of host matrix materials include bis(4-(3,6-diphenyl-9H-carbazol-9-yl)phenyl)methanone, 9-(4-(4,6-diphenylpyrimidin-2-yl)phenyl)-9H-carbazole, 4-(4-diphenylaminophenyl)diphenylsulfone, 9-(9-phenyl-9H-carbazol-3-yl)-9-p-tolyl-9H-fluorene-3-carbonitrile, 3,5-di(9H-carbazol-9-yl)benzonitrile, 2-(diphenylphosphinyl)-spiro[9H-fluorene-9,9'-quino[3,2,1-kl]phenoxazine], 2,8-bis(diphenylphosphoryl)dibenzo[b,d]thiophene, 4,4'-bis(carbazol-9-yl)biphenyl, 4,4',4"-tris(carbazol-9-yl)triphenylamine, 2,6-bis(9,9-diphenylacridin-10(9H)-yl)pyrazine, 1,3-bis(carbazol-9-yl)benzene, 4,4',4"-Tris(carbazol-9-yl) triphenylamine, 4,4'-bis(carbazol-9-yl)biphenyl, 9-(4-tert-butylphenyl)-3,6-bis(triphenylsilyl)-9H-carbazole, 1,3,5-tri [(3-pyridyl)-phen-3-yl]benzene, 2,8-bis(diphenylphosphoryl)dibenzo[b,d]thiophene, bis[2-(diphenylphosphino)phenyl]ether oxide, 2,6-di(9H-carbazol-9-yl)pyridine, 3',5'-di(carbazol-9-yl)-[1,1'-biphenyl]-3,5-dicarbonitrile, 4,4'-(9H,9'H-3,3'-bicarbazole-9,9'-diyl)bis(N,N-diphenylaniline), 4'-(9H-carbazol-9-yl) biphenyl-3,5-dicarbonitrile, 3'-(9H-carbazol-9-yl)biphenyl-3,5-dicarbonitrile, 2,8-bis(diphenylphosphoryl)dibenzo[b,d] furan, and 3,5-di(carbazol-9-yl)-1-phenylsulfonylbenzene. The compound of Formula 1 can be present in the host material at a concentration of 1-20% w/w.

The light-emitting material can be deposited using any suitable conventional method known in the art including, but not limited to, vacuum deposition, spin coating, printing, print screening, spraying, painting, doctor-blading, slot-die coating, and dip coating.

Any suitable electron-transport material may be used to form the electron-transport layer 150. As the electron-transport material, any electron-transporting material that can stably transport electrons injected from an electron injecting electrode (cathode) may be used as a material for the electron-transport layer. Non-limiting examples of useful electron-transport materials may include quinoline derivatives such as tris(8-quinolinorate)aluminum (Alq3), 3-(biphenyl-4-yl)-4-phenyl-5-(4-t-butylphenyl)-1,2,4-triazole (TAZ), bis(2-methyl-8-quinolinato-N1,O8)-(1,1'-biphenyl-4-olato)aluminum (BAlq), beryllium bis(benzoquinolin-10-olate) (Bebq2), 9,10-di(naphthalene-2-yl)anthracene (ADN), and (3,3",5,5"-tetra(pyridin-3-yl)-1,1':3',1"-terphenyl (BmPyPhB).

The electron-transport material can be deposited using any suitable conventional method known in the art including, but not limited to, vacuum deposition, spin coating, printing, print screening, spraying, painting, doctor-blading, slot-die coating, and dip coating.

Any suitable electron-injection material may be used to form the electron-injection layer 160. Non-limiting examples of electron injecting materials useful for forming the electron-injection layer 160 are LiF, NaCl, CsF, $Li_2O$, 8-hydroxyquinolinato-lithium (Liq) and BaO.

The electron-injection material can be deposited using any suitable conventional method known in the art including, but not limited to, vacuum deposition, spin coating, printing, print screening, spraying, painting, doctor-blading, slot-die coating, and dip coating.

The cathode 170 can comprise any anodic material known to those of skill in the art. In certain embodiments, the anode comprises lithium, magnesium, calcium, aluminum, gold, indium, copper, silver, or a combination thereof. In certain embodiments, the anode comprises aluminum.

The cathode 170 can be deposited using any suitable way such as evaporation, sputtering, chemical vapor deposition, or electrochemical processes. Anodes can be patterned using, e.g., conventional photolithographic processes.

The luminescent devices described herein can be incorporated into a wide variety of consumer products, including flat panel displays, computer monitors, televisions, billboards, lights for interior or exterior illumination and/or signaling, heads up displays, fully transparent displays, flexible displays, cell phones, personal laptop computers, digital cameras, camcorders, viewfinders, micro-displays, vehicles, a large area wall, theater or stadium screen, or a sign.

The materials and structures described herein may have applications in devices other than CPOLEDs. For example, other optoelectronic devices such as organic solar cells and organic photodetectors may employ the materials and structures. More generally, organic devices, such as organic transistors, may employ the materials and structures described herein.

Figure 1:
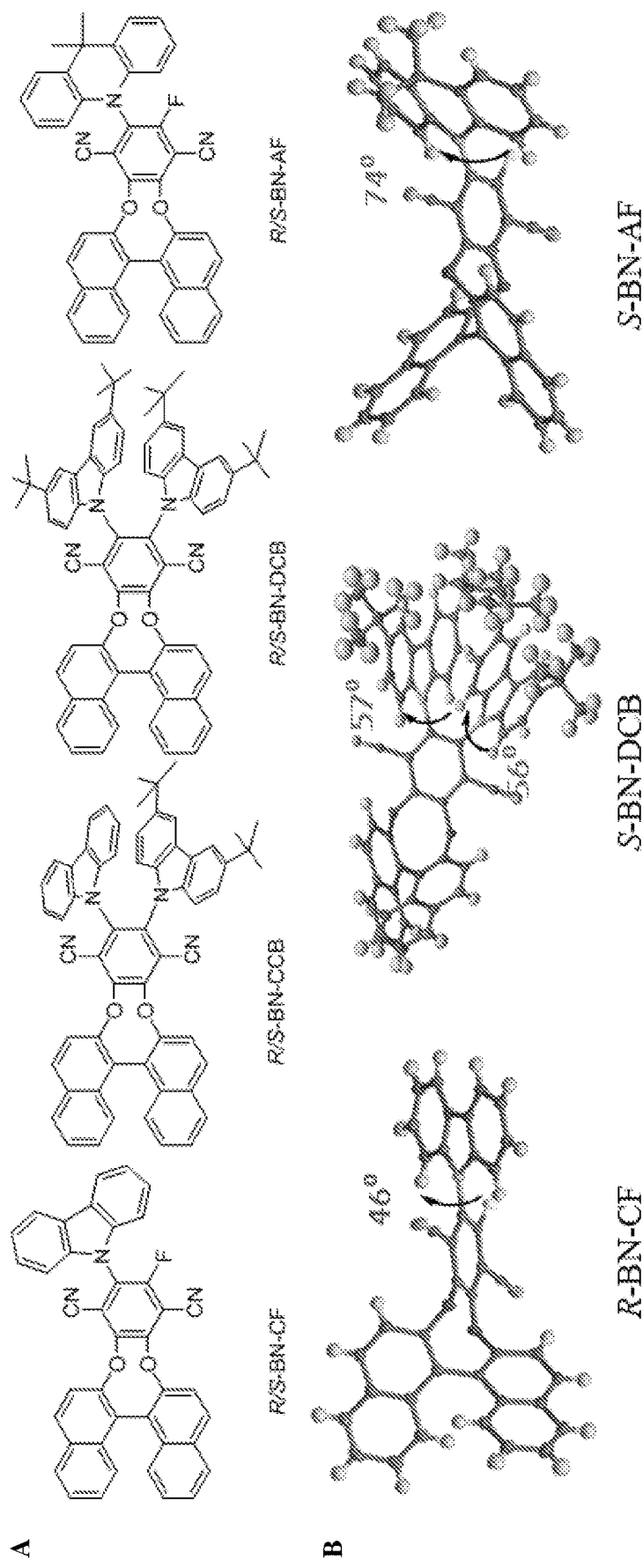
FIG. 1 depicts (A) Chemical structures of exemplary compounds R-BN-CF, S-BN-DCB and S-BN-AF. (B) Single-crystal structure of R-BN-CF, S-BN-DCB and S-BN-AF. Solvent molecules are omitted for clarity. (C) Frontier orbital amplitude plots and highest occupied molecular orbital (HOMO)/lowest unoccupied molecular orbital (LUMO) values, calculated by density functional theory (DFT) method. $\Delta E_{ST}$ values, calculated by time-dependent density functional theory (TDDFT) method.
Figure 1:
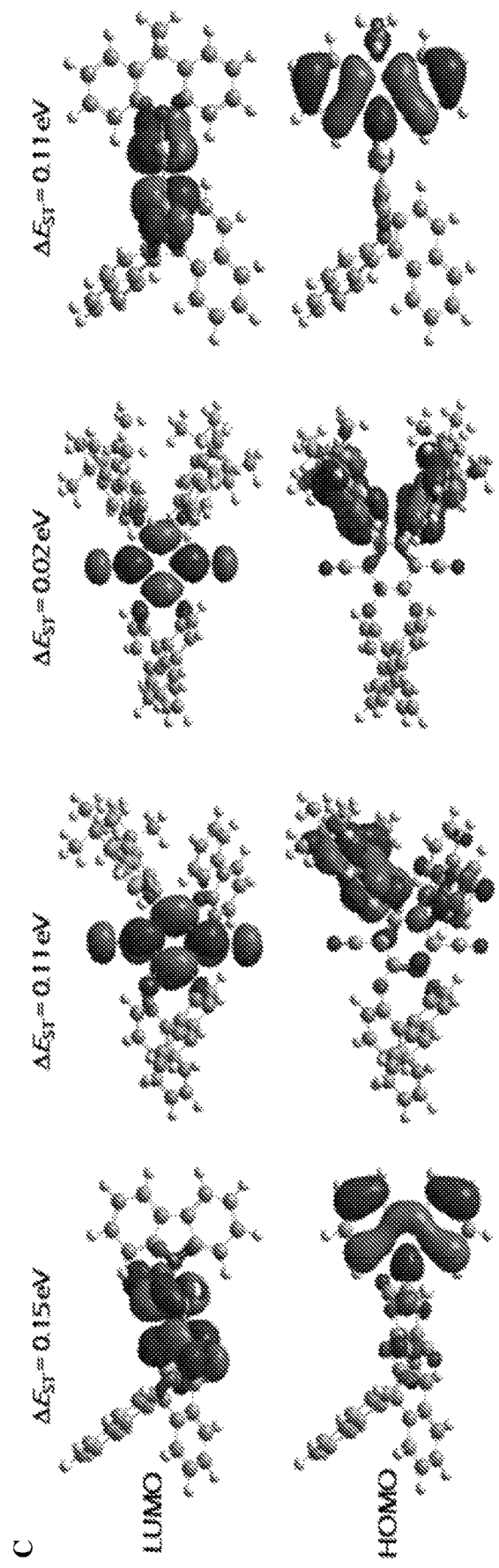
Figure 10:
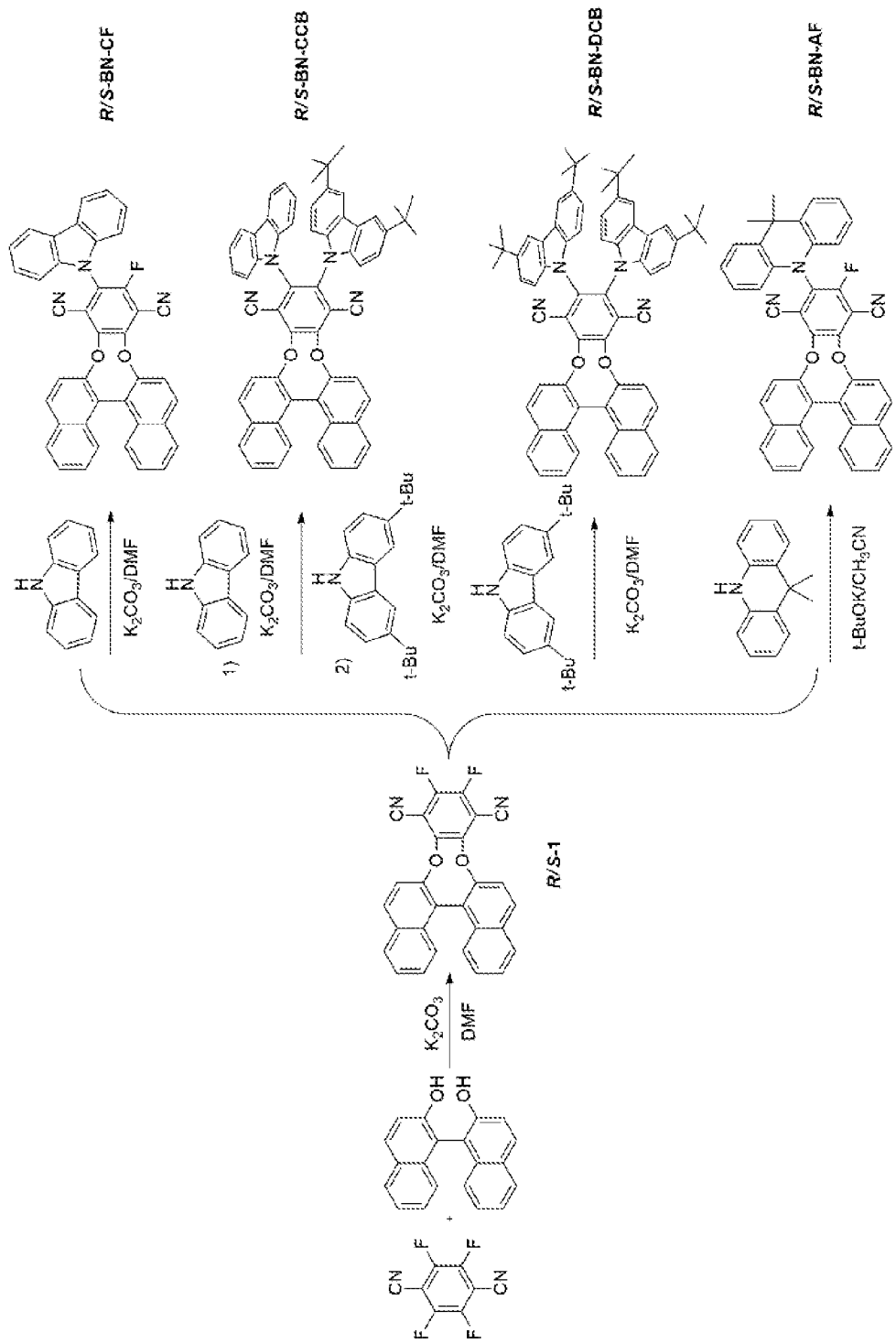
FIG. 10 depicts an exemplary synthetic procedures for the preparation of R/S-BN-CF, R/S-BN-CCB, R/S-BN-DCB and R/S-BN-AF.
Figure 11:
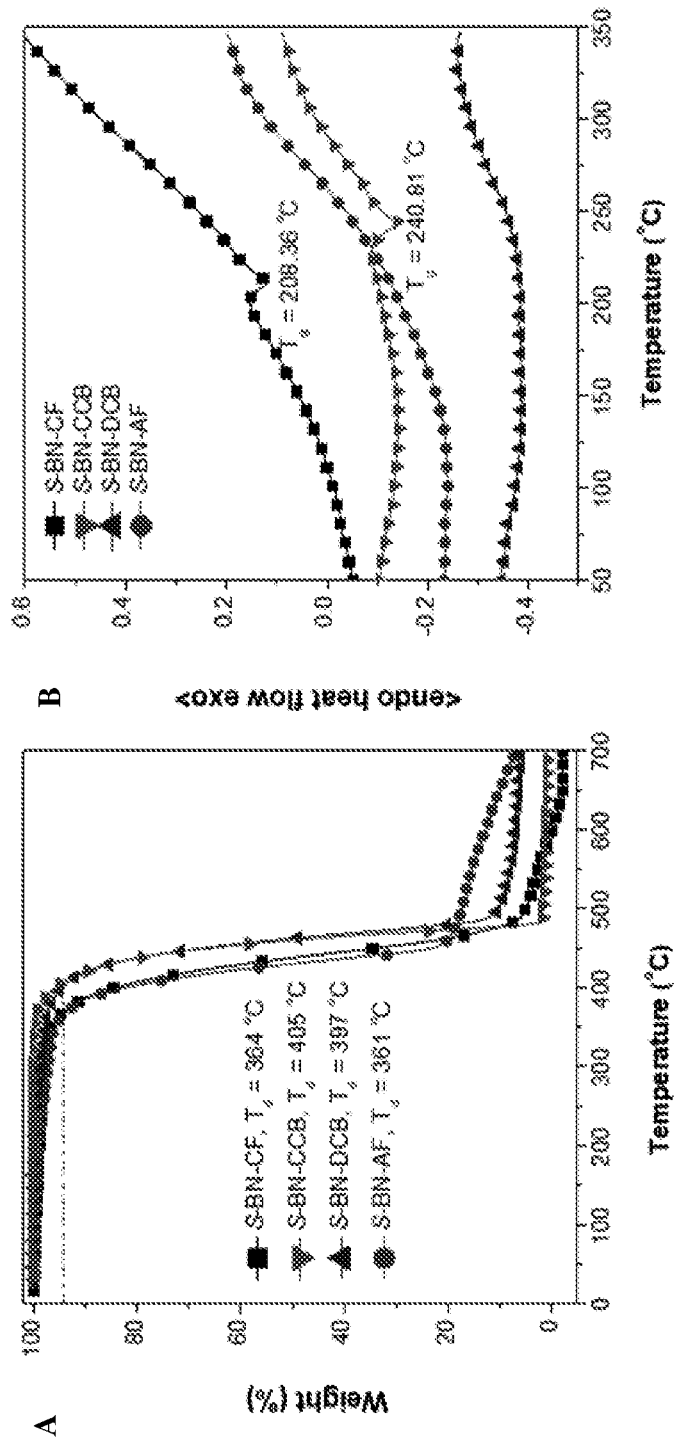
FIG. 11 depicts (A) TGA and (B) DSC thermograms of S-BN-CF, S-BN-CCB, S-BN-DCB and S-BN-AF recorded under nitrogen at a heating rate of 10° C. $min^{-1}$, respectively.

FIG. 1A illustrates the chemical structures of exemplary compounds of Formula I: R/S-BN-CF, R/S-BN-CCB, R/S-BN-DCB and R/S-BN-AF (exemplary compounds). The synthesis procedures of these compounds are outlined in FIG. 10. R/S-BN-CF and R/S-BN-AF were synthesized by the reaction of R/S-1 with carbazole (Cz) and 9,9-dimethyl-9,10-dihydroacridine with the 1:1 mole ratio under the alkaline condition. R/S-BN-DCB could be obtained by nucleophilic substitution from R/S-1 and 3,6-di-tert-butyl-carbazole with the 1:2.2 mole ratio. R/S-BN-CCB was obtained by the reaction of R/S-BN-CF and 3,6-di-tert-butyl-carbazole with the 1:1.5 mole ratio under the alkaline condition in 91% yield. All the exemplary compounds were obtained by a highly efficient and concise synthetic route (FIG. 10). Their structures were confirmed by NMR, high resolution mass spectra (HRMS), and single X-ray diffraction (FIG. 1B). The exemplary compounds possessed good solubility and can be completely dissolved in commonly used organic solvents, such as dichloromethane (DCM), chloroform, tetrahydrofuran (THF), N,N-dimethylformamide (DMF) and $CH_3OH$. Thermal stability is a significant parameter for CPOLED materials. Thus, the thermal properties of the exemplary compounds described herein by thermogravimetric analysis (TGA) and differential scanning calorimetry (DSC) were evaluated. As can be seen in FIG. 11, the temperatures of 5% weight loss ($T_d$) of the exemplary compounds are all higher than 360° C. under nitrogen, indicating that these exemplary compounds are of good stability and can be applied for CPOLED materials. The glass-transition temperatures ($T_g$) of S-BN-CF is at around 208° C., while S-BN-CCB shows an enhanced temperatures ($T_g$) at around 240° C. likely due to the presence of the bulky carbazole unite. No signal related to the glass transition temperature was detected in S-BN-DCB and S-BN-AF even when heated to 350° C., presumably due to their highly rigid and twisted structure. These results indicate that all the exemplary compounds are thermally stable.

Figure 12:
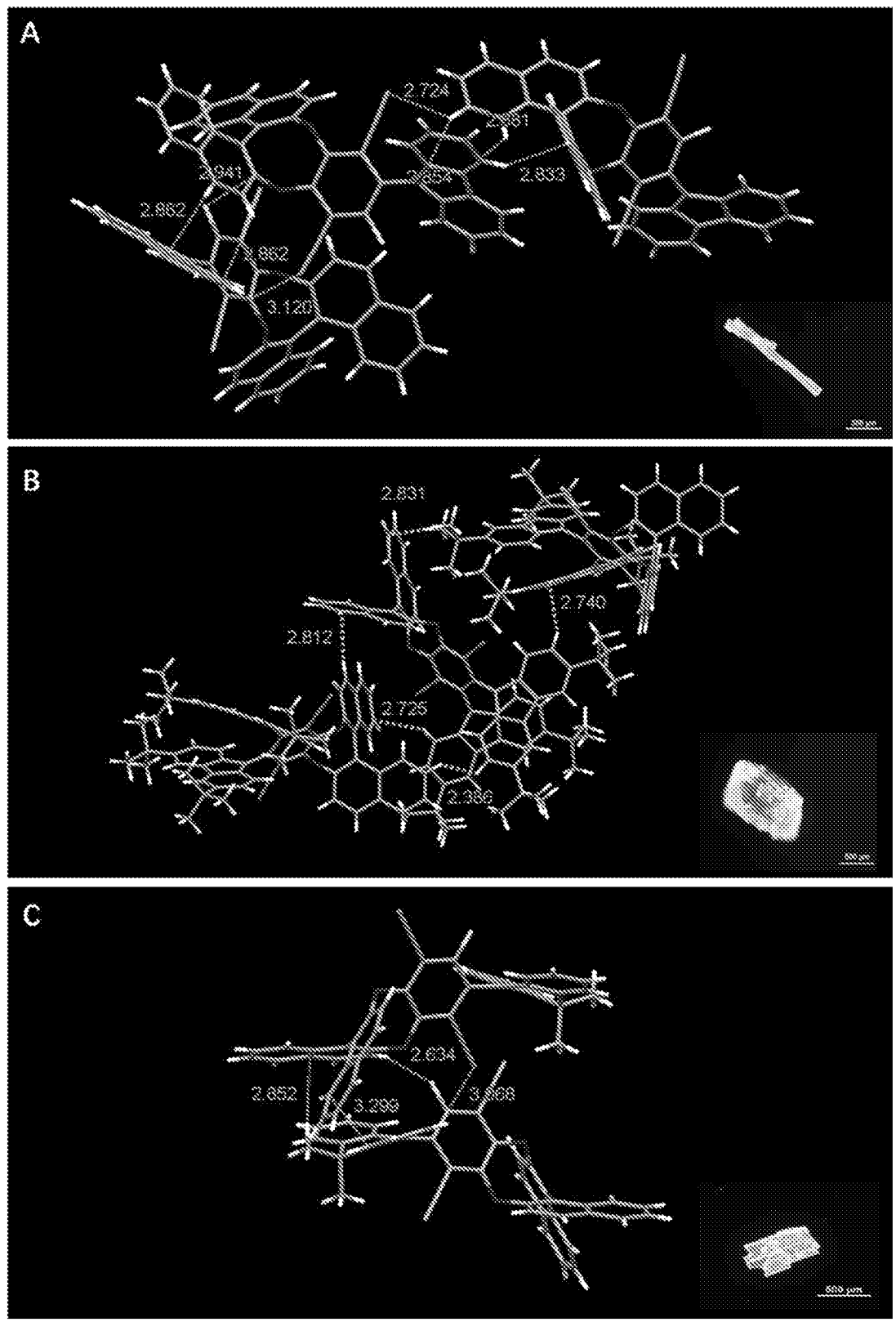
FIG. 12 depicts packing diagrams of (A) R-BN-CF, (B) S-BN-DCB, and (C) S-BN-AF.

The single-crystal structures of R-BN-CF, S-BN-DCB and S-BN-AF from crystallography analysis are displayed in FIG. 1B. Single crystals of R-BN-CF and S-BN-DCB were grown from the hexane-ethyl acetate mixture by slow solvent evaporation. The crystalline sample of S-BN-AF was obtained from slow evaporative crystallization using $CH_2Cl_2$-$C_2H_5OH$ mixture. As illustrated in FIG. 1B R-BN-CF, S-BN-DCB and S-BN-AF adopted a twisted conformation. Taking the single-crystal structure of R-BN-CF as an example (FIG. 1B), the carbazole and phenyl form moderate torsion angle (ψ) of 46°, which is conductive to lower electronic coupling and efficient separation of HOMO and LUMO (FIG. 1C). Consequently, small $\Delta E_{ST}$ and the reverse intersystem crossing (RISC) process is facilitated, rendering prominent delayed fluorescence property. As for S-BN-DCB and S-BN-AF, we also found the similar twisted conformation in their single-crystal structures. The torsion angle (ψ) of 74° between 9,9-dimethyl-9,10-dihydroacridine (DMAC) unit and phenyl for S-BN-AF was observed and the two moderate torsion angles (ψ) of 56° and 57° were also illustrated in S-BN-DCB crystallography. These twisted conformations may efficiently suppress exciton annihilation due to the weakened intermolecular interactions. In addition, the crystal packing pattern of R-BN-CF, S-BN-DCB and S-BN-AF were also investigated and illustrated in FIG. 12. As is evident from FIG. 12, numerous C-H . . . π and C-H . . . N interactions were found in the crystal state. As shown in FIG. 12's inset, the single crystal of R-BN-CF, S-BN-DCB and S-BN-AF are able to emit light blue, yellow and orange fluorescence. We also found that there are no close π-π stacking interactions in R-BN-CF and S-BN-DCB crystals due to the twisted connection, while a close π-π stacking (3.30 Å) was found between DMAC unit and naphthalene moiety in the S-BN-AF crystal. More importantly, the DMAC unit has a crooked conformation in the S-BN-AF crystal state, which can be harmful to TADF performance and can lead to a low quantum yield (QY). The foregoing interactions may explain measured QY for the exemplary compounds in which the QY of neat film for S-BN-AF is only 5.3%, while the QY of neat film for S-BN-CF and S-BN-DCB were 38.7% and 22.1% [Table 1 (FIG. 3)].

Figure 13:
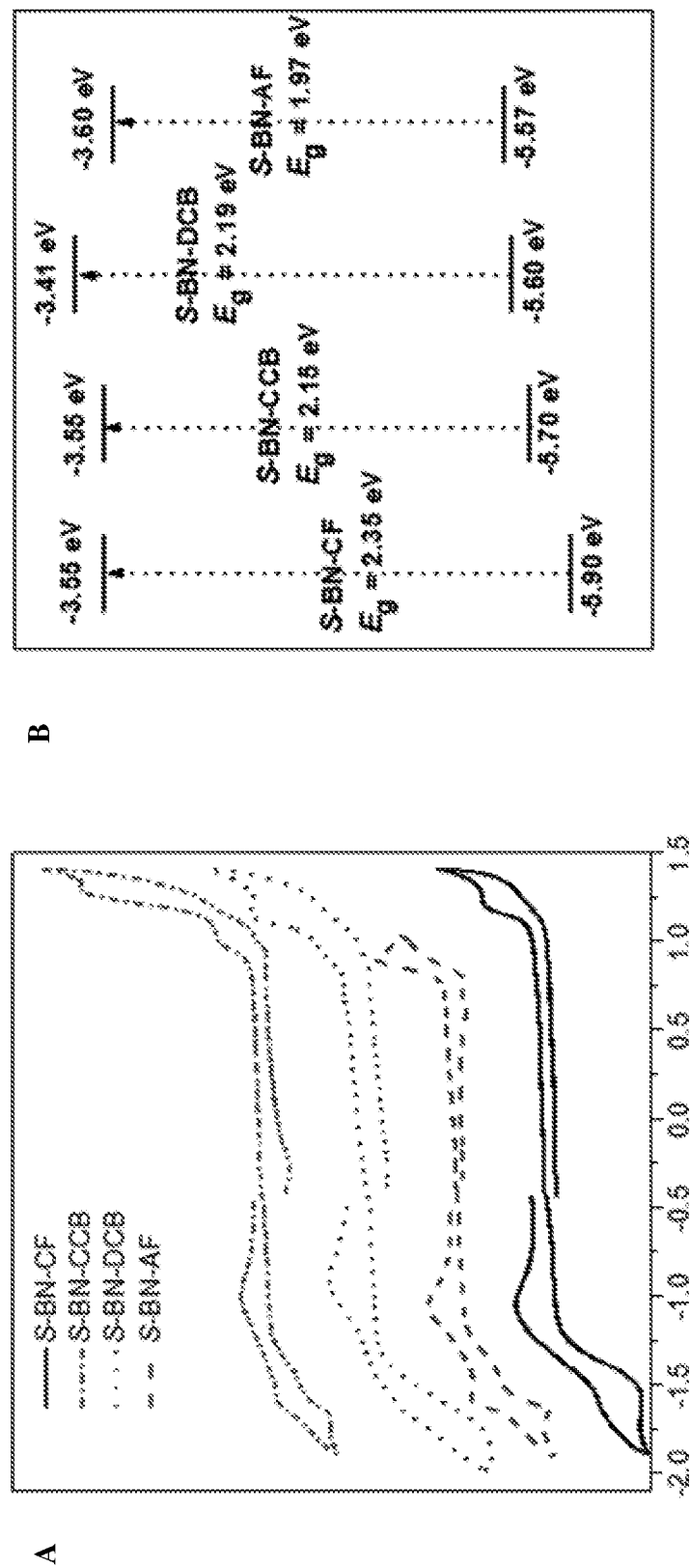
FIG. 13 depicts (A) cyclic voltammograms of S-BN-CF, S-BN-CCB, S-BN-DCB and S-BN-AF measured in $CH_3CN$ containing 0.1 M tetra-n-butylammonium hexafluorophosphate. Scan rate: 100 mV/s. (B) Energy level and energy gap of S-BN-CF, S-BN-CCB, S-BN-DCB and S-BN-AF calculated from cyclic voltammograms. Conditions: the ferrocene couple ($Fc/Fc^+$) was used as the internal reference and under our experimental conditions, E ($Fc^+$/Fc)=0.42 V vs. Ag/AgCl. $E_{ox}$ and $E_{red}$ were determined from the onset potentials of the oxidation and reduction waves. The energy levels were calculated using the following equations: HOMO=−(4.8+$E_{oxonset}$) (eV), LUMO=−(4.8+$E_{redonset}$) (eV), $E_g$=LUMO−HOMO.

To gain a better insight into the electron cloud distribution and geometrical structures of R/S-BN-CF, R/S-BN-CCB, R/S-BN-DCB and R/S-BN-AF, the molecular simulations were calculated by DFT B3LYP/6-31G* method with the Gaussian 09 package. The lowest unoccupied molecular orbitals (LUMOs) are mainly located on the central phenyl with cyano substitution, whereas the highest occupied molecular orbitals (HOMOs) occupy the electron-donating Cz and DMAC moieties (FIG. 1C). Such separated electron cloud distribution of HOMO and LUMO can reduce $\Delta E_{ST}$. The calculated $\Delta E_{ST}$ of BN-CF, BN-CCB, BN-DCB and BN-AF in isolated state are 0.15 eV, 0.11 eV, 0.02 eV and 0.11 eV, respectively. In addition, the calculated data show that the BN-CF, BN-CCB, BN-DCB and BN-AF have LUMO and HOMO energy levels in the range of −2.51 to −2.69 eV and −5.25 to −5.79 eV, respectively. The band gaps were determined to be 3.11 eV, 2.97 eV, 2.87 eV and 2.70 eV for BN-CF, BN-CCB, BN-DCB and BN-AF. The CV curves of S-BN-CF, S-BN-CCB, S-BN-DCB and S-BN-AF are shown in FIG. 13A, and the electrochemical data are summarized in FIG. 13B. On the bases of these onset potentials, the HOMO/LUMO energy levels of S-BN-CF, S-BN-CCB, S-BN-DCB and S-BN-AF were determined to be −5.90/−3.55 eV, −5.70/−3.55 eV, −5.60/−3.41 eV and −5.57/−3.60 eV with the corresponding electrochemical band gaps of 2.36 eV, 2.15 eV, 2.17 eV and 2.00 eV, respectively. It can be found that the order of band gap (Eg) was S-BN-CF>S-BN-CCB≈S-BN-DCB>S-BN-AF. Although the calculated energy levels were higher than those determined by experiments, the trends of S-BN-CF, S-BN-CCB, S-BN-DCB and S-BN-AF in the band gaps were in good agreement with the ones obtained by CV measurements of the molecules.

Photophysical Properties.

Figure 2:
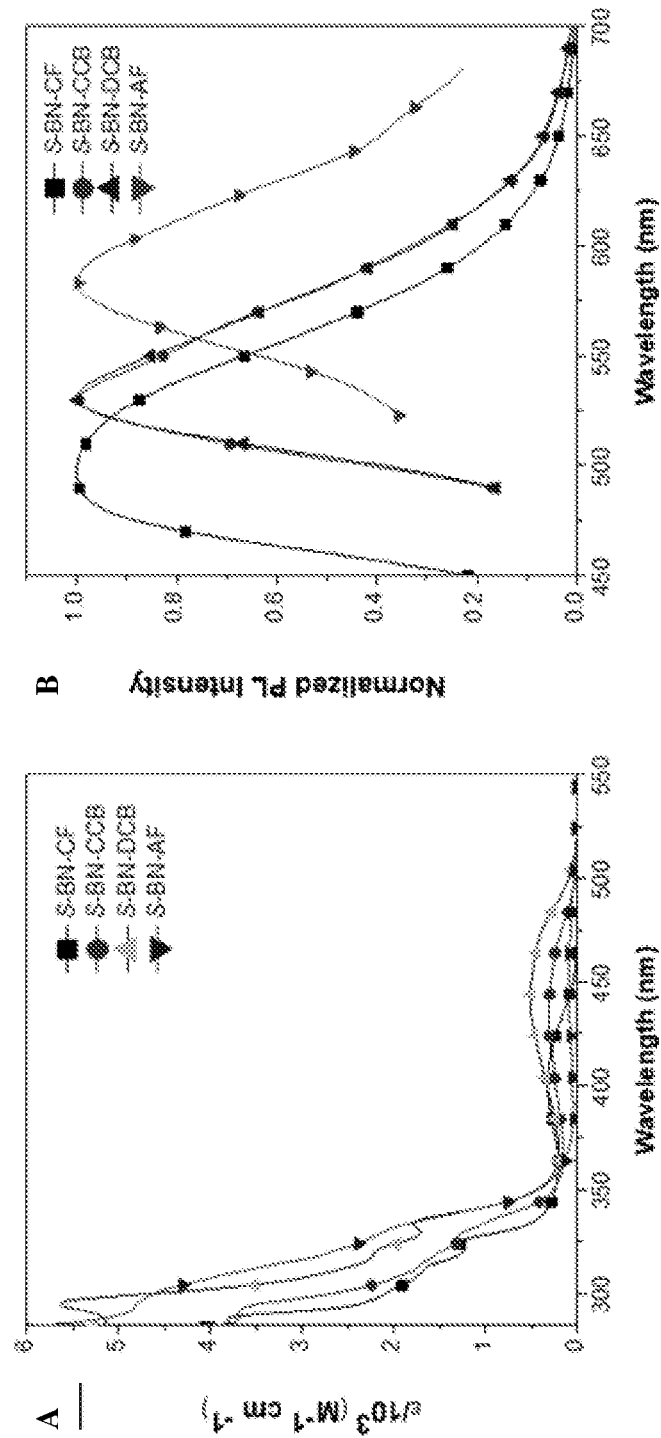
FIG. 2 depicts UV-Vis absorption (A) and photoluminescence (PL) spectra (B) of S-BN-CF, S-BN-CCB, S-BN-DCB and S-BN-AF in toluene at room temperature. (C) PL spectra of S-BN-CF in THF/$H_2O$ mixtures with different amounts of water ($f_w$=0%-99%). (D) Plots of the PL peak intensity and emission wavelength vs the water fraction ($f_w$). Insert: Fluorescence photographs of S-BN-CF in THF/$H_2O$ mixtures (up picture; $f_w$=0%, 70%, 99%), solid powder under 365 nm UV irradiation at room temperature (low picture). (E) Fluorescence photographs of S-BN-CCB, S-BN-DCB and S-BN-AF in THF/$H_2O$ mixtures (S-BN-AF: $f_w$=0%, 99%; S-BN-CCB and S-BN-DCB: $f_w$=0%, 60%, 95%), solid under 365 nm UV irradiation at room temperature. Conditions: the concentrations of S-BN-CF, S-BN-CCB, S-BN-DCB and S-BN-AF are 10 μmol $L^{-1}$. The excitation wavelengths of S-BN-CF, S-BN-CCB, S-BN-DCB and S-BN-AF are 400, 420, 440, 450 nm.
Figure 2:
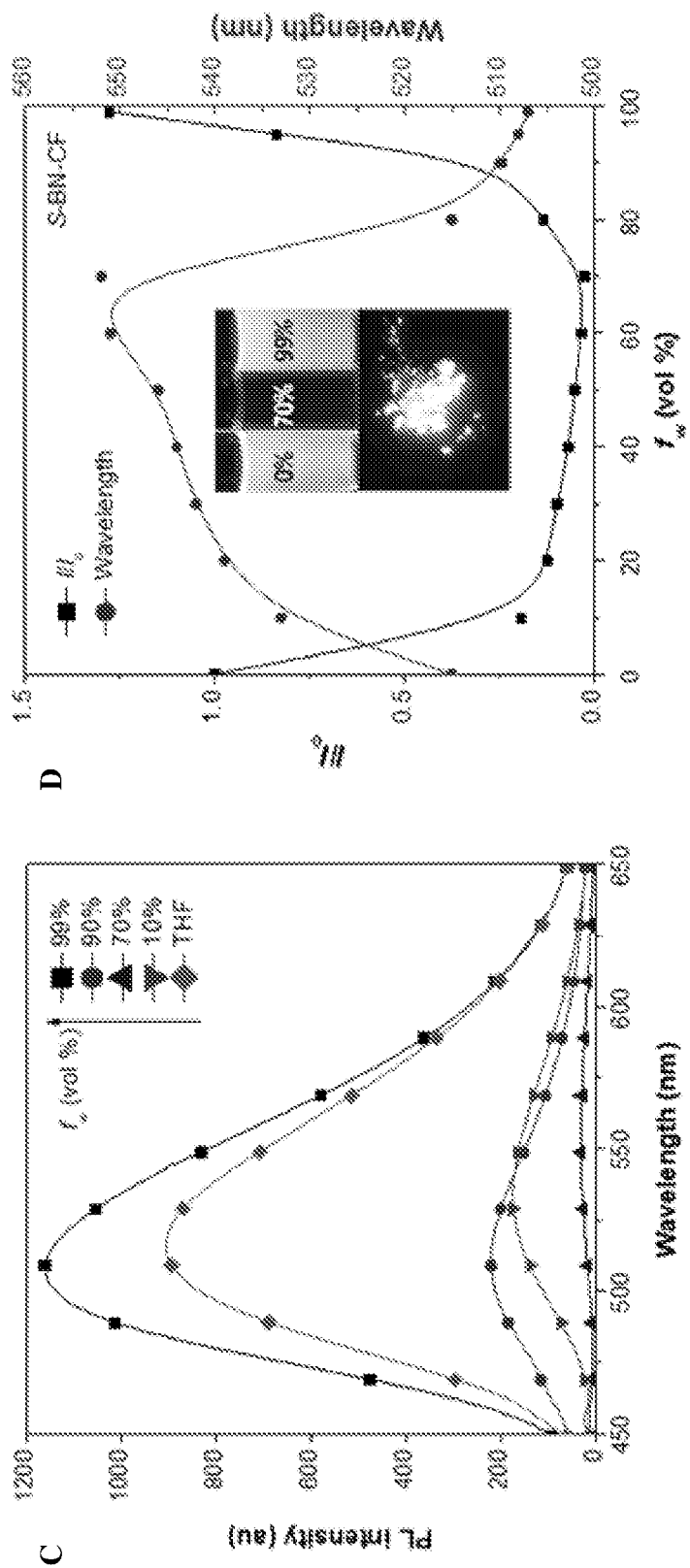
Figure 2:
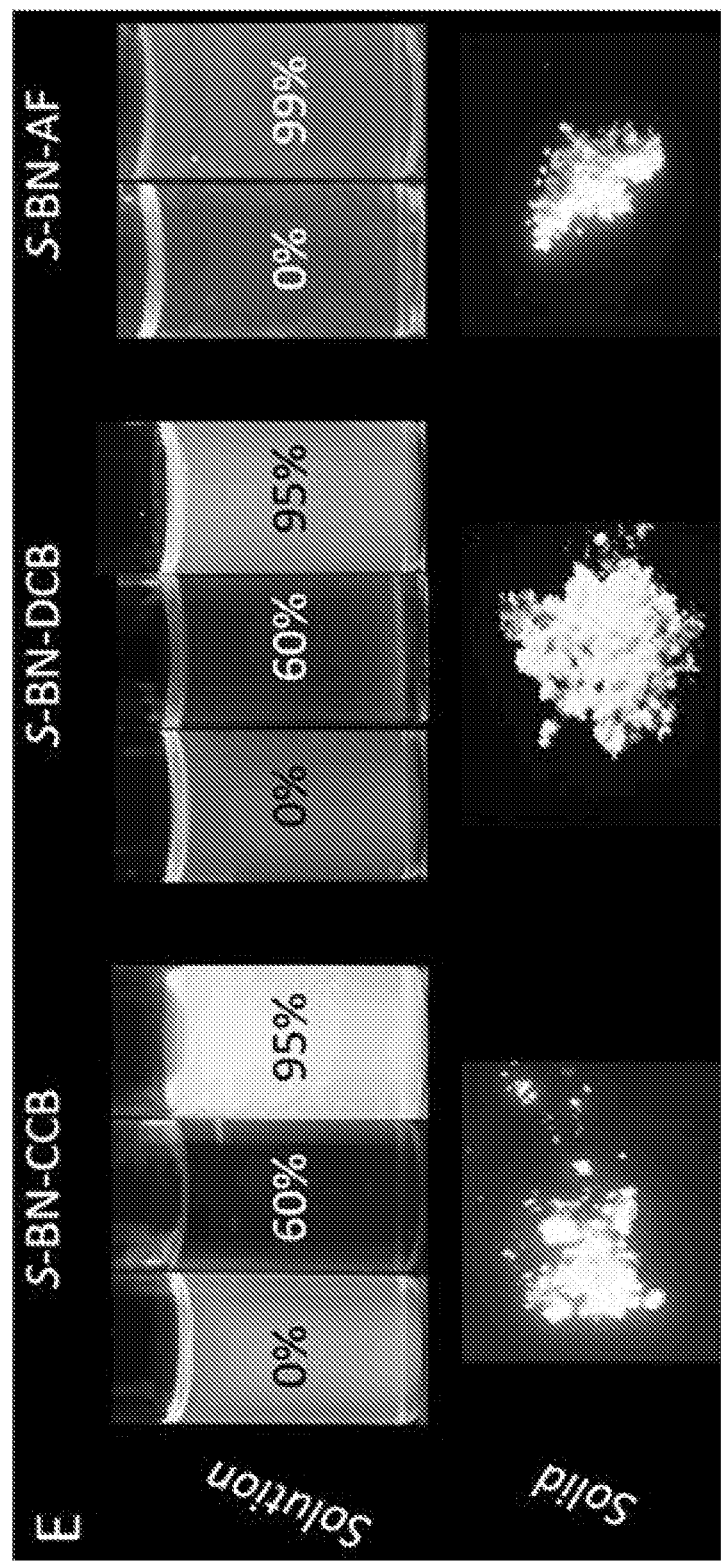

The UV-Vis absorption and photoluminescence (PL) spectra for S-BN-CF, S-BN-CCB, S-BN-DCB and S-BN-AF solutions in toluene are illustrated in FIG. 2A and FIG. 2B, and their photophysical parameters are summarized in Table 1 (FIG. 3). S-BN-CF, S-BN-CCB, S-BN-DCB and S-BN-AF show weak adsorption band centered at 400, 420, 440 and 450 nm, respectively, associated with intramolecular charge transfer (ICT) process derived from the D-A electronic structures. The exemplary compounds also show a strong absorption band at 330, 328, 326 and 325 nm, which are assigned to the absorption of BINOL, carbazole and DMAC unites. As is evident from FIG. 2A, the fluorescence spectrum of S-BN-CF, S-BN-CCB, S-BN-DCB and S-BN-AF have broad emission peak at 493, 530 and 531, 585 nm, respectively. The fluorescence quantum yields of the four molecules are 37.6% (S-BN-CF), 44.4% (S-BN-CCB), 52.2% (S-BN-DCB) and 7.8% (S-BN-AF) in solid state, respectively, indicating these four molecules are excellent solid luminescent emission materials. The fluorescence quantum yields of the four molecules are 0.5%, 0.8%, 1.2% and 2.0% in a solution of $CH_3OH$. Their $\alpha_{AIE}$ ($\Phi_{F,\ Solid}/\Phi_{F,\ Solution\ in\ MeOH}$) values were calculated to be 75, 56, 44 and 3.9, suggesting a typical AIE feature.

Figure 14:
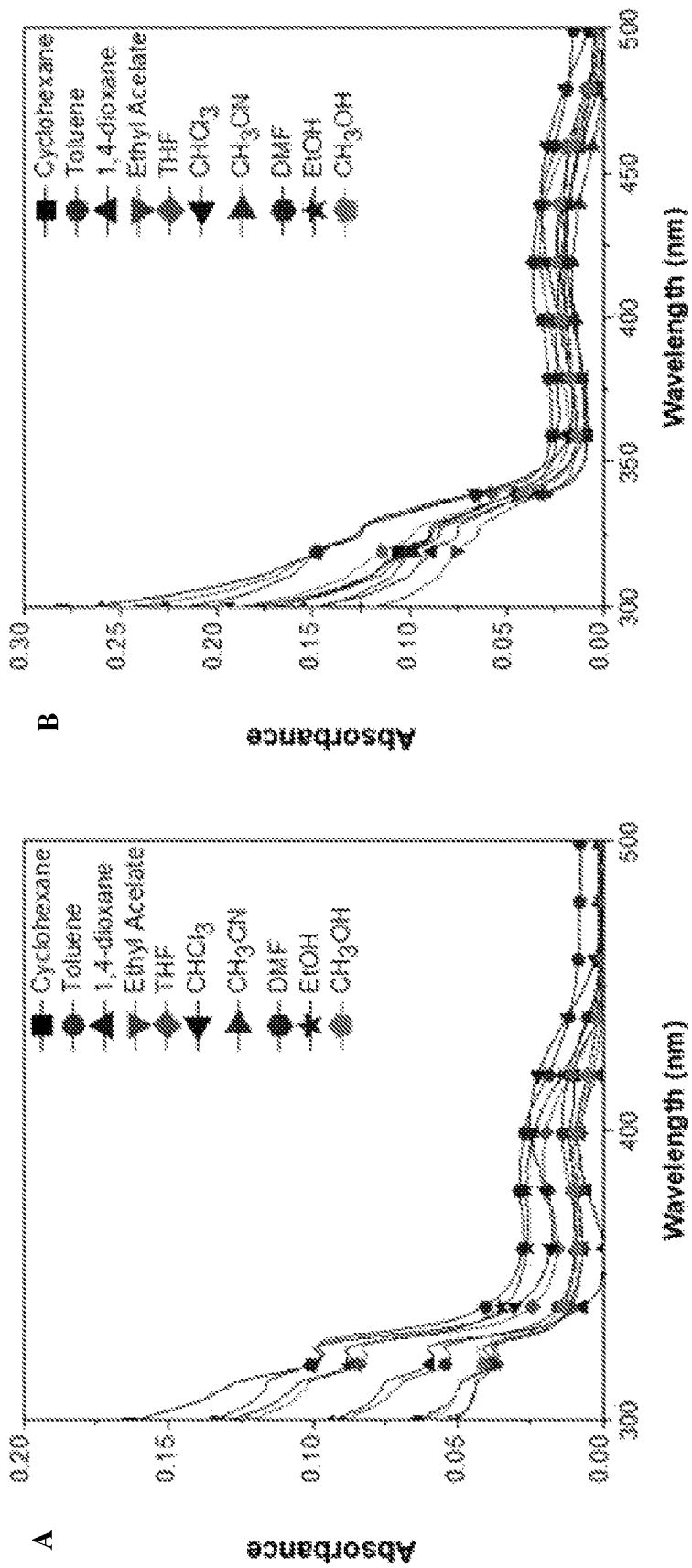
FIG. 14 depicts UV-Vis spectra of S-BN-CF (A), S-BN-CCB (B), S-BN-DCB (C) and S-BN-AF (D) in different solvents (concentration: 1×$10^{-5}$ M).
Figure 14:
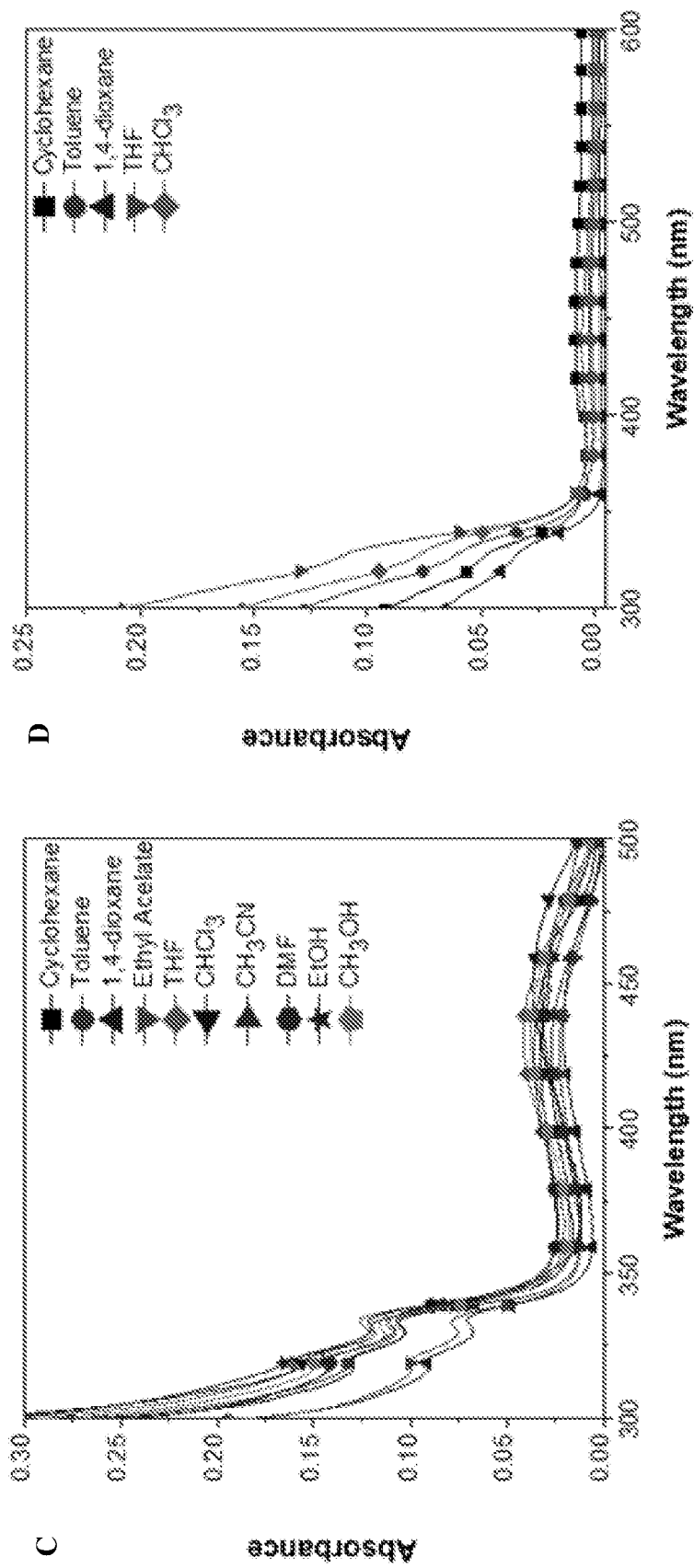
Figure 16:
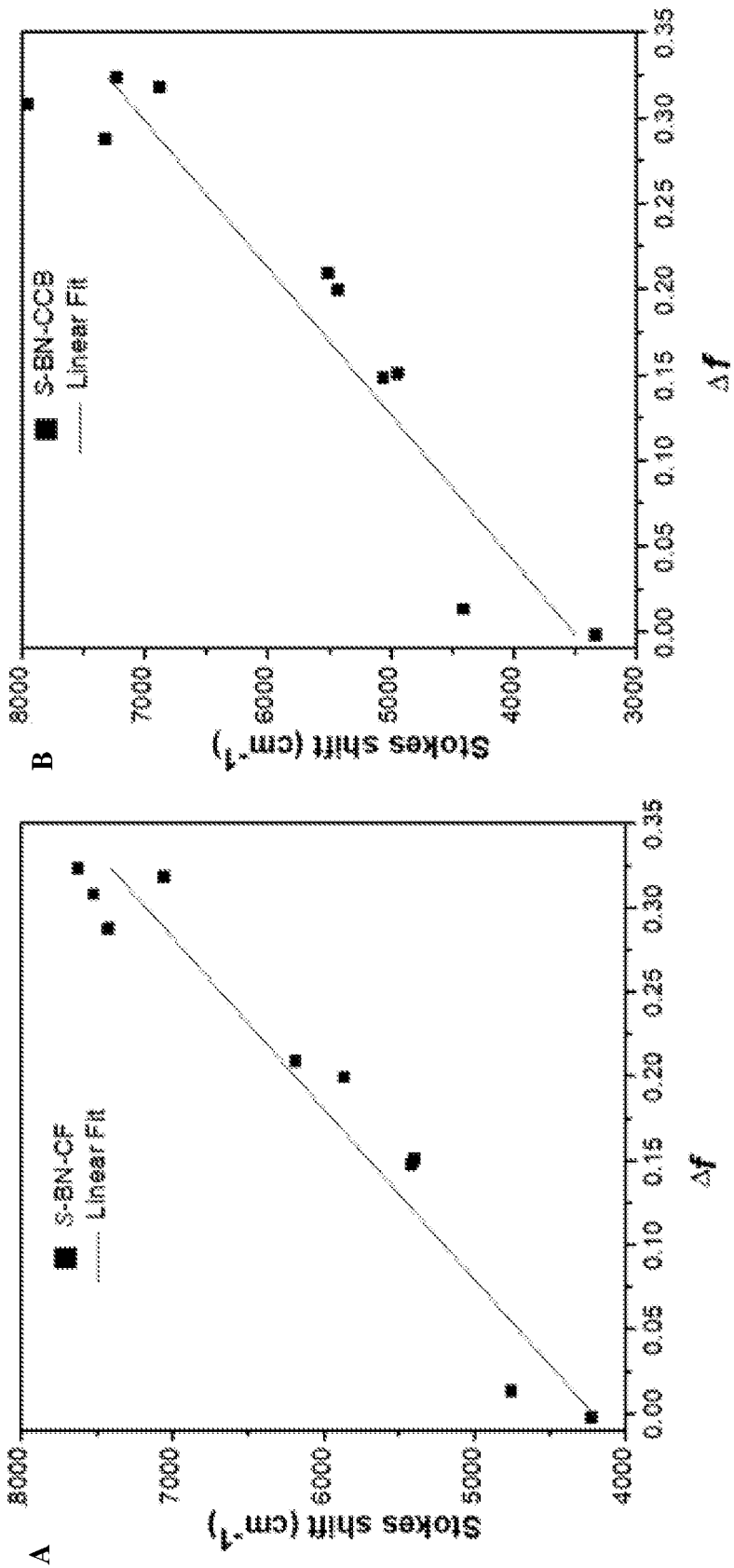
FIG. 16 depicts plots of Stokes shift versus Δf of the solvent. Δf is defined as the change of dipole moment of the solute between the ground and excited states for S-BN-CF (A), S-BN-CCB (B), S-BN-DCB (C) and S-BN-AF (D). Lippert-Mataga equation: $v_{abs}-v_{em}=2(\Delta\mu^2/hca^3)$ Δf+const. $v_{abs}$ ($v_{em}$) is the wavenumber of the absorption (fluorescence) maximum, h is the Planck constant, c is the light velocity, a is the radius of the Onsager cavity, and Δf=(ε−1)/(2ε+1)−($n^2$−1)/(2$n^2$+1), where E is the dielectric constant and n the refractive index of the solvent.
Figure 16:
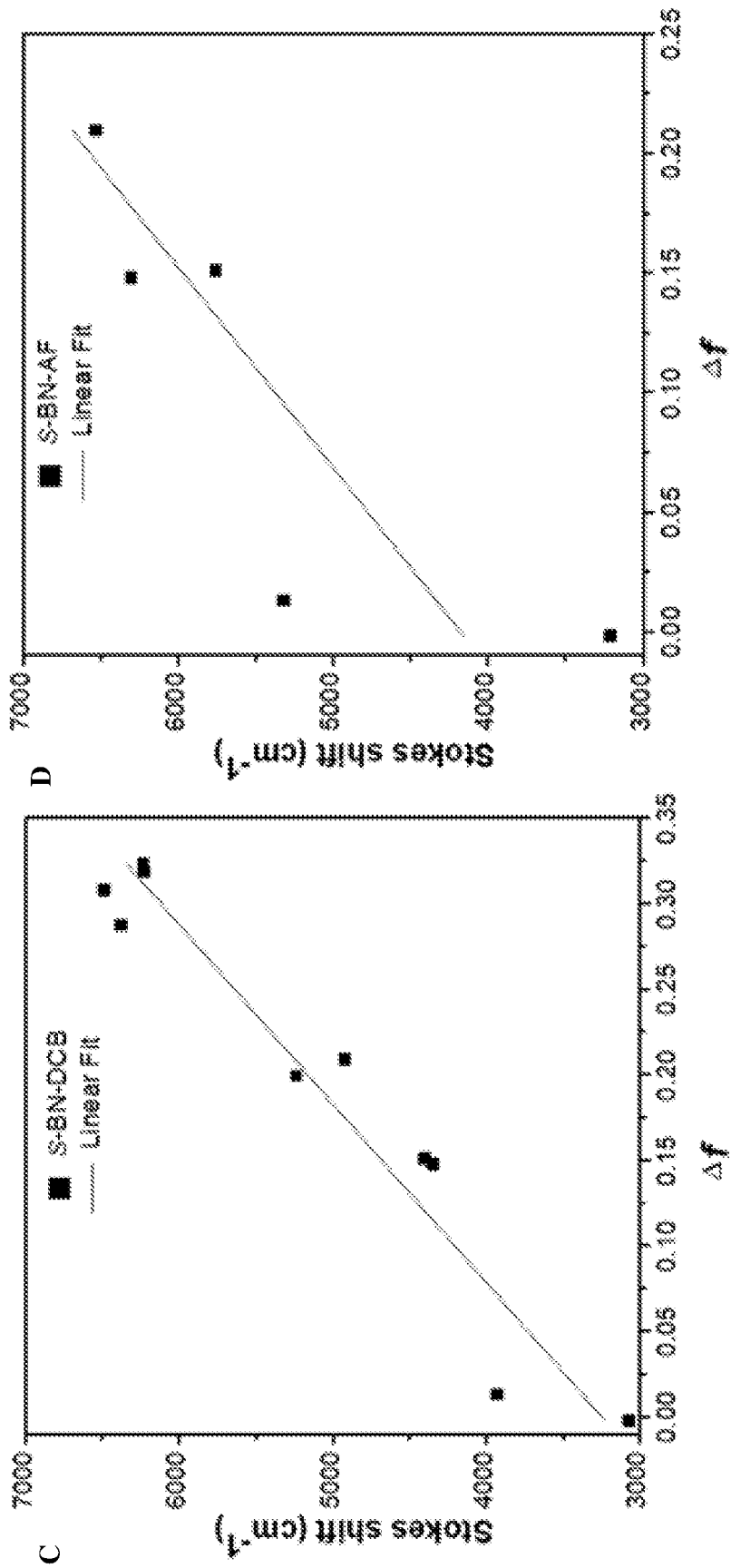
Figure 17:
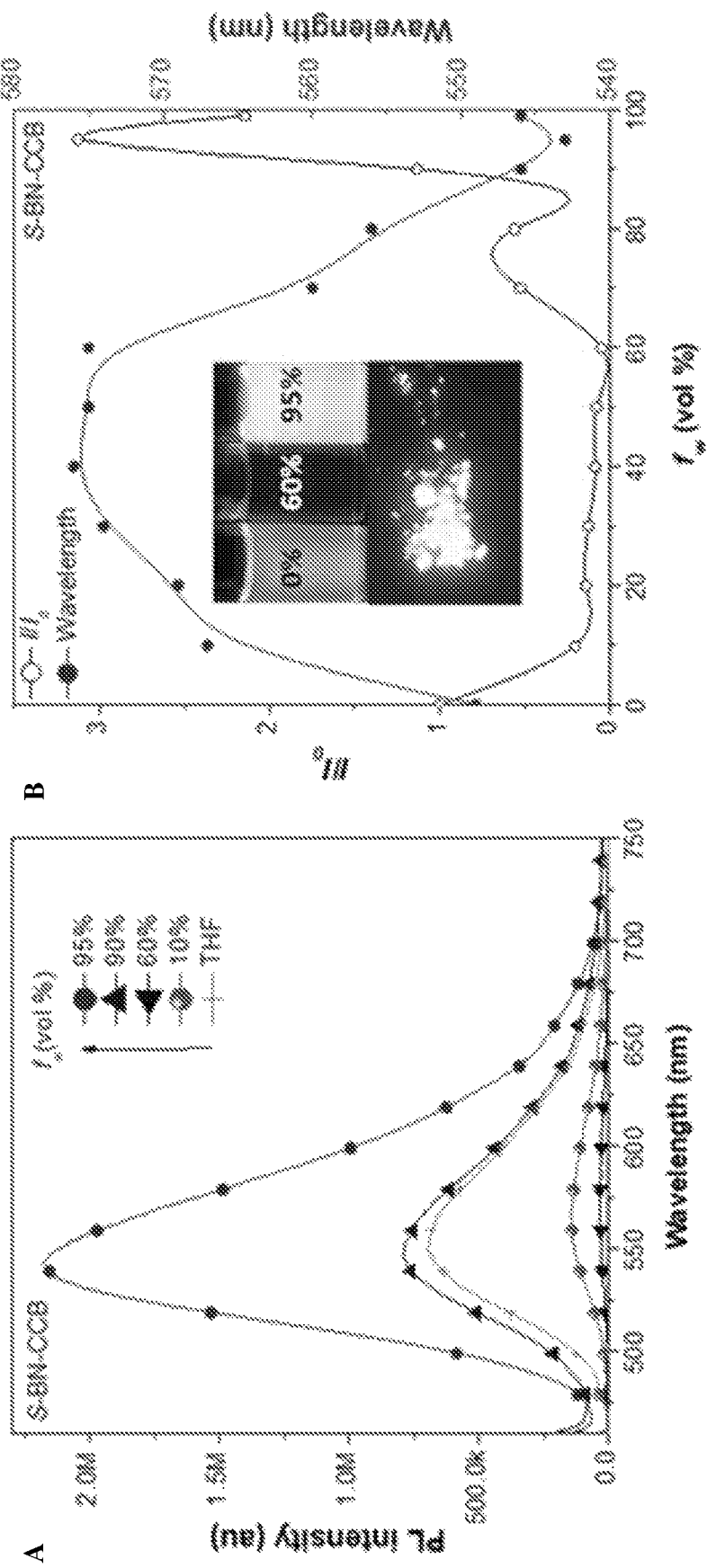
FIG. 17 depicts photoluminescence (PL) spectra of S-BN-CCB (A), S-BN-DCB (C) and S-BN-AF (E) in THF/$H_2O$ mixtures with different amounts of water ($f_w$=0%-99%). Plots of the PL peak intensity and emission wavelength vs the water fraction ($f_w$) for S-BN-CCB (B), S-BN-DCB (D)
Figure 17:
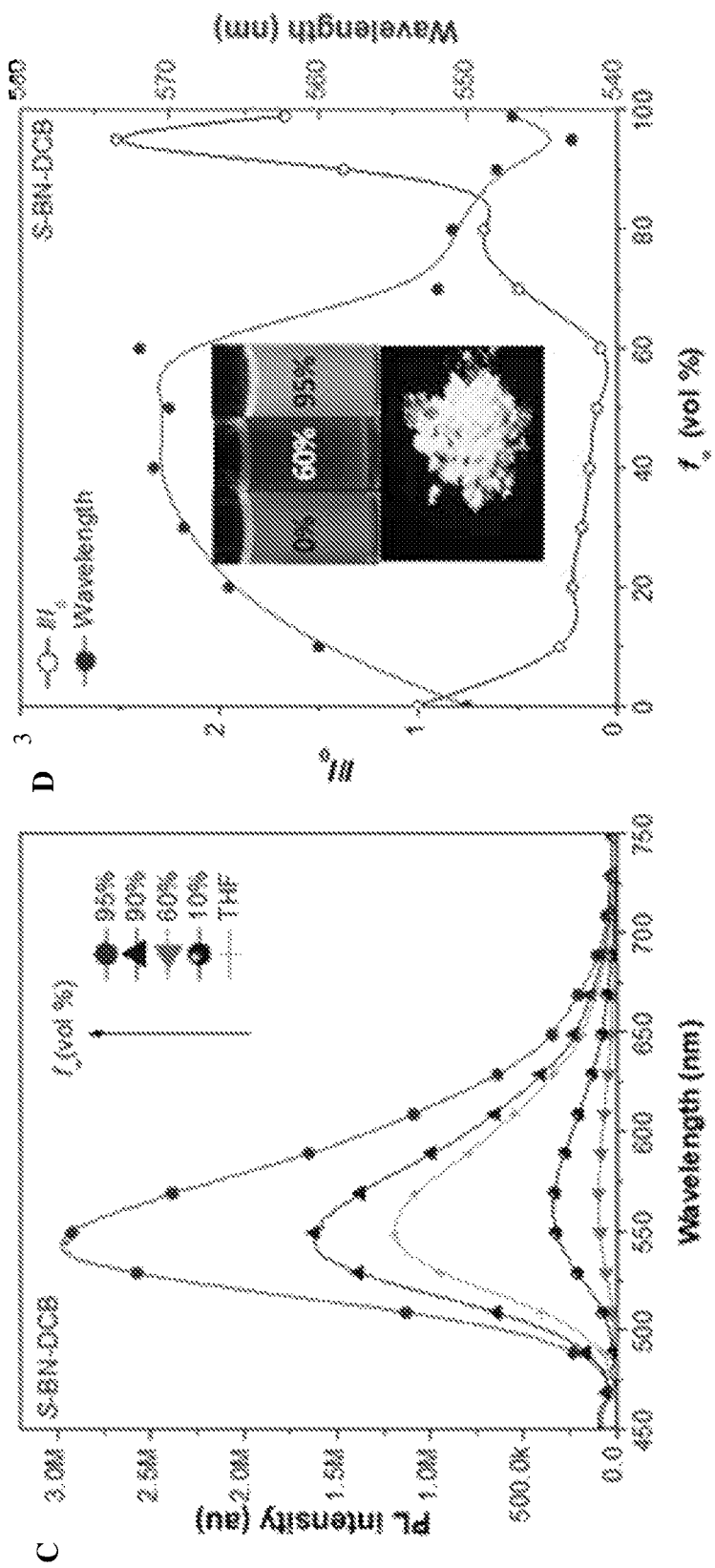
Figure 17:
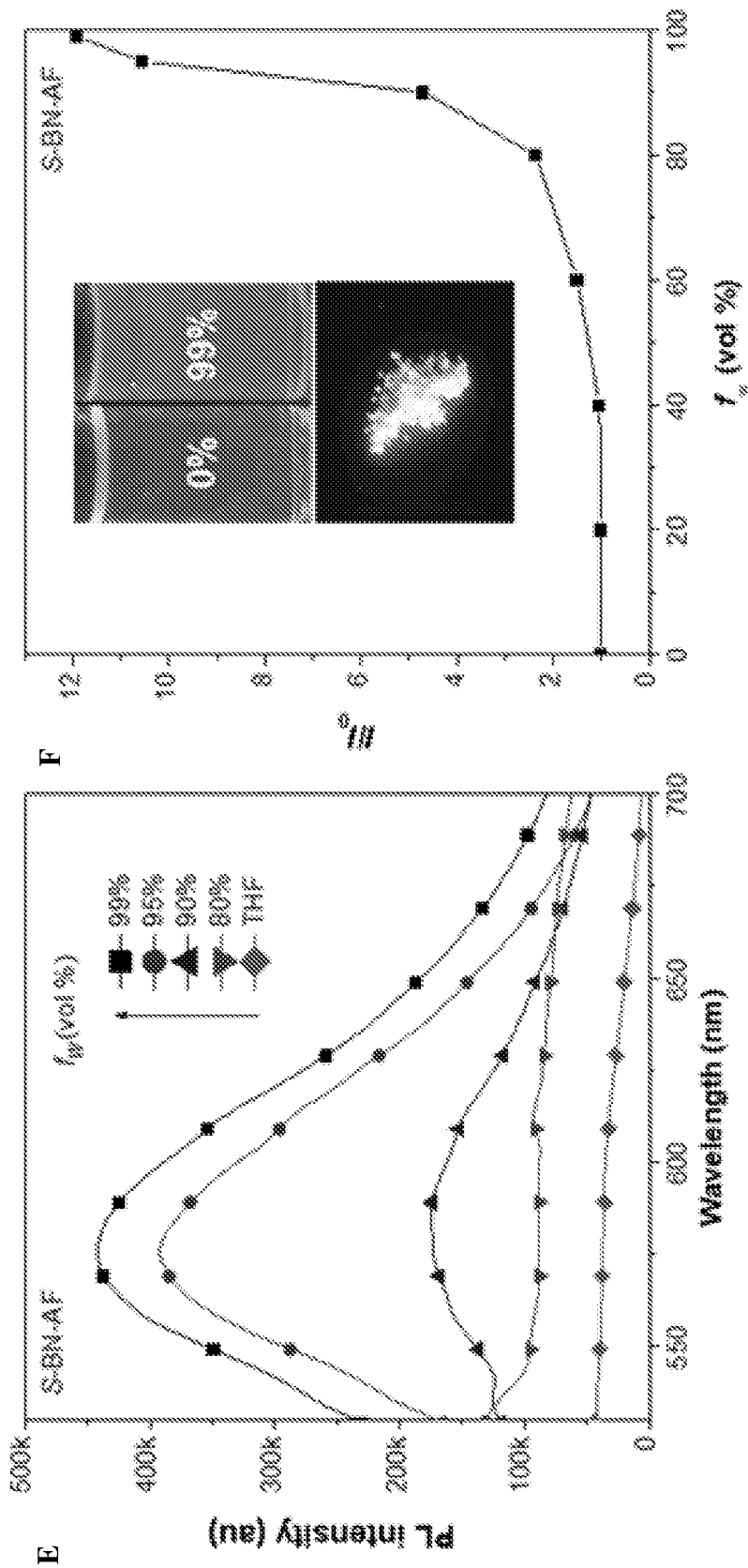

For a comprehensive investigation, the AIE and TICT properties of S-BN-CF, S-BN-CCB, S-BN-DCB and S-BN-AF were investigated in THF/$H_2O$ mixtures for different $f_w$ values. Taking the fluorescence spectra of S-BN-CF as an example (FIG. 2C), the fluorescence spectrum of S-BN-CF has an emission peak at 516 nm. By gradually increasing the water fraction ($f_w$) until the $f_w$=70%, the emission intensity decreases dramatically and a large red shift as high as 36 nm with the emission peak concerted at 552 nm was observed, demonstrating that S-BN-CF possesses the TICT property. The TICT effect was also supported by evaluating solvatochromic effects (FIG. 14, FIG. 15 and FIG. 16). The absorption spectra of S-BN-CF shows a slight change within scope of about 10 nm as the solvent polarity increases (FIG. 14A). While S-BN-CF's emission spectra present a remarkably red shift with the increase of the solvent polarity: from 480 nm in nonpolar cyclohexane to 552 nm in polar $CH_3OH$, indicating a typical charge transfer (CT) character in the excited state (FIG. 15A). The relationship between stokes shift and the solvent polarity parameter (Δf) of the exemplary compounds was investigated using the Lippert-Mataga equation. The slope of the fitted line is 9843 $cm^{-1}$ (FIG. 16A), which indicates a strong solvatochromic effect. When the water fraction ($f_w$) continues to increase from $f_w$=70% to $f_w$=99%, the emission intensity increases dramatically as high as 48 folds for S-BN-CF and a large blue shift as high as 46 nm with the emission peak concerted at 506 nm was observed (FIG. 2C and FIG. 2D). This phenomenon demonstrated that S-BN-CF possesses AIE properties. The other three molecules show similar emission behaviors (FIG. 17). The emission intensities of S-BN-CCB and S-BN-DCB can reach to 64.9 and 30.9-folds from $f_w$=60% to $f_w$=95%, respectively (FIG. 17). The emission intensities of S-BN-AF shows an enhancement of 11.9-fold from pure THF solution to $f_w$=99% of THF-water mixtures. The TICT and AIE property of the four molecules can also be observed by the fluorescence color images of their solutions obtained by a commercially available UV lamp (FIG. 2E). In addition, the AIE property was also proved by the fluorescence images of the solids. The other three exemplary compound's emission spectra also present a remarkable red shift further supporting a TICT effect with the increase of the solvent polarity: from 496 nm in nonpolar cyclohexane to 601 nm in polar $CH_3OH$ for S-BN-CCB, from 498 nm in nonpolar cyclohexane to 593 nm in polar $CH_3OH$ for S-BN-DCB, from 527 nm in nonpolar cyclohexane to 611 nm in polar $CHCl_3$ for S-BN-AF (FIG. 15). The normalized lines of S-BN-CCB, S-BN-DCB and S-BN-AF from the Lippert-Mataga equation were given in FIG. 16. S-BN-CCB, S-BN-DCB and S-BN-AF exhibited the slope of 11682, 9568 and 11960 $cm^{-1}$, respectively.

Figure 4:
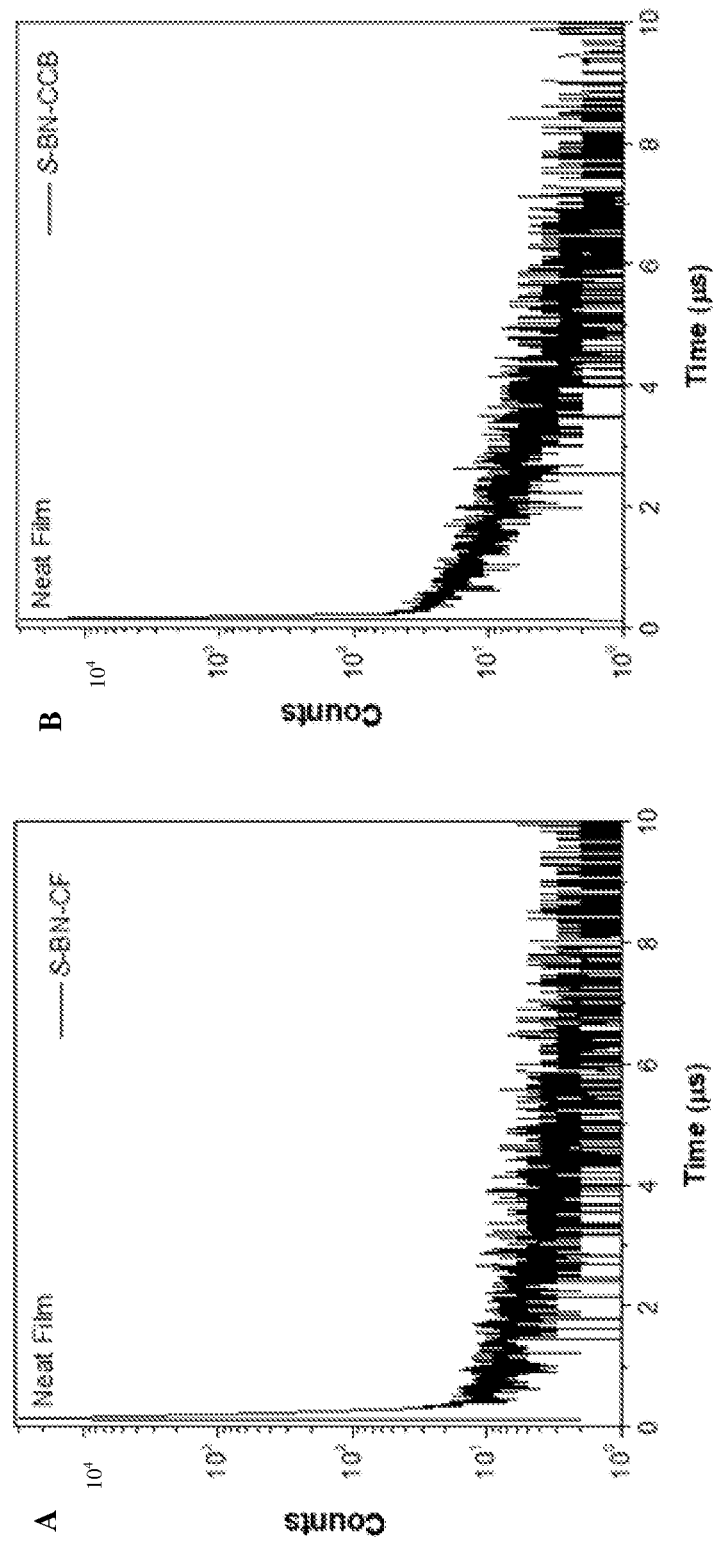
FIG. 4 depicts transient decay spectra of (A) S-BN-CF, (B) S-BN-CCB, (C) S-BN-DCB and (D) S-BN-AF in neat film and of (E) S-BN-CF, (F) S-BN-CCB, (G) S-BN-DCB and (H) S-BN-AF in doped film.
Figure 4:
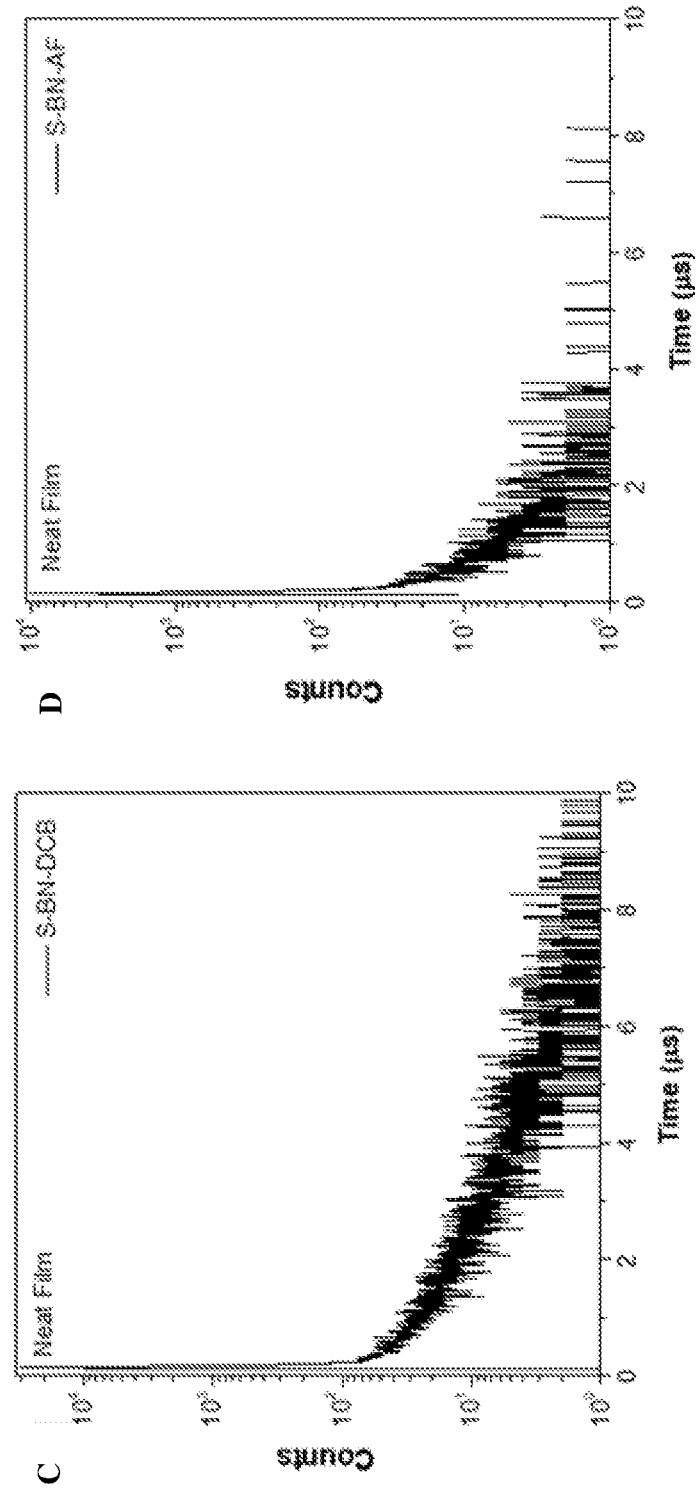
Figure 4:
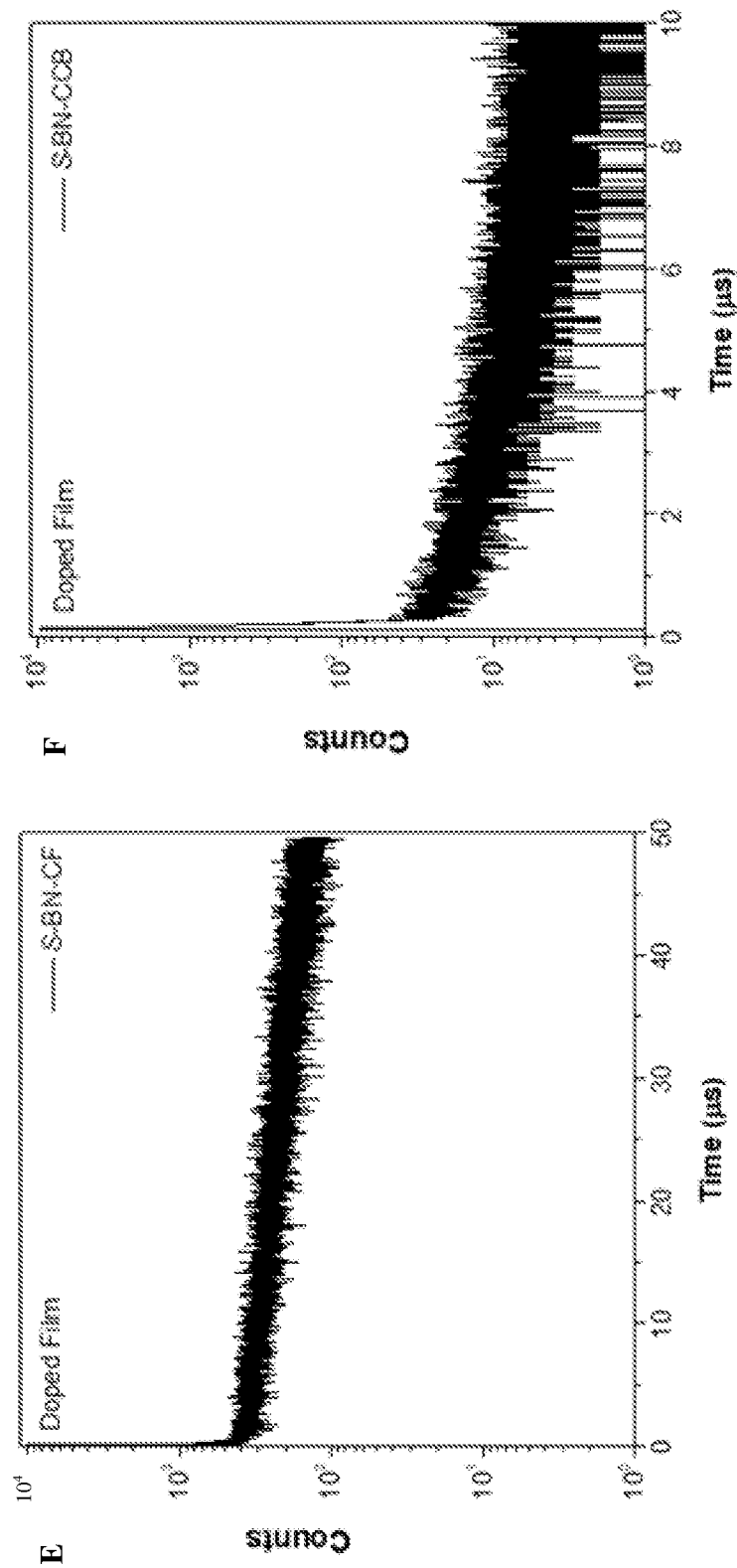
Figure 4:
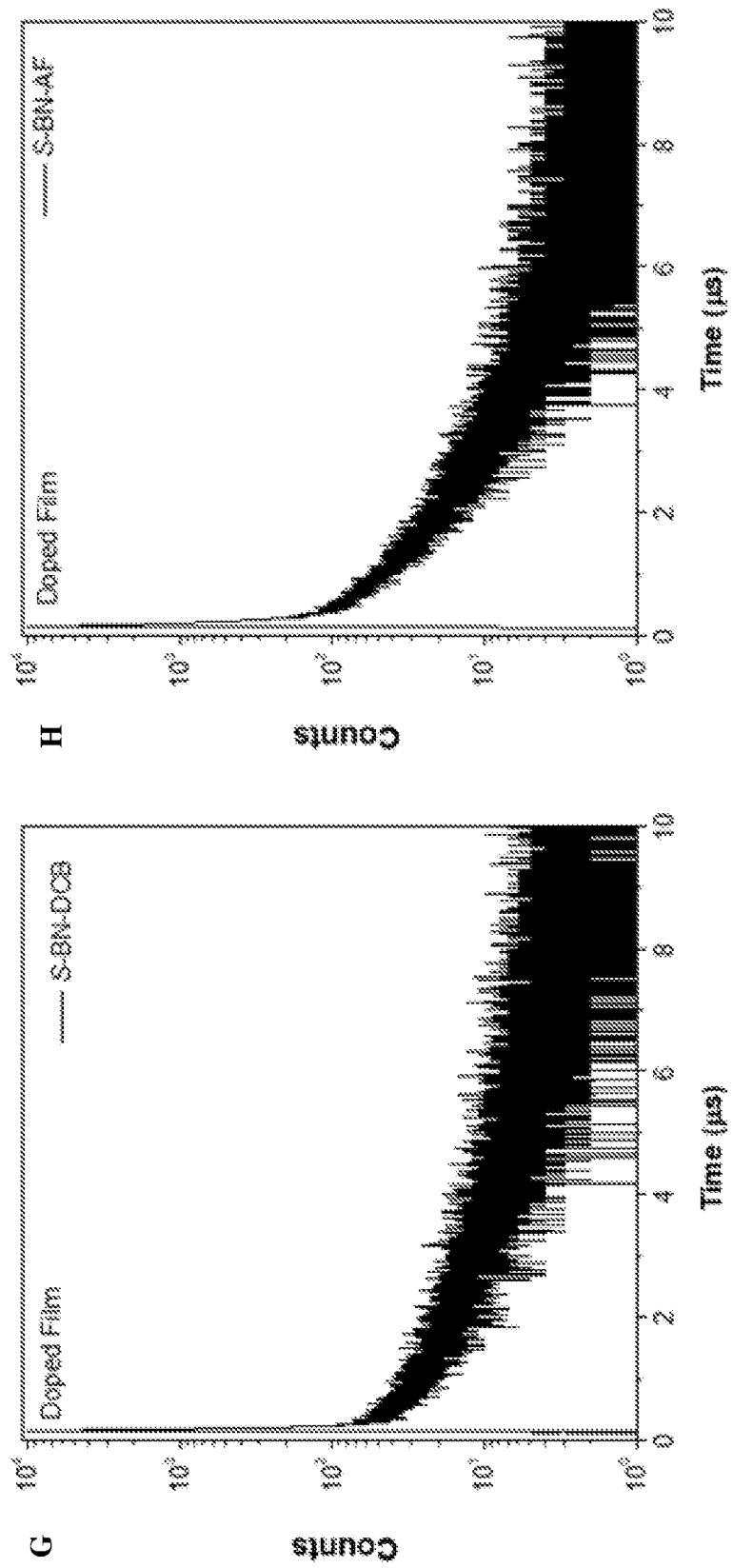

S-BN-CF, S-BN-CCB, S-BN-DCB and S-BN-AF show PL maximum in neat film at 520, 538, 553 and 580 nm, respectively (FIG. 19A). And their doped films in 1,3-bis (9H-carbazol-9-yl) benzene (mCP) host matrix show blue-shifted PL peaks at 493, 534, 540 and 571 nm, respectively (FIG. 19B). To deepen the understanding of the photophysical process, the transient fluorescence behaviors of neat and doped films of the exemplary compounds are investigated (FIG. 4). The neat and doped film of the exemplary compounds exhibit nanosecond-order prompt fluorescence with lifetimes ($\tau_{prompt}$) of 11.3-162.3 ns, and microsecond-order delayed fluorescence with lifetimes ($\tau_{delayed}$) of 0.4-24 μs [FIG. 4, Table 1 (FIG. 3) and Table 3 (FIG. 20)]. As illustrated in FIG. 22B, the emission intensities of the delayed components for doped film of S-BN-CF were intensified when the temperature is increased from 50 to 300 K. At ambient temperature (300 K), the overall $\Phi_{PL}$ of doped films are 32%, 12.5%, 45% and 38% with the quantum yields of delayed fluorescence components $\Phi_{delayed}$ are 32%, 5.6%, 23% and 18%, respectively. On the other hand, the overall $\Phi_{PL}$ of neat films are 39%, 5.3%, 22% and 20% with the quantum yields of delayed fluorescence components $\Phi_{delayed}$ are 1.2%, 0.59%, 2.5% and 3.0%, respectively. According to the Adachi's calculation method, the efficiencies of ISC ($\Phi_{ISC}$) and RISC ($\Phi_{RISC}$) of S-BN-CF based doped film can be calculated to be 98.9% and 32%, respectively [Table 3 (FIG. 20) and Table 4 (FIG. 21)]. This result indicates that only 1% of the initially generated $S_1$ excitons directly decay to emit prompt fluorescence, and nearly 99% of the $S_1$ excitons undergo ISC process and became $T_1$ excitons, meanwhile, 32% of thus formed $T_1$ excitons are up-converted into $S_1$ state by RISC process and efficiently emit delayed fluorescence. As for other exemplary compounds, the photophysical parameters of $\Phi_{ISC}$, $\Phi_{RISC}$, intersystem crossing rate constant ($k_{ISC}$), the reverse intersystem crossing rate constant ($k_{RISC}$) and the fluorescence decay rate ($k_F$), etc. in neat films and doped films are also summarized in Table 4 (FIG. 21). These results imply that the efficient RISC process from $T_1$ to $S_1$ are observed in these exemplary compounds.

Chiroptical

The CD spectra of R/S-BN-CF, R/S-BN-CCB, R/S-BN-DCB and R/S-BN-AF in toluene solution and neat film were also investigated. As is evident from FIG. 5A-D, the molecules show similar Cotton effects. In addition, we also found that the exemplary compounds exhibited mirror-image CD band. The strong Cotton effect in short wavelength region at 300 and 330 nm can be assigned to the characteristic absorption of chiral binaphthyl moieties. Meanwhile the exemplary compounds can exhibit a Cotton effect in the region from 400 to 500 nm, which is assigned to the absorption of the D-A electronic structures of exemplary compounds, indicating that the chirality is transmitted from the binapthyl group to the achiral Cz and DMAC moiety. To further quantify the absolute CD magnitude, Kuhn's dimensionless anisotropy factor in the ground state ($g_{abs}$) was employed. The average $|g_{abs}|$ values for R/S-BN-CF, BN-CCB, BN-DCB and BN-AF were $1.1 \times 10^{-3}$ (302 nm), $1.1 \times 10^{-3}$ (324 nm), $1.0 \times 10^{-3}$ (334 nm) and $1.3 \times 10^{-3}$ (301 nm), respectively. The $|g_{abs}|$ values of the exemplary compounds at the longer wavelength region of $7.6 \times 10^{-4}$ (405 nm), $2.4 \times 10^{-4}$ (450 nm), $4.5 \times 10^{-4}$ (440 nm) and $4.5 \times 10^{-4}$ (436 nm) for R/S-BN-CF, BN-CCB, BN-DCB and BN-AF were also calculated. The calculated values can be associated with the absorption transition of D-A electronic structures, also suggesting the occurrence of effective chirality transfer from the chiral BINOL skeleton to the whole conjugated molecule. Interestingly, when the neat film of the exemplary compounds were fabricated by vacuum deposition, CD signal enhancement response could be observed as demonstrated in FIG. 5E-H. We also confirmed that the $g_{abs}$ value of these molecules (FIG. 23), which indicates chiroptical amplification.

Figure 6:
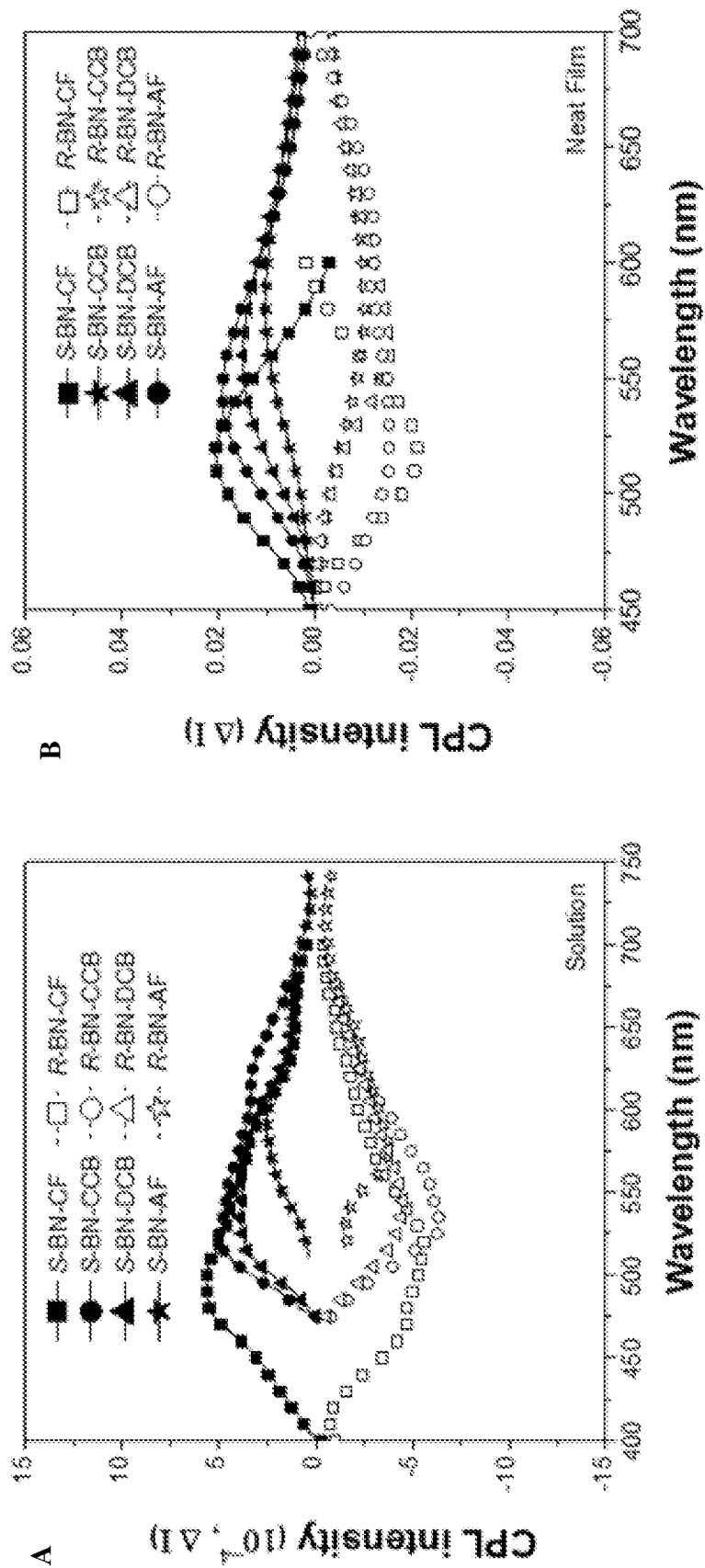
FIG. 6 depicts CPL spectra of R/S-BN-CF, R/S-BN-CCB, R/S-BN-DCB and R/S-BN-AF in toluene (A) (1.0×$10^{-5}$ mol/L, $\lambda_{ex}$=340 nm for R/S-BN-CF and R/S-BN-AF, $\lambda_{ex}$=370 nm for R/S-BN-CCB, R/S-BN-DCB) and in neat film (B). $g_{PL}$ of S-BN (C) and R-BN (D) in solution of toluene and in neat film. The $g_{PL}$ values were calculated from FIGS. 6A and 6B at the maximum emission wavelength.
Figure 6:
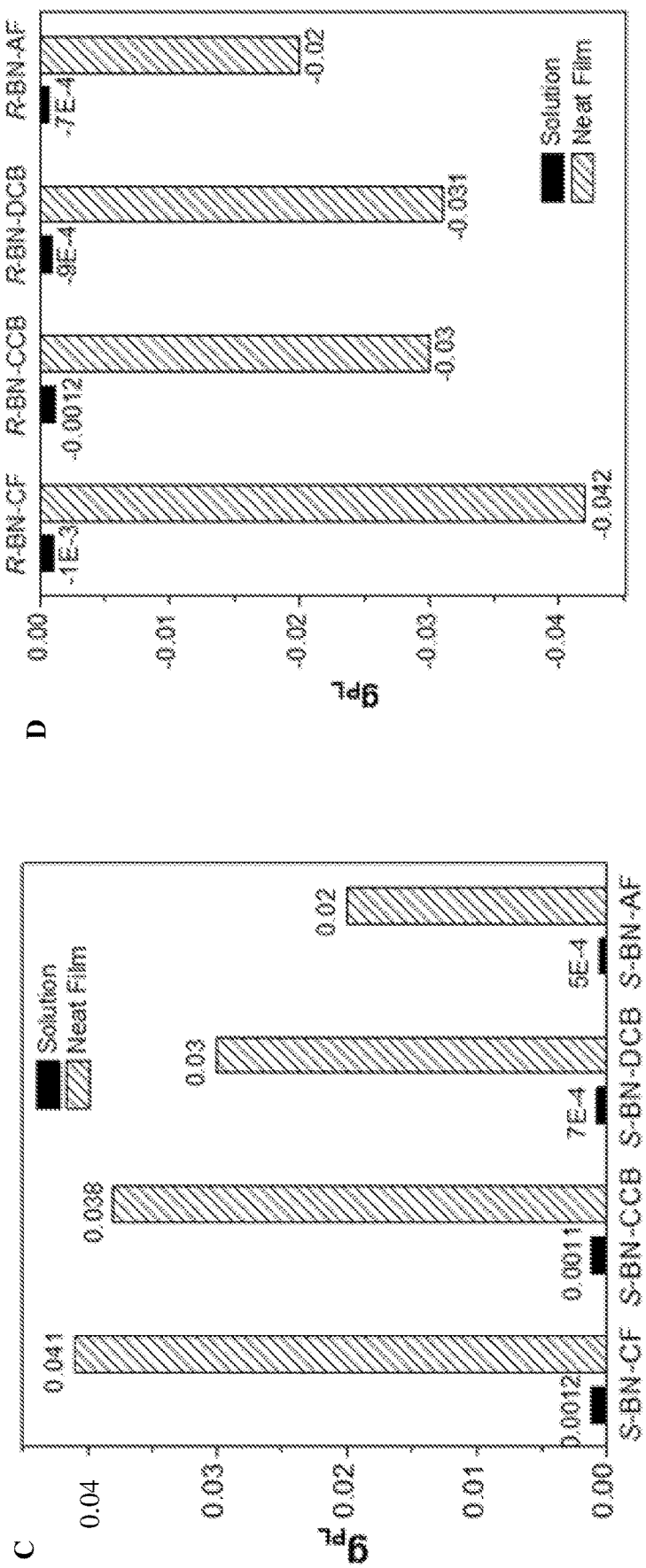

CPL is the emission analog of CD that reflects the chiroptical properties of the luminescent molecules upon excitation. FIGS. 6A and 6B show the CPL spectra of the exemplary compounds in toluene and neat film. The exemplary compound enantiomers can exhibit clear mirror-image CPL signals in a solution of toluene with the luminescence dissymmetry factor ($|g_{lum}|$) values of 0.0005-0.0012. In certain embodiments, compounds of Formula I exhibit luminescence dissymmetry factor ($|g_{lum}|$) values of 0.0005-0.0012, 0.0007-0.0012, or 0.0011-0.0012 in solution. However, when the neat films fabricated by these enantiomers were independently measured using a JASCO CPL-300, the larger average $|g_{lum}|$ values of 0.020 to 0.042 could be observed (FIG. 6C and FIG. 6D). In certain embodiments, compounds of Formula I exhibit luminescence dissymmetry factor ($|g_{lum}|$) values of 0.020 to 0.042, 0.03-0.042, or 0.038-0.042 in a neat film. Therefore, chiroptical amplification of the excited state could be also observed in neat film.

CPOLEDs Performance

Figure 7:
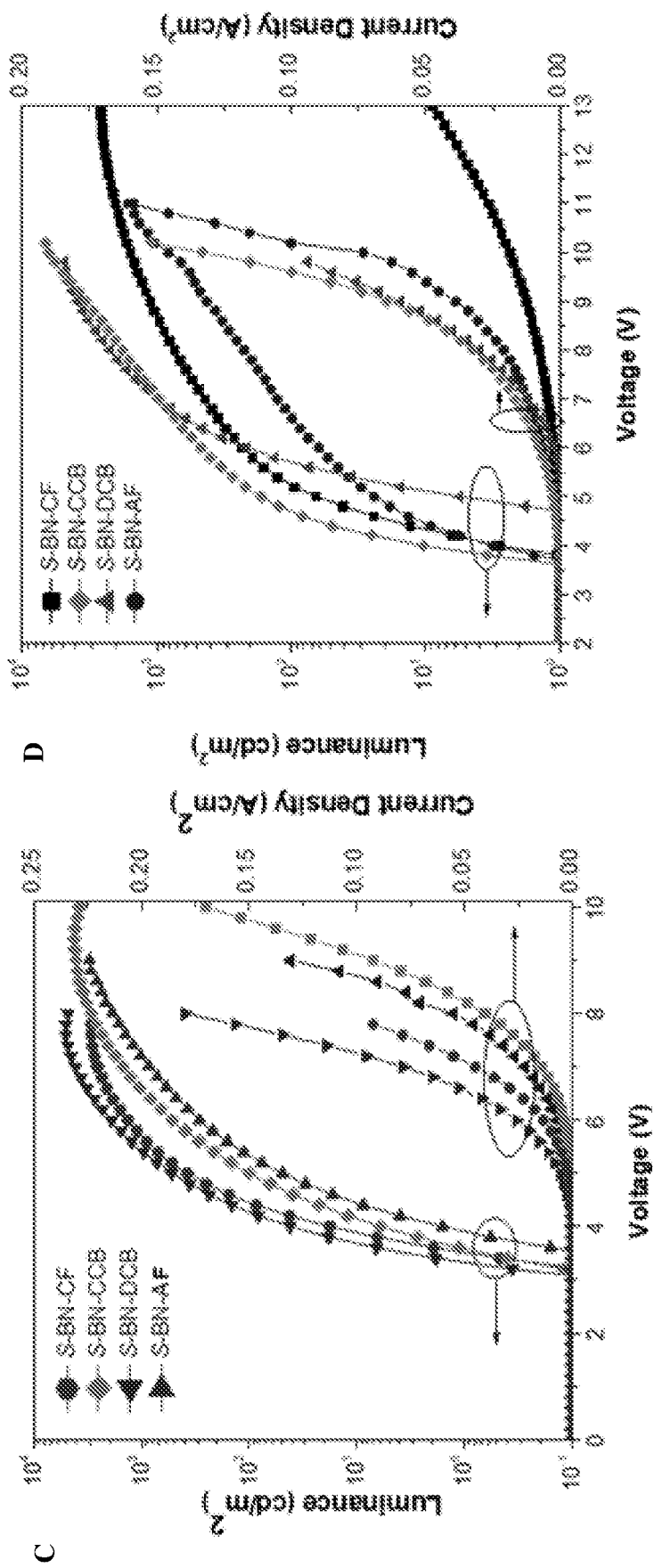
FIG. 7 depicts electroluminescence (EL) spectra of CPOLED featuring multicolor emission taken at 5 V for doped films (A) and neat films (B). Current density-voltage-luminance (J-V-L) characteristics for CPOLEDs for doped films (C) and neat films (D). External EL quantum efficiency ($\eta_{ext}$) versus current density plots for chiral AIEgens-based CPOLEDs for doped films (E) and neat films (F).
Figure 7:
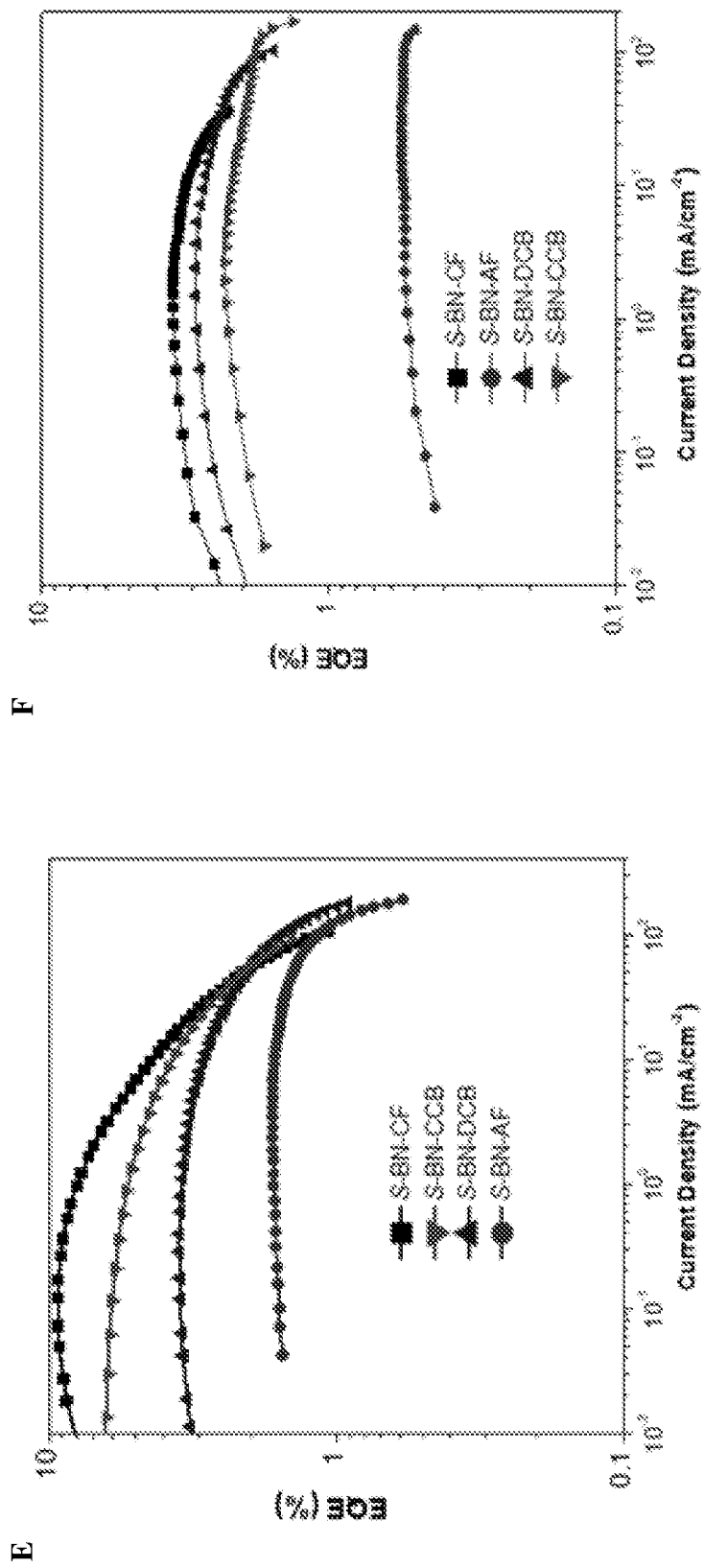

Inspired by the efficient RISC, delayed fluorescence characteristics, high 'glum' value in film (~$10^{-2}$) and excellent chiroptical properties, the development of the exemplary compounds' promising application as the emitters in circularly polarized electroluminescent devices was investigated. Initially, S-BN-CF was chosen to optimize the device structure due to its high $k_{RISC}$ ($3.867 \times 10^6$ $s^{-1}$) in doped film among the exemplary compounds. The performance of an electroluminescent device comprising a film doped with S-BN-CF were evaluated by fabricating OLEDs with the following device configuration: (ITO)/HATCN (10 nm)/TAPC:HATCN (5:2, 60 nm)/TCTA (20 nm)/mCP: 10% S-BN-CF (20 nm)/BmPyPB (10 nm)/BmPyPB: 8% Liq (40 nm)/Liq (1.5 nm)/(Al). In the exemplary CPOLED device HATCN (dipyrazino[2,3-f:2',3'-h]quinoxaline-2,3,6,7,10,11-hexacarbonitrile) and 8-hydroxyquinolinolato-lithium (Liq) serve as the hole-injection layer and the electron-injection layer, respectively, TCTA (tris(4-(9H-carbazol-9-yl)phenyl)amine) and TAPC (4,4'-(cyclohexane-1,1-diyl) bis(N,N-di-p-tolylaniline)) serve as the hole-transport layer (HTL), BmPyPhB (3,3'',5,5''-tetra(pyridin-3-yl)-1,1':3',1''-terphenyl) serves as the electro-transport layer (ETL), and 1,3-di(9H-carbazol-9-yl)benzene (mCP) acts as a host matrix. The details of device structures are illustrated in FIG. 24 together with the chemical structures of the exemplary materials used in the construction of the device are depicted in FIG. 24B. The S-BN-CF doped device displays bright green EL emission with the peak at the 496 nm for doped film (FIG. 7A), and the Commission Internationale de l'Éclairage (CIE) color coordinates of (0.247,0.472) is attained (FIG. 25A). FIG. 7C shows that the current-voltageluminance (J-V-L) characteristics of the fabricated OLEDs. The EL spectra show little change under different voltages, indicating that the S-BN-CF based device exhibits excellent spectral stability (FIG. 26A). Furthermore, the S-BN-CF doped device is turned on at a low voltage of 3.6 V, suggesting the efficient carrier injection and transport into S-BN-CF. The maximum luminance ($L_{max}$), current ($\eta_c$), power efficiency ($\eta_p$) and external quantum ($\eta_{next}$) efficiencies are as high as 2948 cd m$^{-2}$, 24.58 cd A$^{-1}$, 19.55 lm W$^{-1}$ and 9.31%, respectively, which is the highest performance level among the reported CPOLEDs. The high $\eta_{ext}$ obtained in the device should be attributed to the high $\Phi_{ISC}$ (99%) and $\Phi_{RISC}$ (32%) [Table 3 (FIG. 20)], which indicated that almost all $S_1$ excitons could be converted into $T_1$ excitons and about 32% $T_1$ excitons could be up-converted into $S_1$ excitons and utilized for EL emission, resulting in high $\eta_{ext}$. In certain embodiments, the maximum power efficiency ($\eta_p$) of 9.1 to 19.6 or 18.2 to 19.6. However, under the luminescence of 1000 cd m$^{-2}$, the device possesses performances with CE of 11.49 cd A$^{-1}$ and EQE of 4.4% [Table 2 (FIG. 8)], which demonstrates the large efficiency roll-off for doped film. In addition, the BN-CCB, BN-DCB and BN-AF of doped films based devices can emit EL emission with the peak centered at 527, 547 and 571 nm, respectively. The multicolor electroluminescence from 493 nm to 571 nm based CPOLEDs for doped film were achieved by altering donor unites.

In a set of comparable experiments, nondoped OLEDs were fabricated (Device E-H) with the following device configuration: (ITO)/HATCN (10 nm)/TAPC (60 nm)/mCP (10 nm)/Enantiomers (20 nm)/BmPyPB (50 nm)/Liq (2.5 nm)/Al for CPOLEDs characteristics. The BN-CF, BN-CCB, BN-DCB and BN-AF nondoped based devices can emit EL emission with the peaks centered at 537, 563, 550 and 597 nm, respectively. The maximum luminance ($L_{max}$), current ($\eta_c$), and external quantum ($\eta_{ext}$) efficiencies are 2570 cd m$^{-2}$, 10.28 cd A$^{-1}$ and 3.51% for BN-CF, 6633 cd m$^{-2}$, 6.33 cd A$^{-1}$ and 2.31% for BN-CCB, 5729 cd m$^{-2}$, 8.73 cd A$^{-1}$ and 2.93% for BN-DCB, 1473 cd m$^{-2}$, 1.09 cd A$^{-1}$ and 1.56% for BN-AF, respectively. In certain embodiments, the maximum luminance of a electroluminescent device comprising a nondoped film of the compound of Formula I is ($L_{max}$) is 1,473 to 6,633, 2,570 to 6,633, 2,948 to 6,633, 3,032 to 6,633, 4,199 to 6,633, or 5,056 to 6,633 cd m$^{-2}$. In certain embodiments, the external quantum ($\eta_{ext}$) efficiency of the electroluminescent device comprising a nondoped film of the compound of Formula I is 0.6 to 9.3, 1.7 to 9.3, 2.3 to 9.3, 2.9 to 9.3, 3.5 to 9.3, or 6.3 to 9.3%. Importantly, the nondoped OLEDs can retain high EL efficiencies as luminescence increases. For example, at 1000 cd m$^{-2}$, the $\eta_c$, $\eta_p$ and $\eta_{ext}$ are 9.1 cd A$^{-1}$, 3.2 lm W$^{-1}$ and 3.1%, respectively, which are almost the same as the maximum values. The roll-off of current efficiency for nondoped OLED is 11.7% which is much smaller than the roll-off value of 53.3% for doped OLED [Table 2 (FIG. 8)]. The small roll-off value should be arisen from the feature of AIE characteristic.

Figure 9:
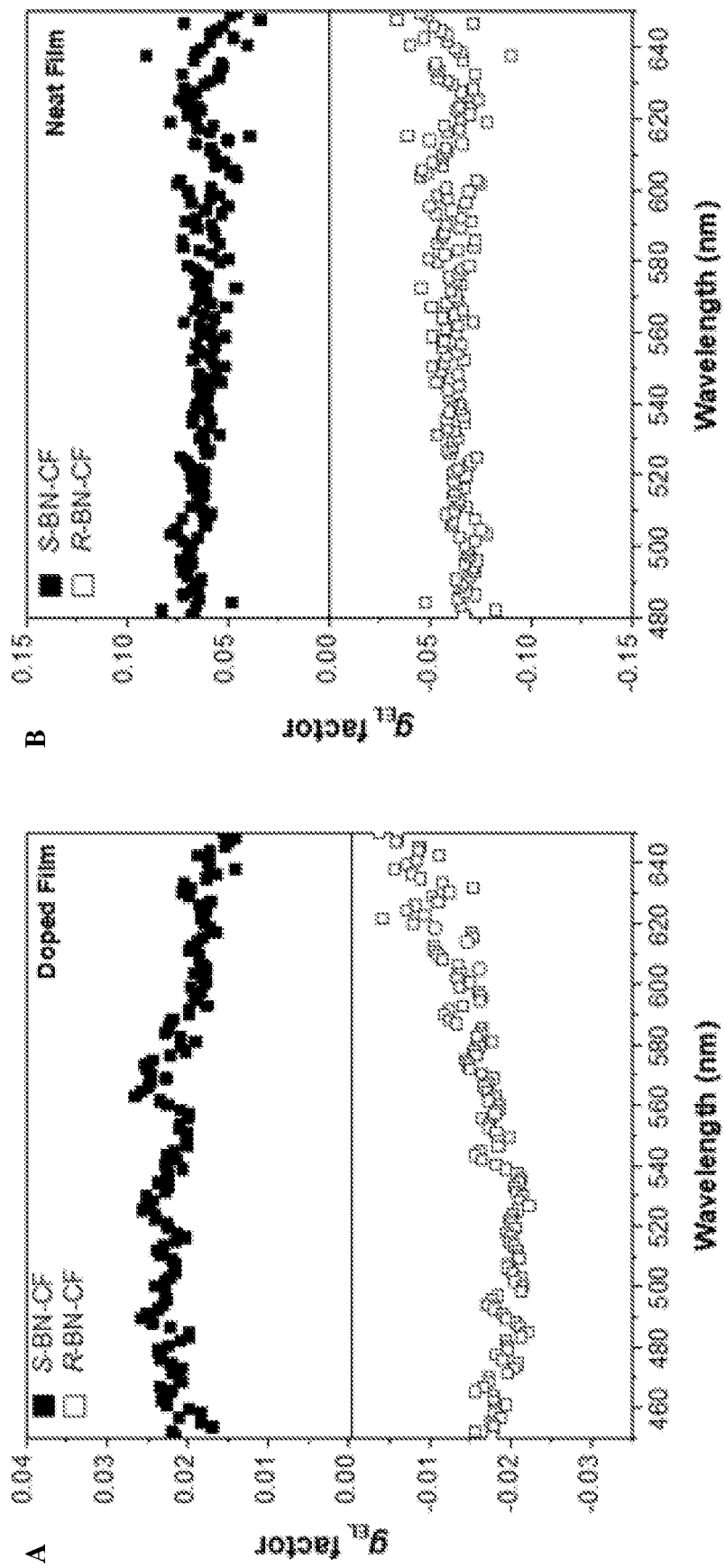
FIG. 9 depicts $g_{EL}$ of R/S-BN-CF as a function of emission wavelength in doped film (A) and in neat film (B). $g_{EL}$ of S-BN-CF, S-BN-CCB, S-BN-DCB and S-BN-AF (C), R-BN-CF, R-BN-CCB, R-BN-DCB and R-BN-AF (D) in doped film and neat film. The $g_{EL}$ values were calculated at the maximum emission wavelength.
Figure 9:
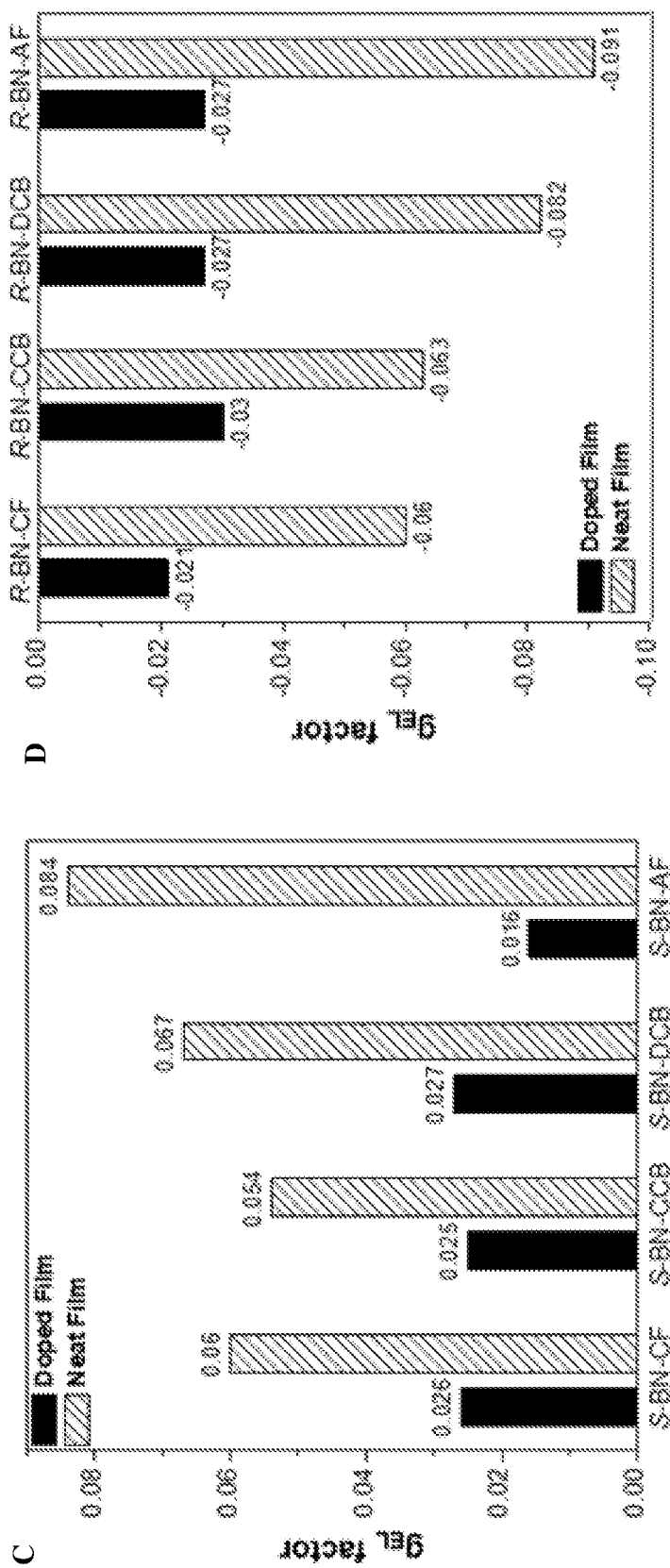

To compare the g-factors of the both enantiomers of BN-CF, we investigated the CPEL characteristic of the enantiomers' devices. The obtained left or right-circularly polarized electroluminescence spectra were taken under the voltage of 6 V. The two different enantiomers resulted in circularly polarized emission with opposite $g_{EL}$ signs, indicating that the chiral BINOL skeleton is responsible for the observed CP effect. At the emission maximum of 496 nm, the $g_{EL}$ of enantiomers doped based devices were +0.026 for S-BN-CF and −0.021 for R-BN-CF, respectively (FIG. 9). Whereas the obtained $g_{EL}$ values were not higher than reported polymer-based CPOLED, this is the first example of small chiral organic molecules based CPOLED and the higher EQE. Inspired by the preliminary results, we further investigated the CPEL characteristic of other enantiomers, such as R/S-BN-CCB, BN-DCB and BN-AF. The $g_{EL}$ of enantiomers based doped devices were +0.025, +0.027, +0.016 for S-BN-CCB, S-BN-DCB, S-BN-AF and −0.030, −0.027, −0.027 for R-BN-CCB, R-BN-DCB and R-BN-AF, respectively (FIG. 9C and FIG. 9D, FIG. 29). In certain embodiments, the electroluminescent device comprising doped thin films comprising the compound of Formula I is ±0.016 to ±0.027 or ±0.021 to ±0.03. Interestingly, the larger |$g_{EL}$| values were found in neat films. The $g_{EL}$ of enantiomers based devices were +0.060, 0.054, +0.067, +0.084 for S-BN-CF, BN-CCB, BN-DCB, BN-AF and −0.060, −0.063, −0.082, −0.091 for R-BN-CF, BN-CCB, BN-DCB and BN-AF, respectively (FIG. 9C, FIG. 29).). In certain embodiments, the electroluminescent device comprising nondoped thin films comprising the compound of Formula I is ±0.054 to ±0.084, ±0.06 to ±0.084, or ±0.067 to ±0.084. These data also demonstrate that the chiroptical amplification of the excited state could be also achieved in neat film (aggregated state) for circularly polarized electroluminescence. The chiroptical amplification may be attributed to the the population of chiral aggregates in neat film.

In view of electroluminescent devices described herein, there are only 11 papers published since 1997 to now, and the relevant key data of the devices are listed in Table 5 (FIG. 31). Whereas the electroluminescence dissymmetry factor ($g_{EL}$) +0.026/−0.021 and +0.06/−0.06 for doped film and neat film were not higher than reported polymer based CP devices, the EQE as high as 9.3% and 3.5% for doped film and neat film were the firstly reported CP device so far. And the efficiency roll-off arisen from AIE feature is firstly investigated in the CPOLED research areas.

Examples

All solvents and reagents were commercially available and analytical-reagent-grade. DMF was purified by distillation over calcium hydride in the presence of benzophenone.

$^1$H and $^{13}$C NMR spectra were measured on a Bruker ARX 400 NMR spectrometer and reported as parts per million (ppm) from the internal standard TMS. High-resolution mass spectra (HR-MS) were obtained on a Finnigan MAT TSQ 7000 Mass Spectrometer System operated in a MALDI-TOF mode. Single crystal data was collected on a Bruker Smart APEXII CCD diffractometer using graphite monochromated Cu Kα radiation (λ=1.54178 Å). The photos and videos were recorded by a Cannon EOS 60D. Thermogravimetric analysis (TGA) was performed on a TA TGA Q5000 under nitrogen at a heating rate of 10° C. min$^{-1}$. Differential scanning calorimetry (DSC) analysis was performed on a TA Instruments DSC Q1000 at a heating rate of 10° C. min$^{-1}$. Electrochemical measurements were performed on a CHI610D electrochemical workstation in a three-electrode cell using a platinum button as working electrode, a platinum wire as counter electrode and a saturated calomel electrode as reference electrode in CH$_3$CN solution with 0.1 M Bu$_4$N$^+$PF$_6^-$ at a scan rate of 100 mV/s and ferrocene as internal standard.

Absorption spectra were measured on a Milton Roy Spectronic 3000 Array spectrophotometer. Steady-state photoluminescence (PL) spectra were measured on a Perkin-Elmer spectrofluorometer LS 55. The lifetime and temperature dependent photoluminescence spectra and absolute luminescence quantum yield were measured on a Edinburgh FLSP 920 fluorescence spectrophotometer equipped with a xenon arc lamp (Xe900), a microsecond flash-lamp (uF900), a picosecond pulsed diode laser (EPL-375), a closed cycle cryostate (CS202*I-DMX-1SS, Advanced Research Systems) and an integrating sphere (0.1 nm step size, 0.3 second integration time, 5 repeats), respectively. Mean decay times ($\tau_P$) were obtained from individual lifetimes $\tau_i$ and amplitudes $a_i$ of multi-exponential evaluation. Circular dichroism (CD) spectra were recorded with a Chirascan spectrometer (Applied Photophysics, England). Circularly polarized photoluminescence (CPPL) spectra of the films and solution were recorded at 50 nm min$^{-1}$ scan speed with a commercialized instrument JASCO CPL-300 at room temperature with the resolution of 15 nm. Circularly polarized photoluminescence (CPEL) spectra were recorded on an instrument according to literature procedures.[1] Left-handed and right-handed CP emission spectra from the thin films were collected using a linear polarizer and quarter-wave plate prior to an Ocean Optics Fiber Flame-S-VIS-NIR spectrophotometer.

The crystalline samples of R-BN-CF and S-BN-DCB were obtained from slowly evaporative crystallization using hexane/acetate mixture (10:1, v/v). The crystalline sample of S-BN-AF were obtained from slowly evaporative crystallization using $CH_2Cl_2/C_2H_5OH$ mixture (1:5, v/v).

Preparation of R/S-BN-CF

A mixture of R/S-1 (1.0 g, 2.24 mmol), carbazole (374 mg, 2.24 mmol) and $K_2CO_3$ (464 mg, 3.36 mmol) was dissolved in anhydrous DMF (30 mL). The mixture was stirred for 3 h at room temperature. And then water (60 mL) was added. The mixture was extracted with ethyl acetate (3×30 mL). The combined organic layers were dried with anhydrous $Na_2SO_4$ and evaporated under reduced pressure to obtain the crude product. The residue was purified by silica gel column chromatography (hexane/ethyl acetate=10:1) to yield 980 mg (74%) of the product as a yellow powder after removal of the solvent. $^1$H NMR (400 Hz, $CDCl_3$): δ 8.20-8.04 (m, 4H), 8.06 (dd, $J_1$=8.0 Hz, $J_2$=5.2 Hz, 2H), 7.71-7.60 (m, 4H), 7.57-7.37 (m, 8H), 7.20 (d, J=8.0 Hz, 1H), 7.13 (d, J=7.6 Hz, 1H). $^{13}$C NMR (100 Hz, $CDCl_3$): δ 156.9, 154.2, 150.95, 150.92, 149.3, 149.0, 148.56, 148.53, 139.86, 139.82, 132.5, 132.4, 132.04, 132.00, 131.89, 131.83, 128.6, 127.7, 126.75, 126.73, 126.69, 126.65, 124.94, 124.90, 124.41, 124.35, 124.31, 121.8, 120.91, 120.87, 120.35, 120.26, 113.45, 113.42, 111.08, 111.05, 109.56, 109.54, 109.3, 103.2, 103.1. HRMS (MALDI-TOF, m/z): [M]$^+$ calcd for $C_{40}H_{20}FN_3O_2$, 593.1540. found, 593.1524.

Preparation of R/S-BN-CCB

A mixture of R/S-BN-CF (1.33 g, 2.24 mmol), 3,6-di-tert-butyl-carbazole (749 mg, 2.68 mmol) and $K_2CO_3$ (464 mg, 3.36 mmol) was dissolved in anhydrous DMF (40 mL). The mixture was stirred for 3 h at room temperature. And then water (60 mL) was added. The mixture was extracted with ethyl acetate (3×30 mL). The combined organic layers were dried with anhydrous $Na_2SO_4$ and evaporated under reduced pressure to obtain the crude product. The residue was purified by silica gel column chromatography (hexane/ethyl acetate=15:1) to yield 1.71 g (2.01 mmol, 91%) of the product as a pale yellow powder after removal of the solvent. $^1$H NMR (400 Hz, $CDCl_3$): 8.20 (dd, $J_1$=8.8 Hz, $J_2$=3.2 Hz, 2H), 8.09 (d, J=8.4 Hz, 2H), 7.81 (td, $J_1$=10.4 Hz, $J_2$=4.0 Hz, 2H), 7.68-7.56 (m, 8H), 7.51 (t, J=7.6 Hz, 2H), 7.22-7.08 (m, 4H), 7.04-6.93 (m, 2H), 6.74-6.67 (m, 2H), 6.59-6.53 (m, 2H). 1.40 (s, 9H), 1.30 (s, 9H). $^{13}$C NMR (100 Hz, $CDCl_3$): δ 150.9, 150.6, 149.4, 144.4, 144.1, 139.0, 138.5, 137.5, 136.9, 136.1, 134.9, 132.5, 132.1, 131.8, 128.6, 127.7, 126.8, 126.6, 125.7, 125.0, 124.8, 124.5, 124.3, 124.2, 124.0, 123.2, 122.5, 121.2, 120.9, 120.74, 120.71, 120.06, 119.56, 116.3, 115.7, 114.56, 114.47, 112.06, 111.93, 109.87, 109.81, 109.51, 109.31, 34.66, 34.47, 31.89, 31.74. HRMS (MALDI-TOF, m/z): [M]$^+$ calcd for $C_{60}H_{44}N_4O_2$, 852.3464. found, 852.3493.

Preparation of R/S-BN-DCB

To a mixture of R/S-1 (1.0 g, 2.24 mmol), 3,6-di-tert-butyl-carbazole (1.56 g, 5.60 mmol) and $K_2CO_3$ (1.54 g, 11.20 mmol), 40 mL anhydrous DMF was added. The reaction mixture was stirred at room temperature for 5 h. After completed the reaction, water (80 mL) was added. The mixture was extracted with ethyl acetate (3×40 mL). The combined organic layers were dried with anhydrous $Na_2SO_4$ and evaporated under reduced pressure to obtain the crude product. The residue was purified by silica-gel column chromatography using hexane/ethyl acetate (15:1) as an eluent. R/S-BN-DCB was obtained as a yellow solid in 81% yield (1.75 g, 1.81 mmol). $^1$H NMR (400 Hz, $CDCl_3$): δ 8.21 (d, J=8.8 Hz, 2H), 8.10 (d, J=8.0 Hz, 2H), 7.83 (d, J=8.8 Hz, 2H), 7.66-7.60 (m, 6H), 7.53-7.47 (m, 4H), 7.17 (d, J=8.8 Hz, 2H), 6.95 (d, J=8.4 Hz, 2H), 6.60 (d, J=8.8 Hz, 2H), 6.34 (d, J=8.4 Hz, 2H), 1.42 (s, 18H), 1.31 (s, 18H). $^{13}$C NMR (100 Hz, $CDCl_3$): δ 150.2, 149.5, 144.2, 143.8, 137.2, 136.6, 135.0, 132.5, 132.1, 131.8, 128.6, 127.6, 126.8, 126.6, 125.1, 124.7, 124.2, 123.3, 122.4, 120.8, 116.0, 115.3, 114.2, 112.3, 109.3, 109.2, 34.6, 34.4, 31.9, 31.8. HRMS (MALDI-TOF, m/z): [M]$^+$ calcd for $C_{68}H_{60}N_4O_2$, 964.4716. found, 964.4685.

Preparation of R/S-BN-AF

In a three-necked flask, 9,9-dimethyl-9,10-dihydroacridine (468 mg, 2.24 mmol) and t-BuOK (300 mg, 2.68 mmol) were dissolved in anhydrous $CH_3CN$ (30 mL) and followed by stirring at 90° C. for an hour. And then R/S-1 (1.0 g, 2.24 mmol) was added in the reaction and stirred at 90° C. for another 1.5 h. After cooling to room temperature, the solvent was removed by a rotary evaporator. And then water (60 mL) was added. The mixture was extracted with ethyl acetate (3×20 mL). The combined organic layers were dried with anhydrous $Na_2SO_4$ and evaporated under reduced pressure to obtain the crude product. The residue was purified by silica-gel column chromatography using hexane/ethyl acetate (15:1) as an eluent. R/S-BN-AF was obtained as an orange solid in 45% yield (630 mg, 1.0 mmol). $^1$H NMR (400 Hz, $CDCl_3$): δ 8.15 (d, J=8.8 Hz, 1H), 8.10 (d, J=9.2 Hz, 1H), 8.02 (t, J=7.6 Hz, 2H), 7.68 (d, J=8.8 Hz, 1H), 7.60-7.43 (m, 9H), 7.10 (t, J=6.0 Hz, 2H), 7.05 (t, J=4.4 Hz, 2H), 1.83 (s, 3H), 1.63 (s, 3H). $^{13}$C NMR (100 Hz, $CDCl_3$): δ 158.7, 156.1, 151.0, 148.7, 148.60, 148.56, 148.4, 137.6, 131.8, 131.7, 131.41, 131.35, 131.2, 130.7, 130.6, 128.0, 127.05, 126.8, 126.6, 126.5, 126.4, 126.11, 126.08, 126.06, 125.99, 125.44, 125.37, 124.29, 124.25, 122.1, 119.8, 119.6, 116.3, 116.2, 112.1, 111.8, 110.8, 110.7, 108.7, 103.0, 102.8, 35.5, 32.5, 28.4. HRMS (MALDI-TOF, m/z): [M]$^+$ calcd for $C_{43}H_{26}FN_3O_2$, 635.2009. found, 635.2019.

Fabrication of CPOLED

The Exemplary CPOLEDs were fabricated by sequential vacuum evaporation. The device configuration was as follows: indium tin oxide (ITO)/HATCN (10 nm)/TAPC:HATCN (5:2, 60 nm)/TCTA (20 nm)/mCP:10% target compounds (20 nm)/BmPyPB (10 nm)/BmPyPB:8% Liq (40 nm)/Liq (1.5 nm)/(Al). HATCN (dipyrazino[2,3-f:2′,3′-h]quinoxaline-2,3,6,7,10,11-hexacarbonitrile) and 8-hydroxyquinolinolato-lithium (Liq) serve as the hole-injection layer and the electron-injection layer, respectively. TCTA (tris(4-(9H-carbazol-9-yl)phenyl)amine) and TAPC (4,4'-(cyclohexane-1,1-diyl)bis(N,N-di-p-tolylaniline)) serve as the hole-transport layer and, BmPyPhB (3,3",5,5"-tetra(pyridin-3-yl)-1,1':3',1"-terphenyl) serves as the electron-transport layer. mCP acts as a host to confine the triplet excitons within the guest emitters. The details of device structures are illustrated in FIG. 24A, and the chemical structures of adopted materials are depicted in FIG. 24B.

What is claimed is:

1. A compound of Formula I:

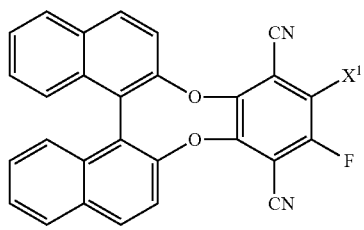

wherein $X^1$ is selected from the group consisting of:

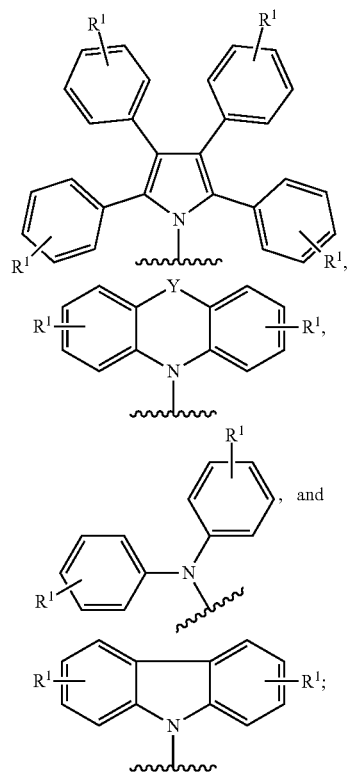

$R^1$ for each instance is independently selected from the group consisting of halide, H, alkyl, alkene, alkyne, heteroalkyl, cycloalkyl, heterocycloalkyl, aryl, heteroaryl, carboxyl, —$NR_2$, sulfonic acid, —SR, and —OR;

Y is —N(R)—, O, S, Se, Te, or —C(R)$_2$—;

wherein at least one $R^1$ optionally further comprises a terminal functional group selected from the group consisting of $N_3$, NCS, SH, $NH_2$, COOH, alkyne, N-hydroxysuccinimide ester, maleimide, hydrazide, nitrone group, —CHO, OH, halide, and charged ionic group; and R for each instance is independently selected from the group consisting of H, alkyl, cycloalkylaryl, aryl, and heteroaryl, wherein the compound of Formula I is isolated, pure, or present in a film.

2. The compound of claim 1, wherein $R^1$ for each instance is independently selected from the group consisting of H and alkyl.

3. The compound of claim 1, wherein $R^1$ for each instance is independently selected from the group consisting of:

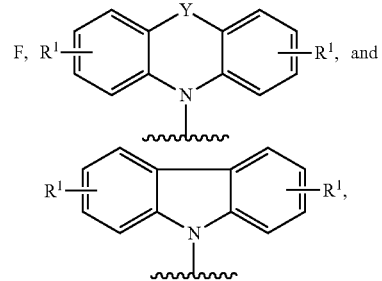

wherein Y is —N(R)—, O, or —C(R)$_2$— and R is independently H or alkyl.

4. The compound of claim 1, wherein $X^1$ is

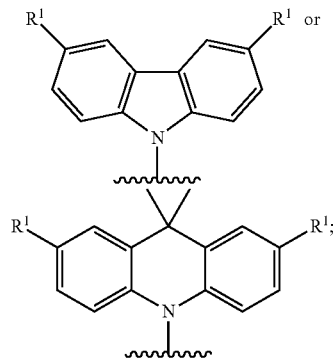

and $R^1$ for each instance is H or alkyl.

5. The compound of claim 1, wherein the compound of Formula I is represented by:

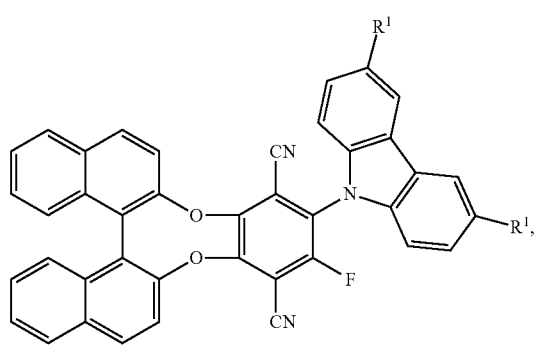

wherein $R^1$ is H or alkyl.

6. The compound of claim 1, wherein the compound of Formula I is represented by:

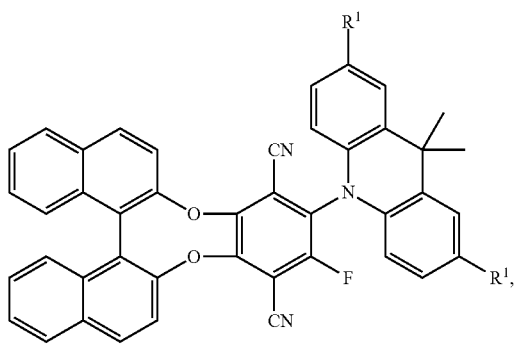

wherein R¹ is H or alkyl.

7. The compound of claim 1, wherein the compound of Formula I is selected from the group consisting of:

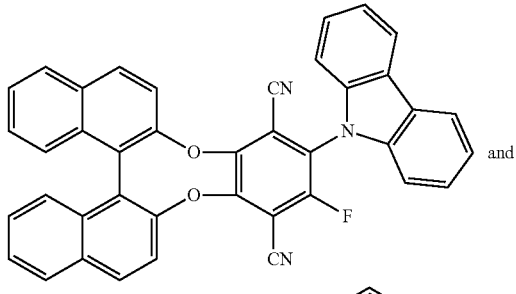

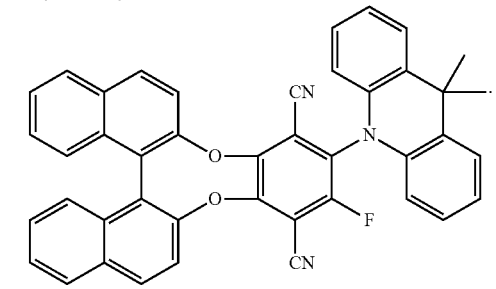

8. The compound of claim of claim 1, wherein the compound exhibits a photoluminescence dissymmetry factor in the solid state between 0.02 to 0.05 calculated from the maximum emission wavelength.

9. An electroluminescent device comprising the compound of claim 1.

10. The electroluminescent device of claim 9, wherein the electroluminescent device comprises:
- an anode;
- a hole-injection layer;
- a hole-transport layer;
- an electron-transport layer;
- an electron-injection layer;
- a light-emitting layer comprising the compound of Formula I; and
- a cathode layer, wherein at least one of the anode layer and the cathode layer being substantially transparent to electroluminescent light.

11. The electroluminescent device of claim 10, wherein the light-emitting layer further comprises a host matrix and the compound of Formula I is used as a dopant material.

12. The electroluminescent device of claim 9, wherein the compound of Formula I is:

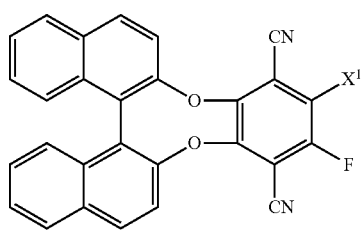

wherein X¹ is

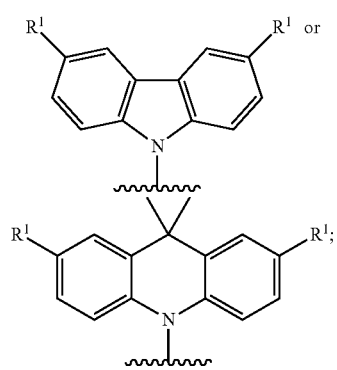

and

R¹ for each instance is H or alkyl.

13. The electroluminescent device of claim 9, wherein the compound of Formula I is selected from the group consisting of:

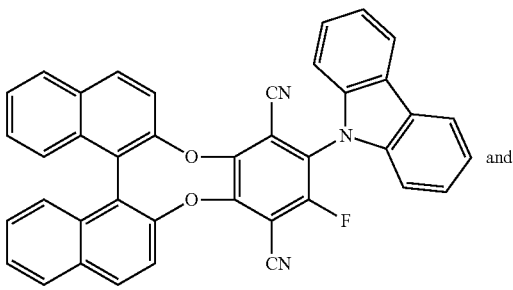

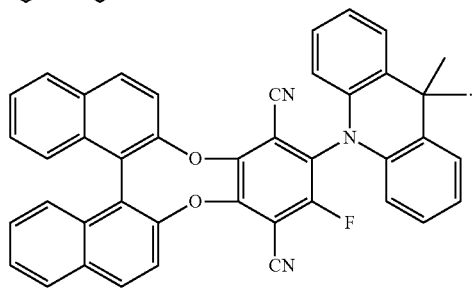

14. The electroluminescent device of claim 10, wherein the electron-injection layer comprises lithium-8-hydroxyquinolinolate (Liq), the electron-transport layer comprises 1,3-bis[3,5-di(pyridin-3-yl)phenyl]benzene (BmPyPhB), the hole-injection layer comprises 1,4,5,8,9,11-hexaazatriphenylenehexacarbonitrile (HATCN), the hole-transport layer comprises (TCTA), and the light-emitting layer further comprises N,N'-dicarbazolyl-3,5-benzene (mCP).

15. The electroluminescent device of claim 14, wherein the compound of Formula I is selected from the group consisting of:

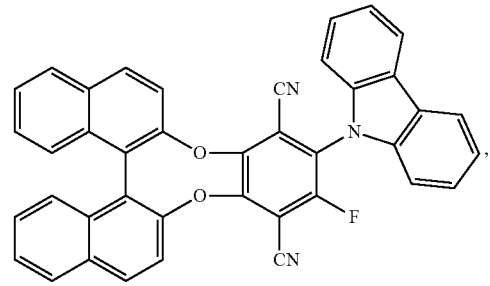

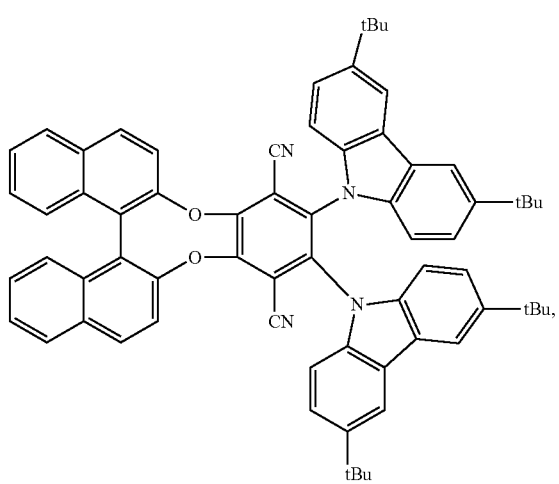

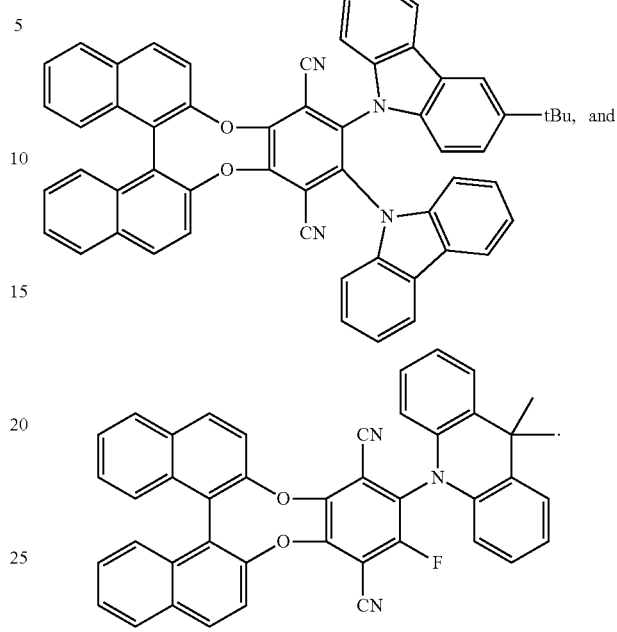

16. The electroluminescent device of claim 10, wherein the compound exhibits an electroluminescence dissymmetry factor between 0.05 to 0.090 calculated from the maximum emission wavelength.

17. The electroluminescent device of claim 10, wherein the electroluminescent device has a maximum power efficiency between 18 to 20 lm·W$^{-1}$.

18. The electroluminescent device of claim 10, wherein the electroluminescent device has a turn on voltage of 3.4 to 3.8 volts.

* * * * *